United States Patent [19]
Becquart et al.

[11] Patent Number: 6,165,470
[45] Date of Patent: Dec. 26, 2000

[54] ALBUMIN DERIVATIVES WITH THERAPEUTIC FUNCTIONS

[75] Inventors: Jérôme Becquart, Paris; Reinhard Fleer, Gif sur Yvette; Philippe Hirel, Paris; David Klatzmann, Paris; Didier Landais, Paris; Jean-François Mayaux, Fontenay aux Roses; Patrice Yeh, Paris, all of France

[73] Assignee: Rhone-Poulenc, Antony, France

[21] Appl. No.: 09/004,319

[22] Filed: Jan. 8, 1998

Related U.S. Application Data

[63] Continuation of application No. 08/479,146, Jun. 7, 1995, abandoned, which is a continuation of application No. 08/295,078, Aug. 26, 1994, abandoned, which is a continuation of application No. 08/121,236, Sep. 13, 1993, abandoned, which is a continuation of application No. 07/955,243, Oct. 1, 1992, abandoned, which is a continuation of application No. 07/561,879, Aug. 2, 1990, abandoned.

[30] Foreign Application Priority Data

Aug. 3, 1989 [FR] France ................................. 89 10480

[51] Int. Cl.$^7$ ........................ A61K 39/00; A61K 39/21; C12P 21/04; C07K 14/00
[52] U.S. Cl. .................... 424/185.1; 424/186.1; 424/188.1; 424/192.1; 424/194.1; 435/69.7; 530/350; 530/365
[58] Field of Search ................ 435/69.7; 514/2, 514/8, 12, 776; 530/350, 365, 402; 424/134.1, 185.1, 188.1, 192.1, 194.1, 186.1; 436/88

[56] References Cited

U.S. PATENT DOCUMENTS

| | | | |
|---|---|---|---|
| 4,336,248 | 6/1982 | Bonhard et al. | 530/354 |
| 4,914,027 | 4/1990 | Knapp et al. | 435/69.6 |
| 4,970,300 | 11/1990 | Fulton | 530/383 |
| 5,116,944 | 5/1992 | Sivam et al. | 530/362 |
| 5,302,697 | 4/1994 | Goodey et al. | 530/325 |
| 5,336,603 | 8/1994 | Capon et al. | 435/69.7 |

FOREIGN PATENT DOCUMENTS

| | | |
|---|---|---|
| 0163406 | 12/1985 | European Pat. Off. . |
| 0244221 | 11/1987 | European Pat. Off. . |
| 0301670 | 2/1989 | European Pat. Off. . |
| 0325262 | 7/1989 | European Pat. Off. . |

OTHER PUBLICATIONS

Capon et al., Designing CD4 immunoadhesins for AIDS therapy, Nature, 337:525–531 (1989).

Reed et al., Non–resolving jaundice: bilirubin covalently attached to serum albumin circulates with the same metabolic half–life as albumin, Chem. Abst. vol. 109, Abst. No. 227803q (1988).

Ogino et al., Chemical modification of superoxide dismutase, Chem. Abstr. vol. 109, Abst. No. 163477u (1988).

Clement et al., Expression in *E. Coli* of a MalE–CD4 hybrid protein which is purified in one step and neutralizes the HIV virus in vitro, C.R. Acad. Sci. Paris (Series III) 308:401–406 (1989).

Hammarberg et al., Dual affinity fusion approach and its use to express recombinant human insulin–like growth factor II, Proc. Natl. Acad. Sci. (USA) 86:4367–4371 (1989).

Semba et al., A v–erbB–related protooncogene, c–erbB–2, is distinct from the c–erbB–1/epidermal growth factor–receptor gene and is amplified in a human salivary gland adenocarcinoma, Proc. Natl. Acad. Sci. (USA), vol. 82–6497–6501 (1985).

Simmons et al., The Fc–gamma receptor of natural killer cells is a phospolipid–linked membrane protein, Nature, 333:568–570 (1988).

Berger et al., A soluble recombinant polypeptide comprising the amino–terminal half of the extracellular region of the CD4 molecule contains an active binding site for human immunodeficiency virus, Proc. Natl. Acad. Sci. 85;2357–2361 (1988).

Jameson et al., Location and chemical synthesis of a binding site for HIV–1 on the CD4 protein, Science 240;1335–1339 (1988).

Traunecker et al., Soluble CD4 molecules neutralize human immunodeficiency virus type 1, Nature 331; 84–86 (1988).

Hu et al., Protection of macaques against siv infection by subunit vaccines of siv envelope glycoprotein gp 160, Science 255;456–459 (1992).

Bolognesi (1989) Science 246, 1233–1234.

*Primary Examiner*—Donald E. Adams
*Assistant Examiner*—P. Ponnalun
*Attorney, Agent, or Firm*—Finnegan, Henderson, Farabow, Garrett & Dunner, L.L.P.

[57] ABSTRACT

Utilization of albumin as a stable plasma transporter with a therapeutic function that is derived from a membrane receptor. The present invention is exemplified by the description of new therapeutic agents that can be used in the treatment of Acquired Immunodeficiency Syndrome: hybrid macromolecules composed of albumin derivatives coupled to derivatives of the CD4 receptor having a normal or a higher affinity for the HIV-1 virus.

15 Claims, 43 Drawing Sheets

```
     MstII
  CCTTAGGCTTAAAGAAAGTGGTGCTGGGCAAAAAAGGGGATACAGTGGAACTGACCTGTACAGCTTCCCAGAAGA
 01       11        21        31        41        51        61        71

AGAGCATACAATTCCACTGGAAAAACTCCAACCAGATAAAGATTCTGGGAAATCAGGGCTCCTTCTTAACTAAAG
 76        86        96       106       116       126       136       146

GTCCATCCAAGCTGAATGATCGCGCTGACTCAAGAAGAAGCCTTTGGGACCAAGGAAACTTCCCCCTGATCATCA
151       161       171       181       191       201       211       221

AGAATCTTAAGATAGAAGACTCAGATACTTACATCTGTGAAGTGGAGGACCAGAAGGAGGAGGTGCAATTGCTAG
226       236       246       256       266       276       286       296

TGTTCGGATTGACTGCCAACTCTGACACCCACCTGCTTCAGGGGCAGAGCCTGACCCTGACCTTGGAGAGCCCCC
301       311       321       331       341       351       361       371

CTGGTAGTAGCCCCTCAGTGCAATGTAGGAGTCCAAGGGGTAAAAACATACAGGGGGGGAAGACCCTCTCCGTGT
376       386       396       406       416       426       436       446

CTCAGCTGGAGCTCCAGGATAGTGGCACCTGGACATGCACTGTCTTGCAGAACCAGAAGAAGGTGGAGTTCAAAA
451       461       471       481       491       501       511       521

HindIII SmaI
  TAGACATCGTGGTGCTAGCTTTCTAAAAGCTTCCCGGG
526       536       546       556
```

*FIG. 2*

```
              MetLysTrpValThrPheIleSerLeuLeuPheLeuPheSerSerAlaTyrSerArgGlyValPheArg
   AAGCTTATGAAGTGGGTAACCTTTATTTCCCTTCTTTTTCTCTTTAGCTCGGCTTATTCCAGGGGTGTGTTTCGT
   1         11        21        31        41        51        61        71

ArgAspAlaHisLysSerGluValAlaHisArgPheLysAspLeuGlyGluGluAsnPheLysAlaLeuValLeu
   CGAGATGCACACAAGAGTGAGGTTGCTCATCGGTTTAAAGATTTGGGAGAAGAAAATTTCAAAGCCTTGGTGTTG
   76        86        96        106       116       126       136       146

IleAlaPheAlaGlnTyrLeuGlnGlnCysProPheGluAspHisValLysLeuValAsnGluValThrGluPhe
   ATTGCCTTTGCTCAGTATCTTCAGCAGTGTCCATTTGAAGATCATGTAAAATTAGTGAATGAAGTAACTGAATTT
   151       161       171       181       191       201       211       221
    AlaLysThrCysValAlaAspGluSerAlaGluAsnCysAspLysSerLeuHisThrLeuPheGlyAspLysLeu
   GCAAAAACATGTGTTGCTGATGAGTCAGCTGAAAATTGTGACAAATCACTTCATACCCTTTTTGGAGACAAATTA
   226       236       246       256       266       276       286       296

CysThrValAlaThrLeuArgGluThrTyrGlyGluMetAlaAspCysCysAlaLysGlnGluProGluArgAsn
   TGCACAGTTGCAACTCTTCGTGAAACCTATGGTGAAATGGCTGACTGCTGTGCAAAACAAGAACCTGAGAGAAAT
   301       311       321       331       341       351       361       371

GluCysPheLeuGlnHisLysAspAspAsnProAsnLeuProArgLeuValArgProGluValAspValMetCys
   GAATGCTTCTTGCAACACAAAGATGACAACCCAAACCTCCCCCGATTGGTGAGACCAGAGGTTGATGTGATGTGC
   376       386       396       406       416       426       436       446

ThrAlaPheHisAspAsnGluGluThrPheLeuLysLysTyrLeuTyrGluIleAlaArgArgHisProTyrPhe
   ACTGCTTTTCATGACAATGAAGAGACATTTTTGAAAAAATACTTATATGAAATTGCCAGAAGACATCCTTACTTT
   451       461       471       481       491       501       511       521

TyrAlaProGluLeuLeuPhePheAlaLysArgTyrLysAlaAlaPheThrGluCysCysGlnAlaAlaAspLys
   TATGCCCCGGAACTCCTTTTCTTTGCTAAAAGGTATAAAGCTGCTTTTACAGAATGTTGCCAAGCTGCTGATAAA
   526       536       546       556       566       576       586       596
```

FIG. 8A

```
AlaAlaCysLeuLeuProLysLeuAspGluLeuArgAspGluGlyLysAlaSerSerAlaLysGlnArgLeuLys
GCTGCCTGCCTGTTGCCAAAGCTCGATGAACTTCGGGATGAAGGGAAGGCTTCGTCTGCCAAACAGAGACTCAAG
601       611       621       631       641       651       661       671

CysAlaSerLeuGlnLysPheGlyGluArgAlaPheLysAlaTrpAlaValAlaArgLeuSerGlnArgPhePro
TGTGCCAGTCTCCAAAAATTTGGAGAAAGAGCTTTCAAAGCATGGGCAGTAGCTCGCCTGAGCCAGAGATTTCCC
676       686       696       706       716       726       736       746

LysAlaGluPheAlaGluValSerLysLeuValThrAspLeuThrLysValHisThrGluCysCysHisGlyAsp
AAAGCTGAGTTTGCAGAAGTTTCCAAGTTAGTGACAGATCTTACCAAAGTCCACACGGAATGCTGCCATGGAGAT
751       761       771       781       791       801       811       821

LeuLeuGluCysAlaAspAspArgAlaAspLeuAlaLysTyrIleCysGluAsnGlnAspSerIleSerSerLys
CTGCTTGAATGTGCTGATGACAGGGCGGACCTTGCCAAGTATATCTGTGAAAATCAAGATTCGATCTCCAGTAAA
826       836       846       856       866       876       886       896
LeuLysGluCysCysGluLysProLeuLeuGluLysSerHisCysIleAlaGluValGluAsnAspGluMetPro
CTGAAGGAATGCTGTGAAAAACCTCTGTTGGAAAAATCCCACTGCATTGCCGAAGTGGAAAATGATGAGATGCCT
901       911       921       931       941       951       961       971
AlaAspLeuProSerLeuAlaAlaAspPheValGluSerLysAspValCysLysAsnTyrAlaGluAlaLysAsp
GCTGACTTGCCTTCATTAGCTGCTGATTTTGTTGAAAGTAAGGATGTTTGCAAAAACTATGCTGAGGCAAAGGAT
976       986       996       1006      1016      1026      1036      1046
```

FIG. 8A (CONT.)

```
         ValPheLeuGlyMetPheLeuTyrGluTyrAlaArgArgHisProAspTyrSerValValLeuLeuArgLeu
         GTCTTCCTGGGCATGTTTTTGTATGAATATGCAAGAAGGCATCCTGATTACTCTGTCGTACTGCTGCTGAGACTT
1051     1061      1071      1081      1091      1101      1111      1121

AlaLysThrTyrGluThrThrLeuGluLysCysCysAlaAlaAlaAspProHisGluCysTyrAlaLysValPhe
         GCCAAGACATATGAAACCACTCTAGAGAAGTGCTGTGCCGCTGCAGATCCTCATGAATGCTATGCCAAAGTGTTC
1126     1136      1146      1156      1166      1176      1186      1196

AspGluPheLysProLeuValGluGluProGlnAsnLeuIleLysGlnAsnCysGluLeuPheGluGlnLeuGly
         GATGAATTTAAACCTCTTGTGGAAGAGCCTCAGAATTTAATCAAACAAAATTGTGAGCTTTTTGAGCAGCTTGGA
1201     1211      1221      1231      1241      1251      1261      1271

GluTyrLysPheGlnAsnAlaLeuLeuValArgTyrThrLysLysValProGlnValSerThrProThrLeuVal
         GAGTACAAATTCCAGAATGCGCTATTAGTTCGTTACACCAAGAAAGTACCCCAAGTGTCAACTCCAACTCTTGTA
1276     1286      1296      1306      1316      1326      1336      1346

GluValSerArgAsnLeuGlyLysValGlySerLysCysCysLysHisProGluAlaLysArgMetProCysAla
         GAGGTCTCAAGAAACCTAGGAAAAGTGGGCAGCAAATGTTGTAAACATCCTGAAGCAAAAAGAATGCCCTGTGCA
1351     1361      1371      1381      1391      1401      1411      1421

GluAspTyrLeuSerValValLeuAsnGlnLeuCysValLeuHisGluLysThrProValSerAspArgValThr
         GAAGACTATCTATCCGTGGTCCTGAACCAGTTATGTGTGTTGCATGAGAAAACGCCAGTAAGTGACAGAGTCACC
1426     1436      1446      1456      1466      1476      1486      1496

LysCysCysThrGluSerLeuValAsnArgArgProCysPheSerAlaLeuGluValAspGluThrTyrValPro
         AAATGCTGCACAGAATCCTTGGTGAACAGGCGACCATGCTTTTCAGCTCTGGAAGTCGATGAAACATACGTTCCC
1501     1511      1521      1531      1541      1551      1561      1571

LysGluPheAsnAlaGluThrPheThrPheHisAlaAspIleCysThrLeuSerGluLysGluArgGlnIleLys
         AAAGAGTTTAATGCTGAAACATTCACCTTCCATGCAGATATATGCACACTTTCTGAGAAGGAGAGACAAATCAAG
1576     1586      1596      1606      1616      1626      1636      1646

LysGlnThrAlaLeuValGluLeuValLysHisLysProLysAlaThrLysGluGlnLeuLysAlaValMetAsp
         AAACAAACTGCACTTGTTGAGCTTGTGAAACACAAGCCCAAGGCAACAAAAGAGCAACTGAAAGCTGTTATGGAT
1651     1661      1671      1681      1691      1701      1711      1721
```

FIG. 8B

```
  AspPheAlaAlaPheValGluLysCysCysLysAlaAspAspLysGluThrCysPheAlaGluGluGlyLysLys
  GATTTCGCAGCTTTTGTAGAGAAGTGCTGCAAGGCTGACGATAAGGAGACCTGCTTTGCCGAGGAGGGTAAAAAA
1726      1736      1746      1756      1766      1776      1786      1796
  LeuValAlaAlaSerGlnAlaAlaLeuGlyLeuLysLysValValLeuGlyLysLysGlyAspThrValGluLeu
  CTTGTTGCTGCAAGTCAAGCTGCCTTAGGCTTAAAGAAAGTGGTGCTGGGCAAAAAAGGGGATACAGTGGAACTG
1801      1811      1821      1831      1841      1851      1861      1871
  ThrCysThrAlaSerGlnLysLysSerIleGlnPheHisTrpLysAsnSerAsnGlnIleLysIleLeuGlyAsn
  ACCTGTACAGCTTCCCAGAAGAAGAGCATACAATTCCACTGGAAAAACTCCAACCAGATAAAGATTCTGGGAAAT
1876      1886      1896      1906      1916      1926      1936      1946
  GlnGlySerPheLeuThrLysGlyProSerLysLeuAsnAspArgAlaAspSerArgArgSerLeuTrpAspGln
  CAGGGCTCCTTCTTAACTAAAGGTCCATCCAAGCTGAATGATCGCGCTGACTCAAGAAGAAGCCTTTGGGACCAA
1951      1961      1971      1981      1991      2001      2011      2021
  GlyAsnPheProLeuIleIleLysAsnLeuLysIleGluAspSerAspThrTyrIleCysGluValGluAspGln
  GGAAACTTCCCCCTGATCATCAAGAATCTTAAGATAGAAGACTCAGATACTTACATCTGTGAAGTGGAGGACCAG
2026      2036      2046      2056      2066      2076      2086      2096
  LysGluGluValGlnLeuLeuValPheGlyLeuThrAlaAsnSerAspThrHisLeuLeuGlnGlyGlnSerLeu
  AAGGAGGAGGTGCAATTGCTAGTGTTCGGATTGACTGCCAACTCTGACACCCACCTGCTTCAGGGGCAGAGCCTG
2101      2111      2121      2131      2141      2151      2161      2171
```

FIG. 8B (CONT.)

```
    ThrLeuThrLeuGluSerProProGlySerSerProSerValGlnCysArgSerProArgGlyLysAsnIleGln
    ACCCTGACCTTGGAGAGCCCCCCTGGTAGTAGCCCCTCAGTGCAATGTAGGAGTCCAAGGGGTAAAAACATACAG
2176      2186      2196      2206      2216      2226      2236      2246

GlyGlyLysThrLeuSerValSerGlnLeuGluLeuGlnAspSerGlyThrTrpThrCysThrValLeuGlnAsn
    GGGGGGAAGACCCTCTCCGTGTCTCAGCTGGAGCTCCAGGATAGTGGCACCTGGACATGCACTGTCTTGCAGAAC
2251      2261      2271      2281      2291      2301      2311      2321

GlnLysLysValGluPheLysIleAspIleValValLeuAlaPhe***
    CAGAAGAAGGTGGAGTTCAAAATAGACATCGTGGTGCTAGCTTTCTAAAAGCTT
2326      2336      2346      2356      2366      2376
```

FIG. 8C

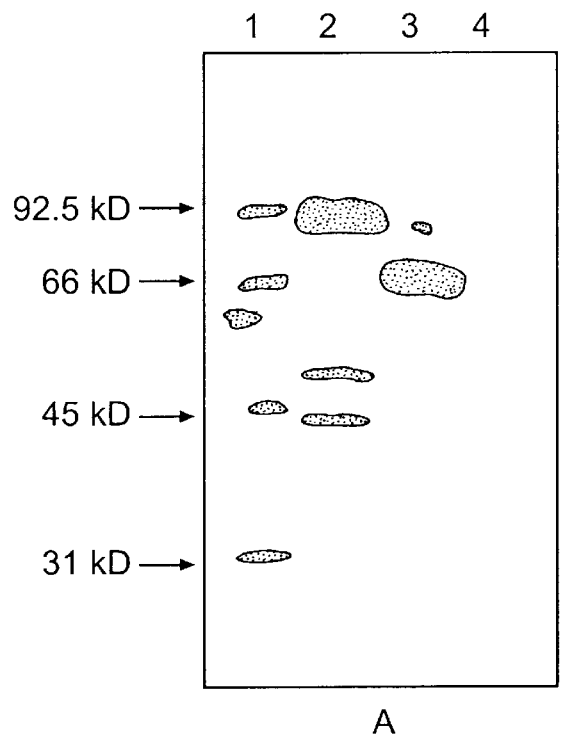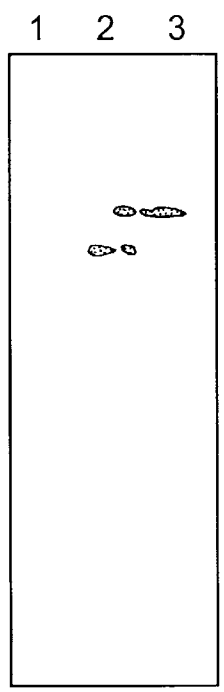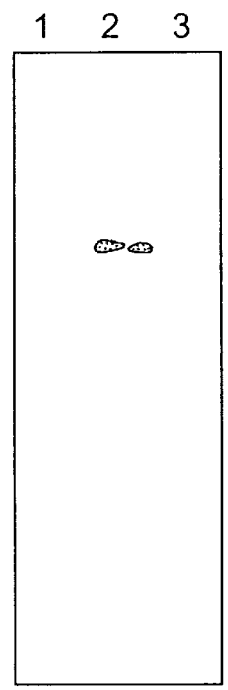
FIG. 18

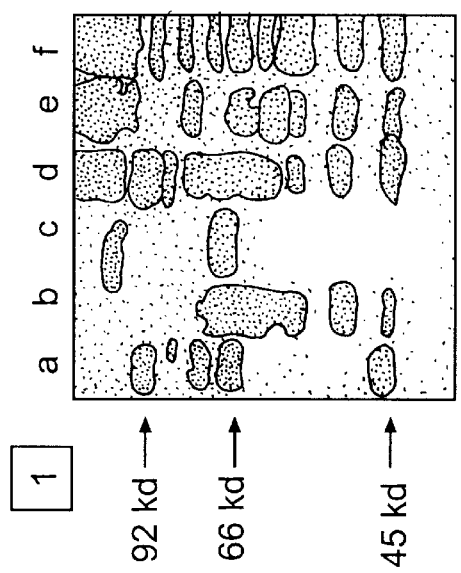
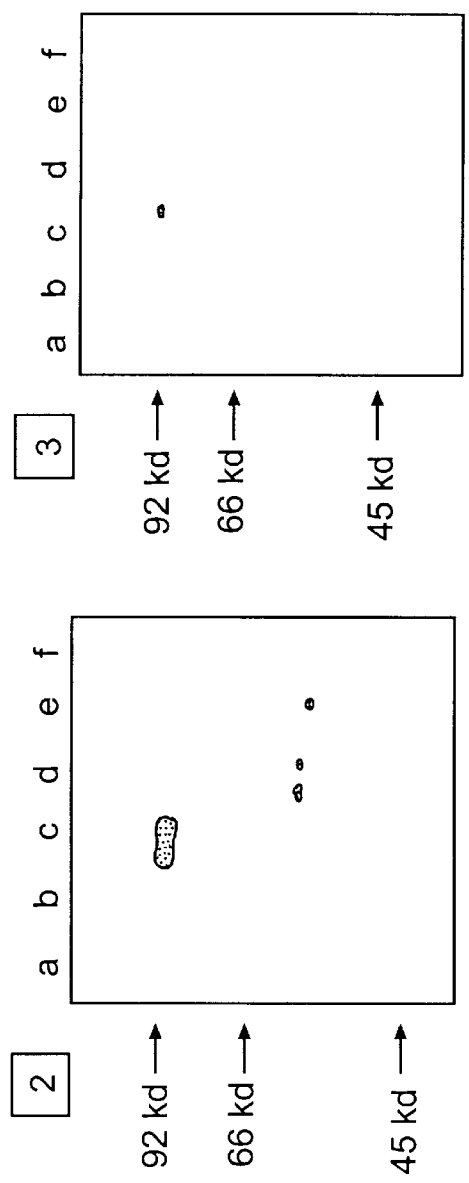
FIG. 35

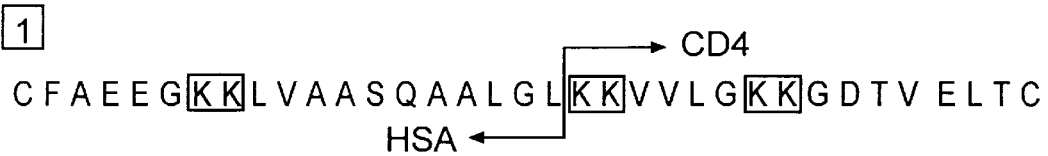
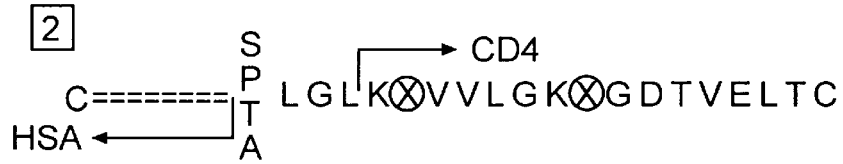
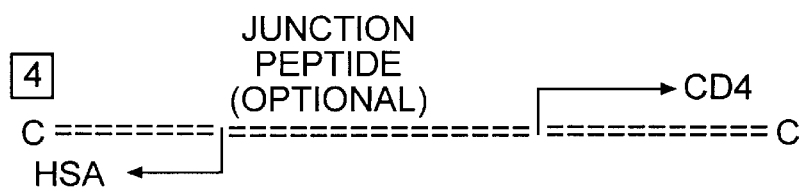
FIG. 37

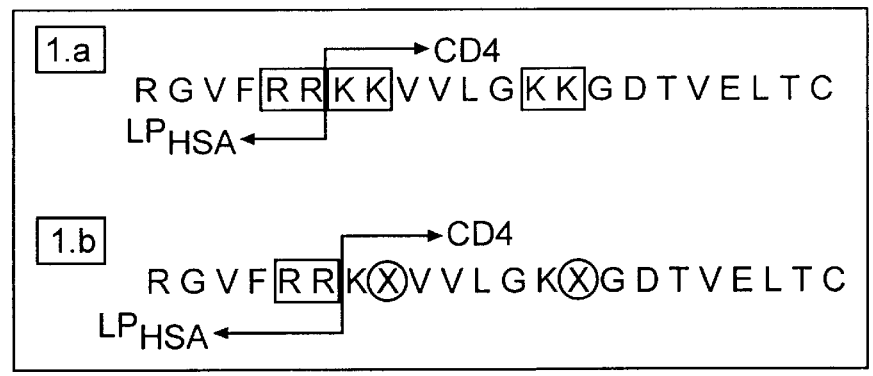
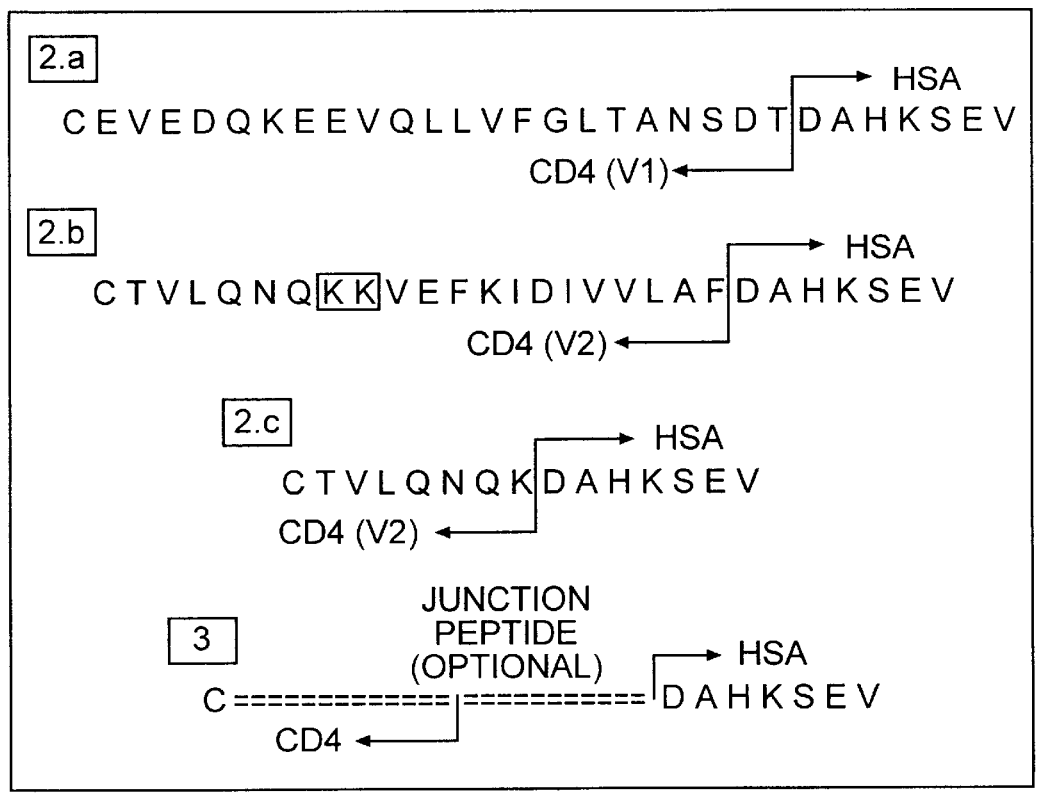
FIG. 38

ALBUMIN DERIVATIVES WITH THERAPEUTIC FUNCTIONS

This is a continuation of application Ser. No. 08/479,146 filed Jun. 7, 1995, now abandoned which is a continuation of application Ser. No. 08/295,078, filed Aug. 26, 1994, now abandoned, which is a continuation of application Ser. No. 08/121,236, filed Sep. 13, 1993, now abandoned, which is a continuation of application Ser. No. 07/955,243, filed Oct. 1, 1992, now abandoned, which is a continuation of application Ser. No. 07/561,879, filed Aug. 2, 1990, now abandoned.

The present invention involves the utilization of albumin derivatives in the fabrication of therapeutic agents that can be used in the treatment of certain viral diseases and cancers. More precisely, this invention involves hybrid macromolecules characterized by the fact that they carry either the active domain of a receptor for a virus, or the active domain of a molecule which can bind to a virus, or the active domain of a molecule able to recognize the Fc fragment of immunoglobulins bound to a virus, or the active domain of a molecule able to bind a ligand that intervenes in a pathologic process, coupled to albumin or a variant of albumin. In the text that follows, the terms albumin derivatives or albumin variants are meant to designate all proteins with a high plasma half-life obtained by modification (mutation, deletion, and/or addition) via the techniques of genetic engineering of a gene encoding a given isomorph of albumin, as well as all macromolecules with high plasma half-life obtained by the in vitro modification of the protein encoded by such genes. Such albumin derivatives can be used as pharmaceuticals in antiviral treatment due to the high affinity of a virus or of an immunoglobulin bound to a virus for a site of fixation present on the albumin derivative. They can be used as pharmaceuticals in the treatment of certain cancers due to the affinity of a ligand, for example a growth factor, for a site of fixation present on the albumin derivative, especially when such a ligand is associated with a particular membrane receptor whose amplification is correlated with a transforming phenotype (proto-oncogenes). It should be understood in the text that follows that all functionally therapeutic albumin derivatives are designated indifferently by the generic term of hybrid macromolecules with antiviral function, or hybrid macromolecules with anticancer function, or simply hybrid macromolecules. In particular, the present invention consists in the obtention of new therapeutic agents characterized by the coupling, through chemical or genetic engineering techniques, of at least two distinct funtions:

(i) a stable plasma transporter function provided by any albumin variant, and in particular by human serum albumin (HSA). The genes coding for HSA are highly polymorphic and more than 30 different genetic alleles have been reported (Weitkamp L. R. et al., Ann. Hum. Genet. 37 (1973) 219–226). The albumin molecule, whose three-dimensional structure has been characterized by X-ray diffraction (Carter D. C. et al. Science 244 (1989) 1195–1198), was chosen to provide the stable transporter function because it is the most abundant plasma protein (40 g per liter in humans), it has a high plasma half-life (14–20 days in humans, Waldmann T. A., in "Albumin Structure, Function and Uses", Rosenoer V. M. et al. (eds), Pergamon Press, Oxford, (1977) 255–275), and above all it has the advantage of being devoid of enzymatic function, thus permitting its therapeutic utilization at high doses.

(ii) an antiviral or anticancer therapeutic function. The antiviral function is to serve as a decoy for the specific binding of a virus, or as a decoy for the binding of a virus-immunoglobulin complex. For example, the antiviral function can be provided by all of part of a specific receptor normally used by a virus for its propagation in the host organism, or by any molecule capable of binding such a virus with an affinity high enough to permit its utilization in vivo as an antiviral agent. The antiviral function can also be provided by all or part of a receptor capable of recognizing immunoglobulins complexed with a virus, or by any molecule capable of binding such complexes with an affinity high enough to permit its utilization in vivo as an antiviral agent. The anti-cancer function is to serve as a decoy for the binding of a ligand and in particular a growth factor implicated in an oncogenic process, and is provided by all or part of a cellular proto-oncogene, or by any molecule capable of binding such a ligand with an affinity high enough to allow its utilization in vivo as an anticancer agent.

(iii) in cases where a high local concentration of the therapeutic function is desirable, for example because it synergizes an inhibition of the infectivity of a virus in vivo, a third function allowing the dimerization or the polymerization of the therapeutically active hybrid macromolecule can be added, possibly in a redundant fashion. For example, such a function could be provided by a "leucine zipper" motif (Landschulz W. H. et al., Science 240 (1988) 1759–1764), or by protein domains known to be necessary for homodimerization of certain proteins such as the domain of the product of the tat gene coded by the HIV-1 viral genome (Frankel A. D. et al., Science 240 (1988) 70–73; Frankel A. D. et al., Proc. Natl. Acad. Sci. USA 85 (1988) 6297–6300).

In the present invention, the plasma transporter function, the therapeutic function, and a potential polymerization function, are integrated into the same macromolecule using the techniques of genetic engineering.

One of the goals of the present invention is to obtain hybrid macromolecules derived from HSA which can be useful in the fight against certain viral diseases, such as Acquired Immunodeficiency Syndrome (AIDS). Another goal is to obtain hybrid HSA macromolecular derivatives useful in the treatment of certain cancers, notably those cancers associated with genomic amplification and/or overexpression of human proto-oncogenes, such as the proto-oncogene c-erbB-2 (Semba K. et al., Proc. Natl. Acad. Sci. USA. 82 (1985) 6497–6501; Slamon D. J. et al., Science 235 (1987) 177–182; Kraus M. H. et al., EMBO J. 6 (1987) 605–610).

The HIV-1 virus is one of the retroviruses responsible for Acquired Immunodeficiency Syndrome in man. This virus has been well studied over the past five years; a fundamental discovery concerns the elucidation of the role of the CD4 (T4) molecule as the receptor of the HIV-1 virus (Dalgleish A. G. et al., Nature 312 (1984) 763–767; Klatzmann D. et al., Nature 312 (1984) 767–768). The virus-receptor interaction occurs through the highly specific binding of the viral envelope protein (gp120) to the CD4 molecule (McDougal et al., Science 231 (1986) 382–385). The discovery of this interaction between the HIV-1 virus and certain T lymphocytes was the basis of a patent claiming the utilization of the T4 molecule or its antibodies as therapeutic agents against the HIV-1 virus (French patent application FR 2 570 278).

The cloning and the first version of the sequence of the gene encoding human CD4 has been described by Maddon et al. (Cell 42 (1985) 93–104), and a corrected version by Littmann et al. (Cell 55 (1988) 541): the CD4 molecule is a member of the super-family of immunoglobulins and specifically, it carries a V1 N-terminal domain which is substantially homologous to the immunoglobulin heavy chain variable domain (Maddon P. J. et al., Cell 42 (1985) 93–104). Experiments involving in vitro DNA recombination, using the gene coding for the CD4 molecule, have provided definite proof that the product of the CD4 gene is the principal receptor of the HIV-1 virus (Maddon P. J. et al., Cell 47 (1986) 333–348). The sequence of this gene as well as its utilization as an anti-HIV-1 therapeutic agent are discussed in International patent application WO 88 013 040 A1.

The manipulation of the CD4 gene by the techniques of DNA recombination has provided a series of first generation soluble variants capable of antiviral action in vitro (Smith D. H. et al., Science 238 (1987) 1704–1707; Traunecker A. et al., Nature 331 (1988) 84–86; Fischer R. A. et al., Nature 331 (1988) 76–78; Hussey R. E. et al., Nature 331 (1988) 78–81; Deen K. C. et al., Nature 331 (1988) 82–84), and in vivo (Watanabe M. et al., Nature 337 (1989) 267–270). In all cases, it was observed during various in vivo assays in animals (rabbit, monkey) as well as during phase I clinical trials, that the first generation soluble CD4 variant consisting of the CD4 molecule lacking the two domains in the C-terminal region has a very short half-life: approximately 15 minutes in rabbits (Capon et al., Nature 337 (1989) 525–531), while 50% of first generation soluble CD4 administered intramuscularly to Rhesus monkeys remained bioavailable for 6 hours (Watanabe et al., Nature 337 (1989) 267–270). In addition, Phase 1 clinical trials conducted on 60 patients presenting AIDS or ARC ("Aids Related Complex") indicated that the half-life of the Genentech product varied between 60 minutes (intraveinous administration) and 9 hours (intramuscular administration) (AIDS/HIV Experimental Treatment Directory, AmFAR, May 1989). Clearly, a therapeutic agent with such a weak stability in vivo constitutes a major handicap. In effect, repeated injections of the product, which are costly and inconvenient for the patient, or an administration of the product by perfusion, become necessary to attain an efficient concentration in plasma. It is therefore especially important to find derivatives of the CD4 molecule characterized by a much higher in vivo half-life.

The part of the CD4 molecule which interacts with the HIV-1 virus has been localized to the N-terminal region, and in particular to the V1 domain (Berger E. A. et al., Proc. Natl. Acad. Sci. USA 85 (1987) 2357–2361). It has been observed that a significant proportion (about 10%) of HIV-1-infected subjects develop an immune response against the CD4 receptor, with antibodies directed against the C-terminal region of the extra-cellular portion of the receptor (Thiriart C. et al., AIDS 2 (1988) 345–352; Chams V. et al., AIDS 2 (1988) 353–361). Therefore, according to a preferred embodiment of the present invention, only the N-terminal domains V1 or V1V2 of the CD4 molecule, which carry all the viral binding activity, will be used in fusion with the stable transporter function derived from albumin.

On the basis of the homology observed with the variable domain of immunoglobulins, several laboratories have constructed genetic fusions between the CD4 molecule and different types of immunoglobulins, generating hybrid immunoglobulins with antiviral action in vitro (Capon D. J. et al., Nature 337 (1989) 525–531; Traunecker A. et al., Nature 339 (1989) 68–70; also see International patent application WO 89 02922). However, the implication of the FcγRIII receptor (type 3 receptor for the Fc region of IgG's), which in humans is the antigen CD16 (Unkeless J. C. and Jacquillat C., J. Immunol. Meth. 100 (1987) 235–241), in the internalization of the HIV-1 virus (Homsy J. et al., Science 244 (1989) 1357–1360) suggests an important role of these receptors in viral propagation in vivo. The receptor, which has been recently cloned (Simmons D. and Seed B., Nature 333 (1988) 568–570), is mainly located in the membranes of macrophages, polynudear cells and granulocytes, but in contrast to CD4, the CD16 receptor also exists in a soluble state-in serum (Khayat D. et al., J. Immunol. 132 (1984) 2496–2501; Khayat D. et al., J. Immunol. Meth. 100 (1987) 235–241). It should be noted that the membraneous CD16 receptor is used as a second route of entry by the HIV-1 virus to infect macrophages, due to the presence of facilitating antibodies (Homsy J. et al., Science 244 (1989) 1357–1360). This process of infection which involves an "Fc receptor" at the surface of target cells (for example the CD16 receptor), and the Fc region of antibodies directed against the virion, is named ADE ("Antibody Dependent Enhancement"); it has also been described for the flavivirus (Peiris J. S. M. et al., Nature 289 (1981) 189–191) and the Visna-Mædi ovine lentivirus (Jolly P. E. et al., J. Virol. 63 (1989) 1811–1813). Other "Fc receptors" have been described for IgG's (FcγRI and FγRII for example) as well as for other classes of immunoglobulins, and the ADE phenomenon also involves other types of "Fc receptors" such as that recognized by the monoclonal antibody 3G8 (Homsy J. et al., Science 244 (1989) 1357–1360; Takeda A. et al., Science 242 (1988) 580–583). One can thus call into question the efficiency of hybrid antiviral macromolecules which depend uniquely on fusions between immunoglobulins and all or part of a receptor normally used by a virus such as HIV-1 for its propagation in the host; in effect, the presence of a functional Fc fragment on such molecules could actually facilitate viral infection of certain cell types. It is also important to obtain CD4 derivatives that can be used at high therapeutic concentrations.

A different type of chimeric construction involving the bacterial protein MalE and the CD4 molecule has been studied (Clément J. M. et al., C. R. Acad. Sci. Paris 308, series III (1989) 401–406). Such a fusion allows one to take advantage of the properties of the MalE protein, in particular regarding the production and/or purification of the hybrid protein. In addition, the construction of a genetic fusion between the CD4 molecule and a bacterial toxin has also been described (Chaudhary V. K. et al., Nature 335 (1988) 369–372). In these cases, utilization of a genetic fusion involving a bacterial protein for therapy in humans can be questionable.

The discovery of the role of the ADE phenomenon in the propagation of certain viruses, in particular lentiviruses including HIV-1, justifies the search for alternatives to both the development of an anti-AIDS vaccine, and to the development of therapeutic agents based solely on fusions between immunoglobulins and molecules capable of binding the virus. This is why the anti-AIDS therapeutic agents described in the present invention are based on the fusion of all or part of a receptor used directly or indirectly by the HIV-1 virus for its propagation in vivo with a stable plasma protein, devoid of enzymatic activity, and lacking the Fc fragment.

In particular, the present invention concerns the coupling, mainly by genetic engineering, of human albumin variants with a binding site for the HIV-1 virus. Such hybrid macromolecules derived from human serum albumin are characterized by the presence of one or several variants of the CD4 receptor arising from the modification, particularly by in vitro DNA recombination techniques (mutation, deletion, and/or addition), of the N-terminal domain of the CD4 receptor, which is implicated in the specific interaction of the HIV-1 virus with target cells. Such hybrid macromolecules circulating in the plasma represent stable decoys with an antiviral function, and will be designated by the generic term HSA-CD4. Another goal of this invention concerns the coupling of human albumin variants with variants of the CD16 molecule, which is implicated in the internalization of viruses including HIV-1 (to be designated by the generic term HSA-CD16), and in general the coupling of albumin variants with molecules capable of mimicking the cellular receptors responsible for the ADE phenomenon of certain viruses, and in particular the lentiviruses.

The principles of the present invention can also be applied to other receptors used directly or indirectly by a human or animal virus for its propagation in the host organism. For example:

1/ intercellular adhesion molecule 1 (ICAM-1), shown to be the receptor for human rhinovirus HRV14 (Greve J. M. et al., Cell 56 (1989) 839–847; Staunton D. E. et al., Cell 56 (1989) 849–853);

2/ poliovirus receptor, recently cloned by Mendelsohn et al. (Cell 56 (1989) 855–865);

3/ the receptor of complement factor C3D which is the receptor of Epstein-Barr virus (EBV) in human cells (Fingeroth J. D. et al., Proc. Natl. Acad. Sci. USA 81 (1984) 4510–4514), this virus being responsible for infectious mononucleosis and for certain lymphomas in man;

4/ human T cell leukemia virus HTLV-I and HTLV-II receptors, recently mapped to chromosome 17 (Sommerfelt M. A. et al., Science 242 (1988) 1557–1559), these viruses being responsible for adult T cell leukemia as well as for tropical spastic paraparesie (HTLV-I) and tricholeucocytic leukemia (HTLV-II);

5/ the receptor of the ecotropic murine leukemia virus MuLV-E, mapped to chromosome 5 of the mouse by Oie et al. (Nature 274 (1978) 60–62) and recently cloned by Albritton et al. (Cell 57 (1989) 659–666).

Another goal of the present invention concerns the development of stable hybrid macromolecules with an anticancer function, obtained by the coupling of albumin variants with molecules able to bind growth factors which, in certain pathologies associated with the amplification of the corresponding membraneous proto-oncogenes, can interact with their target cells and induce a transformed phenotype. An example of such receptors is the class of receptors with tyrosine kinase activity (Yarden Y. and Ulrich A., Biochemistry 27 (1988) 3113–3119), the best known being the epidermal growth factor (EGF) and the colony stimulating factor I (CSF-I) receptors, respectively coded by the proto-oncogenes c-erbB-1 (Downward J. et al., Nature 307 (1984) 521–527) and c-fms (Sherr C. J. et al., Cell 41 (1985) 665–676). Another example of such receptors includes the human insulin receptor (HIR), the platelet-derived growth factor (PDGF) receptor, the insulin-like growth factor I (IGF-I) receptor, and most notably the proto-oncogene c-erbB-2, whose genomic amplification and/or overexpression was shown to be strictly correlated with certain human cancers, in particular breast cancer (Slamon D. J. et al., Science 235 (1987) 177–182; Kraus M. H. et al., EMBO J. 6 (1987) 605–610). Furthermore, the principles put forth in the present invention can be equally applied to other receptors, for example the interleukin 6 (IL-6) receptor, which has been shown in vitro to be an autocrine factor in renal carcinoma cells (Miki S. et al., FEBS Lett., 250 (1989) 607–610).

As indicated above, the hybrid macromolecules of interest are substantially preferably proteinic and can therefore be generated by the techniques of genetic engineering. The preferred way to obtain these macromolecules is by the culture of cells transformed, transfected, or infected by vectors expressing the macromolecule. In particular, expression vectors capable of transforming yeasts, especially of the genus Kluyveromyces, for the secretion of proteins will be used. Such a system allows for the production of high quantities of the hybrid macromolecule in a mature form, which is secreted into the culture medium, thus facilitating purification.

The preferred method for expression and secretion of the hybrid macromolecules consists therefore of the transformation of yeast of the genus Kluyveromyces by expression vectors derived from the extrachromosomal replicon pKD1, initially isolated from *K. marxianus* var. *drosophilarum*. These yeasts, and in particular *K. marxianus* (including the varieties *lactis, drosophilarum* and *marxianus* which are henceforth designated respectively as *K. lactis, K. drosophilarum* and *K. fragilis*), are generally capable of replicating these vectors in a stable fashion and possess the further advantage of being included in the list of G.R.A.S. ("Generally Recognized As Safe") organisms. The yeasts of particular interest include industrial strains of Kluyveromyces capable of stable replication of said plasmid derived from plasmid pKD1 into which has been inserted a selectable marker as well as an expression cassette permitting the secretion of the given hybrid macromolecule at high levels.

Three types of cloning vectors have been described for Kluyveromyces:

i) Integrating vectors containing sequences homologous to regions of the Kluyveromyces genome and which, after being introduced into the cells, are integrated in the Kluyveromyces chromosomes by in vivo recombination (International patent application WO 83/04050). Integration, a rare event requiring an efficient selection marker, is obtained when these vectors do not contain sequences permitting autonomous replication in the cell. The advantage of this system is the stability of the transformed strains, meaning that they can be grown in a normal nutritive medium without the need for selection pressure to maintain the integrated sequences. The disadvantage, however, is that the integrated genes are present in only a very small number of copies per cell, which frequently results in a low level of production of a heterologous protein.

ii) Replicating vectors containing Autonomously Replicating Sequences (ARS) derived from the chromosomal DNA of Kluyveromyces (Das S. and Hollenberg C. P., Current Genetics 6 (1982) 123–128; International patent application WO 83/04050). However these vectors are of only moderate interest, since their segregation in mitotic cell division is not homogeneous, which results in their loss from the cells at high frequency even under selection pressure.

iii) Replicating vectors derived from naturally occurring yeast plasmids, either from the linear "killer" plasmid k1 isolated from *K. lactis* (de Louvencourt L. et al., J. Bacteriol. 154 (1983) 737–742; European patent application EP 0 095 986 A1, publ. 07,12,1983), or from the circular plasmid pKD1 isolated from *K. drosophilarum* (Chen X. J. et al., Nucl. Acids Res. 14 (1986) 4471–4480; Falcone C. et al., Plasmid 15 (1986) 248–252; European patent application EP 0 241 435 A2, publ. 14,10,1987). The vectors containing replicons derived from the linear "killer" plasmid require a special nutrient medium, and are lost in 40–99% of the cells after only 15 generations, even under selection pressure (European patent application EP 0 095 986 A1, 1983), which limits their use for mass production of heterologous proteins. The vectors derived from plasmid pKD1 described in European patent application EP 0 241 435 A2 are also very unstable since even the most performant vector (P3) is lost in approximately 70% of the cells after only six generations under nonselective growth conditions.

An object of the present invention concerns the utilization of certain plasmid constructions derived from the entire pKD1 plasmid; such constructions possess significantly higher stability characteristics than those mentioned in European patent application EP 0 241 435 A2. It will be shown in the present invention that these new vectors are stably maintained in over 80% of the cells after 50 generations under nonselective growth conditions.

The high stability of the vectors used in the present invention was obtained by exploiting fully the characteristics of plasmid pKD1. Besides an origin of replication, this extrachromosomal replicon system possesses two inverted repeats, each 346 nucleotides in length, and three open reading frames coding for genes A, B, et C, whose expression is crucial for plasmid stability and high copy number. By analogy with the $2\mu$ plasmid of S. cerevisiae, which is structurally related to plasmid pKD1 (Chen X. J. et al., Nucl. Acids Res. 14 (1986) 4471–4480), the proteins encoded by genes B et C are probably involved in plasmid partitioning during mitotic cell division, and may play a role in the negative regulation of gene A which encodes a site-specific recombinase (FLP). It has been shown that the FLP-mediated recombination between the inverted repeats of the $2\mu$ plasmid of S. cerevisiae is the basis of a mechanism of autoregulation of the number of plasmid copies per cell: when copy number becomes too low to permit the production of sufficient quantities of the products of genes B and C, which act as repressors of gene A, the FLP recombinase is induced and the plasmid replicates according to a rolling circle type model, which amplifies copy number to about 50 copies per cell (Futcher A. B., Yeast 4 (1988) 27–40).

The vectors published in European patent application EP 0 241 435 A2 do not possess the above-mentioned structural characteristics of plasmid pKD1 of K. drosophilarum: vector A15 does not carry the complete sequence of pKD1, and vectors P1 and P3 carry an interrupted A gene, thereby destroying the system of autoregulated replication of resident plasmid pKD1. In contrast, the pKD1-derived constructs used in the present invention maintain the structural integrity of the inverted repeats and the open reading frames A, B and C, resulting in a notably higher stability of the plasmid as well as an increased level of secretion of the therapeutically active hybrid macromolecules.

The expression cassette will include a transcription initiation region (promoter) which controls the expression of the gene coding for the hybrid macromolecule. The choice of promoters varies according to the particular host used. These promoters derive from genes of Saccharomyces or Kluyveromyces type yeasts, such as the genes encoding phosphoglycerate kinase (PGK), glyceraldehyde-3-phosphate dehydrogenase (GPD), the lactase of Kluyveromyces (LAC4), the enolases (ENO), the alcohol dehydrogenases (ADH), the acid phosphatase of S. cerevisiae (PHO5), etc. . . . These control regions may be modified, for example by in vitro site-directed mutagenesis, by introduction of additional control elements or synthetic sequences, or by deletions or substitutions of the original control elements. For example, transcription-regulating elements, the so-called "enhancers" of higher eukaryotes and the "upstream activating sequences" (UAS) of yeasts, originating from other yeast promoters such as the GAL1 and GAL10 promoters of S. cerevisiae or the LAC4 promoter of K. lactis, or even the enhancers of genes recognized by viral transactivators such as the E2 transactivator of papillomavirus, can be used to construct hybrid promoters which enable the growth phase of a yeast culture to be separated from the phase of expression of the gene encoding the hybrid macromolecule. The expression cassette used in the present invention also includes a transcription and translation termination region which is functional in the intended host and which is positioned at the 3' end of the sequence coding for the hybrid macromolecule.

The sequence coding for the hybrid macromolecule will be preceded by a signal sequence which serves to direct the proteins into the secretory pathway. This signal sequence can derive from the natural N-terminal region of albumin (the prepro region), or it can be obtained from yeast genes coding for secreted proteins, such as the sexual pheromones or the killer toxins, or it can derive from any sequence known to increase the secretion of the so-called proteins of pharmaceutical interest, including synthetic sequences and all combinations between a "pre" and a "pro" region.

The junction between the signal sequence and the sequence coding for the hybrid macromolecule to be secreted in mature form corresponds to a site of cleavage of a yeast endoprotease, for example a pair of basic amino acids of the type $Lys^{-2}$-$Arg^{-1}$ or $Arg^{-2}$-$Arg^{-1}$ corresponding to the recognition site of the protease coded by the KEX2 gene of S. cerevisiae or the KEX1 gene of K. lactis (Chen X. J. et al., J. Basic Microbiol. 28 (1988) 211–220; Wésolowski-Louvel M. et al., Yeast 4 (1988) 71–81). In fact, the product of the KEX2 gene of S. cerevisiae cleaves the normal "pro" sequence of albumin in vitro but does not cleave the sequence corresponding to the pro-albumin "Christchurch" in which the pair of basic amino acids is mutated to $Arg^{-2}$-$Glu$-$^{-1}$ (Bathurst I. C. et al., Science 235 (1987) 348–350).

In addition to the expression cassette, the vector will include one or several markers enabling the transformed host to be selected. Such markers include the URA3 gene of yeast, or markers conferring resistance to antibiotics such as geneticin (G418), or any other toxic compound such as certain metal ions. These resistance genes will be placed under the control of the appropriate transcription and translation signals allowing for their expression in a given host.

The assembly consisting of the expression cassette and the selectable marker can be used either to directly transform yeast, or can be inserted into an extrachromosomal replicative vector. In the first case, sequences homologous to regions present on the host chromosomes will be preferably fused to the assembly. These sequences will be positioned on each side of the expression cassette and the selectable marker in order to augment the frequency of integration of the assembly into the host chromosome by in vivo recombination. In the case where the expression cassette is inserted into a replicative vector, the preferred replication system for Kluyveromyces is derived from the plasmid pKD1 initially isolated from K. drosophilarum while the preferred replication system for Saccharomyces is derived from the $2\mu$ plasmid. The expression vector can contain all or part of the above replication systems or can combine elements derived from plasmid pKD1 as well as the $2\mu$ plasmid.

When expression in yeasts of the genus Kluyveromyces is desired, the preferred constructions are those which contain the entire sequence of plasmid pKD1. Specifically, preferred constructions are those where the site of insertion of foreign sequences into pKD1 is localized in a 197 bp region lying between the SacI (SstI) site and the MgstII site, or alternatively at the SphI site of this plasmid, which permits high stability of the replication systems in the host cells.

The expression plasmids can also take the form of shuttle vectors between a bacterial host such as *Escherichia coli* and yeasts; in this case an origin of replication and a selectable marker that function in the bacterial host would be required. It is also possible to position restriction sites which are unique on the expression vector such that they flank the bacterial sequences. This allows the bacterial sequences to be eliminated by restriction cleavage, and the vector to be religated prior to transformation of yeast, and this can result in a higher plasmid copy number and enhanced plasmid stability. Certain restriction sites such as 5'-GGCCNNNNNGGCC-3' (SfiI) or 5'-GCGGCCGC-3' (NotI) are particularly convenient since they are very rare in yeasts and are generally absent from an expression plasmid.

The expression vectors constructed as described above are introduced into yeasts according to classical techniques described in the literature. After selection of transformed cells, those cells expressing the hybrid macromolecule of interest are inoculated into an appropriate selective medium and then tested for their capacity to secrete the given protein into the extracellular medium. The harvesting of the protein can be conducted during cell growth for continuous cultures, or at the end of the growth phase for batch cultures. The hybrid proteins which are the subject of the present invention are then purified from the culture supernatant by methods which take into account their molecular characteristics and pharmacological activities.

The present invention also concerns the therapeutic application of the hybrid macromolecules described therein, notably in the treatment and the prevention of AIDS, as well as the cells which are transformed, transfected, or infected by vectors expressing such macromolecules.

The examples which follow as well as the attached figures show some of the characteristics and advantages of the present invention.

DESCRIPTION OF FIGURES

The diagrams of the plasmids shown in the figures are not drawn to scale, and only the restriction sites important for the constructions are indicated.

FIG. 2: Nucleotide sequence of the MstII-SmaI restriction fragment including the V1 and V2 domains of the CD4 receptor of the HIV-1 virus. The recognition sites for MstII, HindIII and SmaI are underlined.

FIG. 8: Nucleotide sequence of restriction fragment HindIII coding for the protein fusion prepro-HSA-V1V2. Black arrows indicate the end of the "pre" and "pro" regions of HSA. The MstII site is underlined.

FIG. 18: Characterization of the material secreted after 4 days in culture by strain MW98-8C transformed by plasmids pYG221B (prepro-HSA) and pYG308B (prepro-HSA-V1V2). A, Coomassie staining after electrophoretic migration in an 8.5% polyacrylamide gel. Molecular weight standards (lane 1); supernatant equivalent to 300 $\mu$l of the culture transformed by plasmid pYG308B (lane 2); supernatant equivalent to 100 $\mu$l of the culture transformed by plasmid pYG221B (lane 3); 500 ng of HSA (lane 4). B, immunologic characterization of the secreted material subject to electrophoretic migration in an 8.5% polyacrylamide gel, followed by transfer to a nitrocellulose membrane and utilization of primary antibodies directed against human albumin: 250 ng of HSA standard (lane 1); supernatant equivalent to 100 $\mu$l of the culture transformed by plasmid pYG308B (lane 2); supernatant equivalent to 10 $\mu$l of the culture transformed by plasmid pYG221B (lane 3). C, exactly as in B except that polyclonal antibodies directed against the CD4 molecule were used in place of antibodies directed against HSA.

FIG. 35: Secretion in strain MW98-8C of truncated HSA variants coupled to the V1V2 domains of the CD4 receptor. Panel 1: Coomassie blue staining. Each lane was loaded with the equivalent of 400 µl of culture supernatant from the early stationary phase. Molecular weight markers (lane a), strain transformed by control vector pKan707 (lane b), HSA standard (lane c), strain transformed by expression plasmids pYG308B (HSA$_{585}$-V1V2, lane d), pYG334B (HSA$_{312}$-V1V2, lane e), and pYG335B (HSA$_{300}$-V1V2, lane f).

Panel 2: Western Blot detection using rabbit polyclonal anti-HSA. Each lane was loaded with the equivalent of 100 µl of culture supernatant from the early stationary phase. Biotinylated molecular weight markers (Bio-Rad, lane a), strain transformed by control vector pKan707 (lane b), HSA standard (lane f), strain transformed by expression plasmids pYG308B (HSA$_{585}$-V1V2, lane c), pYG334B (HSA$_{312}$-V1V2, lane d), and pYG335B (HSA$_{300}$-V1V2, lane e). Panel 3: Western Blot detection using a rabbit polyclonal anti-CD4 serum; same legend as in Panel 2.

Figure 36:
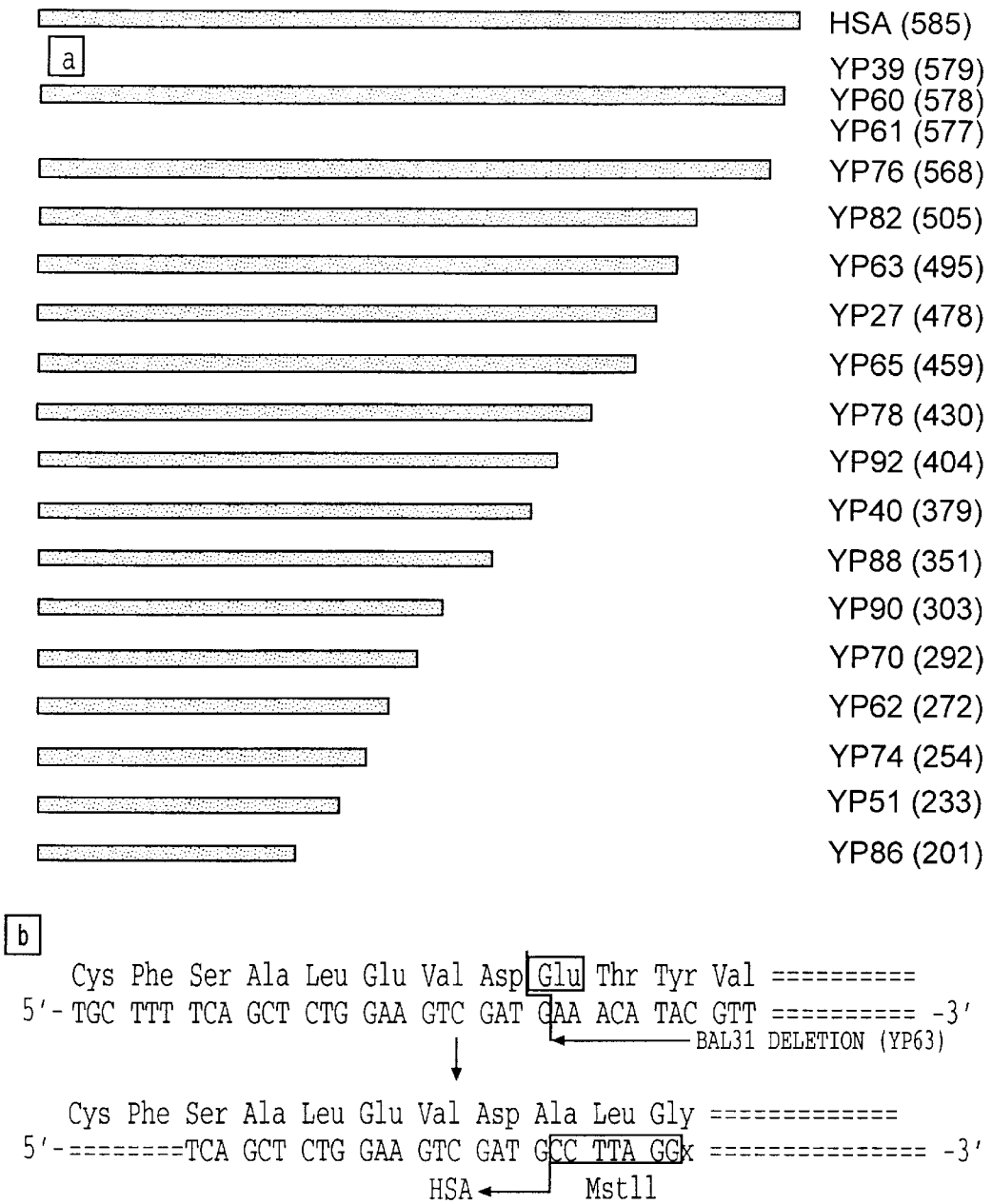

FIG. 36: Panel a: representation of several HindIII (-25)-MstII restriction fragments corresponding to deletions in HSA. Amino add position (numbered according to mature HSA) is indicated in parentheses. Panel b: detail of the position of the MstII site in one of the deletants (clone YP63, linker insertion at amino acid 495).

FIG. 37: Examples of the hinge regions between the HSA and CD4 moieties. The amino add pairs that are potential targets of endoproteases involved in the secretory pathway are boxed. Panel 1: hinge region of protein HSA$_{585}$-CD4. Panel 2: hinge region of HSA$_{Bal31}$-CD4 proteins obtained by Bal31 deletion of the C-terminal portion of HSA (in this representation the Lys—Lys pairs situated at the beginning of the CD4 moiety have been modified by site-directed mutagenesis as exemplified in E.13.2.). Panel 3: hinge region obtained by insertion of a polypeptide (shown here a fragment of troponin C), obtained after site-directed mutagenesis using oligodeoxynucleotide Sq1445. Panel 4: general structure of the hinge region between the HSA and CD4 moieties.

FIG. 38: Panel 1: structure of the in-frame fusion between the prepro region of HSA and the CD4 receptor, present notably in expression plasmids pYG373B, pYG380B, pYG381B and pYG560. Panel 1a: the amino acid pairs that are potential targets of endoproteases involved in the secretory pathway are boxed. Panel 1b: These amino add pairs can be modified by mutating the second lysine of each pair such that the pair is no longer a target for such endoproteases. Panel 2: Examples of hinge regions between the CD4 and HSA moieties present notably in hybrid proteins V1-HSA (panel 2a) or V1V2-HSA (panels 2b and 2c). Panel 3: general structure of the hinge region between the CD4 and HSA moieties.

EXAMPLES

General Cloning Techniques.

The classical methods of molecular biology such as preparative extractions of plasmid DNA, the centrifugation of plasmid DNA in cesium chloride gradients, agarose and polyacrylamide gel electrophoresis, the purification of DNA fragments by electroelution, the extraction of proteins by phenol or phenol/chloroform, the precipitation of DNA in the presence of salt by ethanol or isopropanol, transformation of Escherichia coli etc. . . have been abundantly described in the literature (Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987), and will not be reiterated here.

Restriction enzymes are furnished by New England Biolabs (Biolabs), Bethesda Research Laboratories (BRL) or Amersham and are used according to the recommendations of the manufacturer.

Plasmids pBR322, pUC8, pUC19 and the phages M13mp8 and M13mp18 are of commercial origin (Bethesda Research Laboratories).

For ligations, the DNA fragments are separated by size on agarose (generally 0.8%) or polyacrylamide (generally 10%) gels, purified by electroelution, extracted with phenol or phenol/chloroform, precipitated with ethanol and then incubated in the presence of T4 DNA ligase (Biolabs) according to the recommendations of the manufacturer.

Filling in of 5' ends is carried out using the Klenow fragment of E. coli DNA polymerase I (Biolabs) according to manufacturer recommendations. Destruction of 3' protruding termini is performed in the presence of T4 DNA polymerase (Biolabs) as recommended by the manufacturer. Digestion of 5' protruding ends is accomplished by limited treatment with S1 nuclease.

In vitro site-directed mutagenesis is performed according to the method developed by Taylor et al. (Nucleic Acids Res. 13 (1985) 8749–8764) using the kit distributed by Amersham.

Enzymatic amplification of DNA fragments by the PCR technique (Polymerase-catalyzed Chain Reaction, Saiki R. K. et al., Science 230 (1985) 1350–1354; Mullis K. B. and Faloona F. A., Meth. Enzym. 155 (1987) 335–350) is carried out on a "DNA thermal cycler" (Perkin Elmer Cetus) according to manufacturer specifications.

Nucleotide sequencing is performed according to the method developed by Sanger et al. (Proc. Natl. Acad. Sci. USA, 74 (1977) 5463–5467), using the Amersham kit.

Transformation of *K. lactis* with foreign DNA as well as the purification of plasmid DNA from *K. lactis* are described in the text.

Unless indicated otherwise, the bacterial strains used are *E. coli* MC1060 (lacIPOZYA, X74, galU, galK, $strA^r$), or *E. coli* TG1 (lac, pro A,B, supE, thi, hsdD5/F'traD36, $proA^+B^+$, $laci^q$, LacZ, M15).

All yeast strains used are members of the family of budding yeasts and in particular of the genus Kluyveromyces. Examples of these yeasts are given in the text. The *K. lactis* strain MW98-8C (α, uraA arg, lys, $K^+$, pKD1°) was often used; a sample of this strain has been deposited on Sep. 16, 1988 at the Centraalbureau voor Schimmelkulturen (CBS) at Baarn (Netherlands) under the registration number CBS 579.88.

Example 1

CONSTRUCTION OF A MSTII/HINDIII-SMAI RESTRICTION FRAGMENT CARRYING THE V1V2 DOMAINS OF THE RECEPTOR OF THE HIV-1 VIRUS

An MstII-SmaI restriction fragment corresponding to the V1V2 domains (where V1 and V2 designate the first two N-terminal domains of the CD4 molecule) was generated by the technique of enzymatic amplification (PCR) according to the following strategy: the lymphoblastic cell line CEM13, which expresses high quantities of CD4 receptor, was used as the source of messenger RNAs coding for the receptor. Total RNA was first purified from $3\times10^8$ cells of this line by extraction with guanidium thiocyanate as originally described by Cathala et al. (DNA 4 (1983) 329–335); 50 μg of RNA prepared in this manner then served as matrix for the synthesis of complementary DNA (cDNA) using the Amersham kit and the oligodeoxynucleotide Xol27 as primer (FIG. 1). The resulting cDNA was subjected to 30 cycles of enzymatic amplification by the PCR technique at a hybridization temperature of 62° C., using 1 μg each of oligodeoxynucleotides Xol26 and Xol27 as primer, as shown in FIG. 1. The amplified fragment was directly cloned into the SmaI site of M13mp8 which had been previously dephosphorylated, to generate vector M13/CD4. This vector is an intermediate construction containing the restriction fragment MstII-SmaI which itself is the source of the MstII-HindIII fragment carrying the V1V2 domains of the CD4 molecule; the nucleotide sequence of this fragment is shown in FIG. 2.

Example 2

CONSTRUCTION OF THE EXPRESSION CASSETTE FOR PREPRO-HSA

E.2.1. Construction of plasmid pXL869 coding for prepro-HSA.

The NdeI site of plasmid pXL322 (Latta M. et al., Bio/Technology 5 (1987) 1309–1314) including the ATG translation initiation codon of prepro-HSA was changed to a HindIII site by oligodeoxynucleotide-directed mutagenesis using the following strategy: the HindIII-BglI fragment of pXL322 containing the 5' extremity of the prepro-HSA gene was cloned into vector M13mp18 and mutagenized with oligodeoxynucleotide 5'-ATCTAAGGAAATACAAGCTT-ATGAAGTGGGT-3' (the HindIII site is underlined and the ATG codon of prepro-HSA is shown in bold type); the phage obtained after this mutagenesis step is plasmid pXL855 whose restriction map is shown in FIG. 3. After verification of the nucleotide sequence, the complete coding sequence for prepro-HSA was reconstituted by ligation of the HindIII-PvuII fragment derived from the replicative form of the mutagenized phage and coding for the N-terminal region of prepro-HSA, with the PvuII-HindIII fragment of plasmid pXL322 containing the C-terminal of HSA, thereby generating a HindIII fragment coding the entire prepro-HSA gene. This HindIII fragment, which also contains a 61 bp non-translated region at its 3' extremity, was cloned into the corresponding site of plasmid pUC8 to generate plasmid pXL869 (FIG. 3).

E2.2. Construction of expression cassettes for prepro-HSA expressed under the control of the PGK promoter of *S. cerevisiae.*

Plasmid pYG12 contains a 1.9 kb SalI-BamHI restriction fragment carrying the promoter region (1.5 kb) and terminator region (0.4 kb) of the PGK gene of *S. cerevisiae* (FIG. 4). This fragment is derived from a genomic HindIII fragment (Mellor J. et al., Gene 24 (1983) 1–14) from which a 1.2 kb fragment corresponding to the structural gene has been deleted, comprising a region between the ATG translation initiation codon and the BglII site situated 30 codons upstream of the TAA translation termination codon. The HindIII sites flanking the 1.9 kb fragment were then destroyed using synthetic oligodeoxynucleotides and replaced by a SalI and a BamHI site respectively upstream of the promoter region and downstream of the transcription terminator of the PGK gene. A unique HindIII site was then introduced by site-directed mutagenesis at the junction of the promoter and terminator regions; the sequence flanking this unique HindIII site (shown in bold letters) is as follows:

5'-TAAAAACAAAAGATCCCCAAGCTTGGG-
GATCTCCCATGTCTCTACT-3'

Plasmid pYG208 is an intermediate construction generated by insertion of the synthetic adaptor BamHI/SalI/BamHI (5'-GATCCGTCGACG-3') into the unique BamHI site of plasmid pYG12; plasmid pYG208 thereby allows the removal of the promoter and terminator of the PGK gene of *S. cerevisiae* in the form of a SalI restriction fragment (FIG. 4).

The HindIII fragment coding for prepro-HSA was purified from plasmid pXL869 by electroelution and cloned in the "proper" orientation (defined as the orientation which places the N-terminal of the albumin prepro region just downstream of the PGK promoter) into the HindIII site of plasmid pYG208 to generate plasmid pYG210. As indicated in FIG. 4, plasmid pYG210 is the source of a SalI restriction fragment carrying the expression cassette (PGK promoter/prepro-HSA/PGK terminator).

E.2.3. Optimization of the expression cassette.

The nucleotide sequence located immediately upstream of the ATG translation initiation codon of highly expressed genes possesses structural characteristics compatible with such high levels of expression (Kozak M., Microbiol. Rev. 47 (1983) 145; Hamilton R. et al., Nucl. Acid Res. 15 (1987) 3581–3593). The introduction of a HindIII site by site-directed mutagenesis at position-25 (relative to the ATG initiation codon) of the PGK promoter of S. cerevisiae is described in European patent application EP N° 89 10480.

In addition, the utilization of oligodeoxynucleotides Sq451 and Sq452 which form a HindIII-BstEII adaptor is described in the same document and permits the generation of a HindIII restriction fragment composed of the 21 nucleotides preceding the ATG initiator codon of the PGK gene, followed by the gene coding for prepro-HSA. The nucleotide sequence preceding the ATG codon of such an expression cassette is as follows (the nucleotide sequence present in the PGK promoter of S. cerevisiae is underlined):

5'-AAGCTTTACAACAAATATAAAAACAATG-3'.

Example 3

IN-FRAME FUSION OF PREPRO-HSA WITH THE V1V2 DOMAINS OF THE CD4 RECEPTOR

Figure 1:
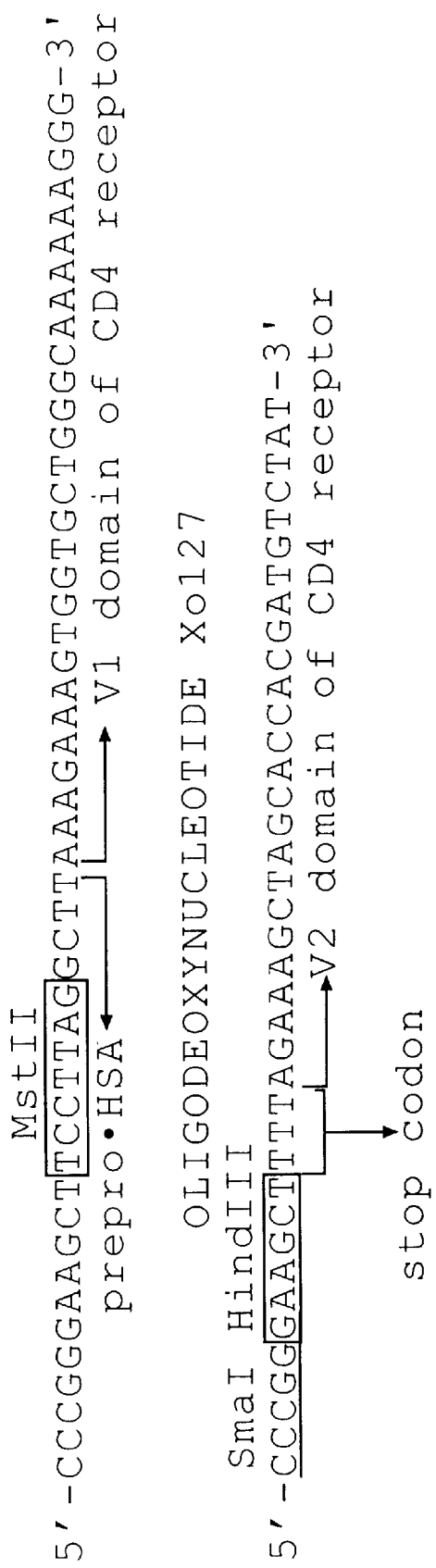
FIG. 1: Oligodeoxynucleotides used to generate the MstII and HindIII-SmaI restriction sites, situated respectively upstream and downstream of the V1V2 domains of the CD4 molecule.
Figure 3:
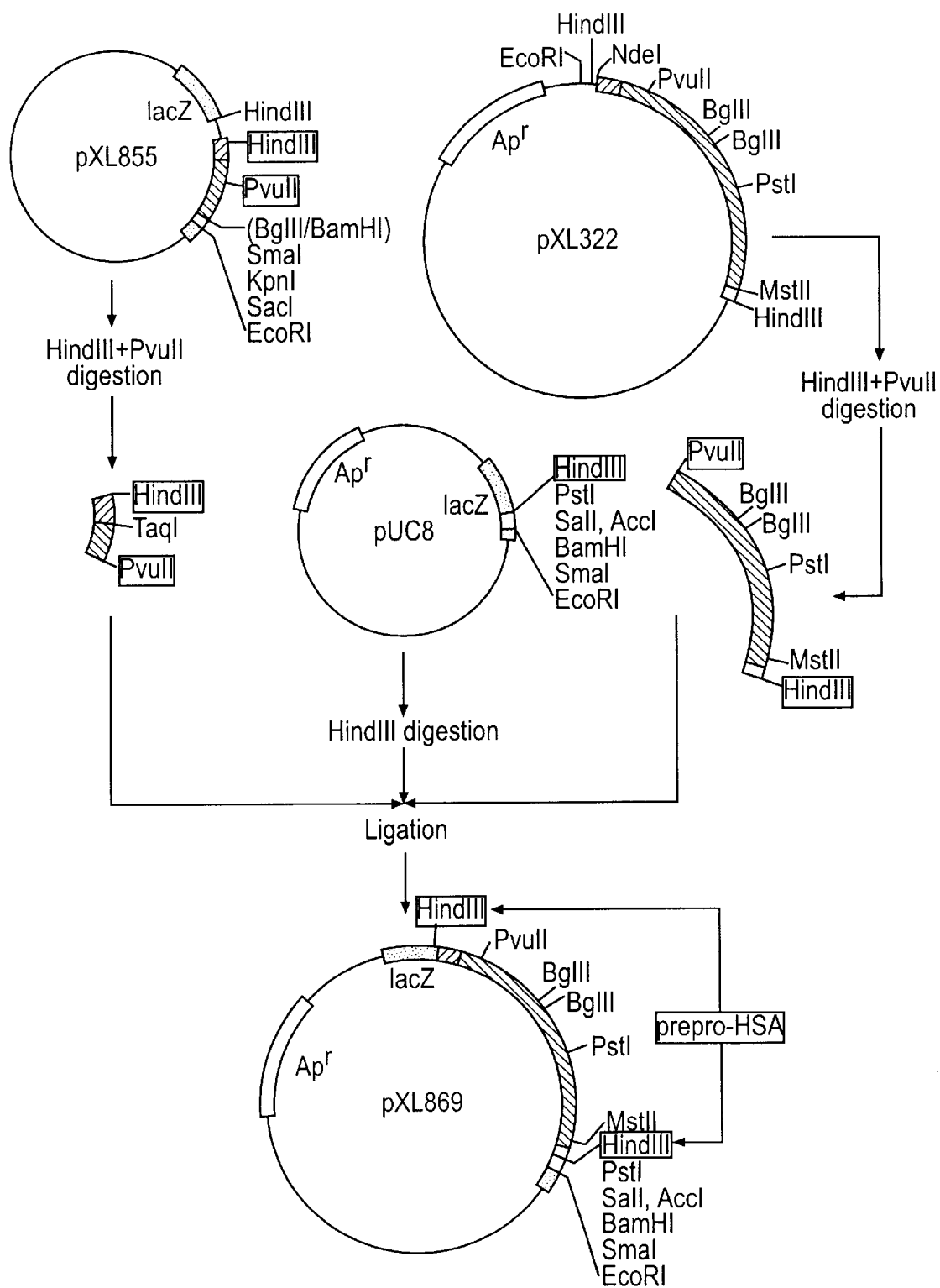
FIG. 3: Construction of plasmid pXL869 coding for prepro-HSA.
Figure 4:
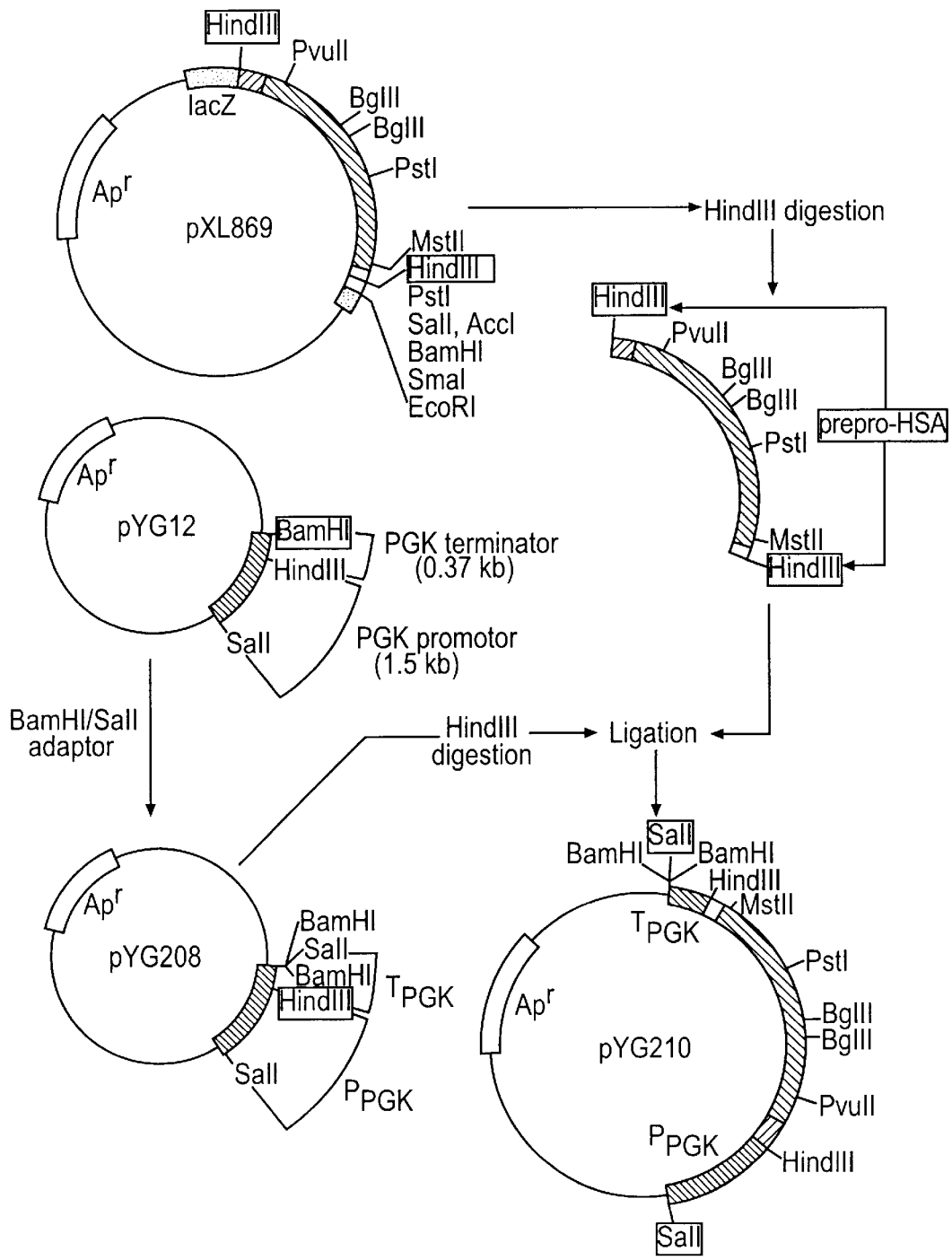
FIG. 4: Construction of plasmids pYG208 and pYG210.
Figure 5:
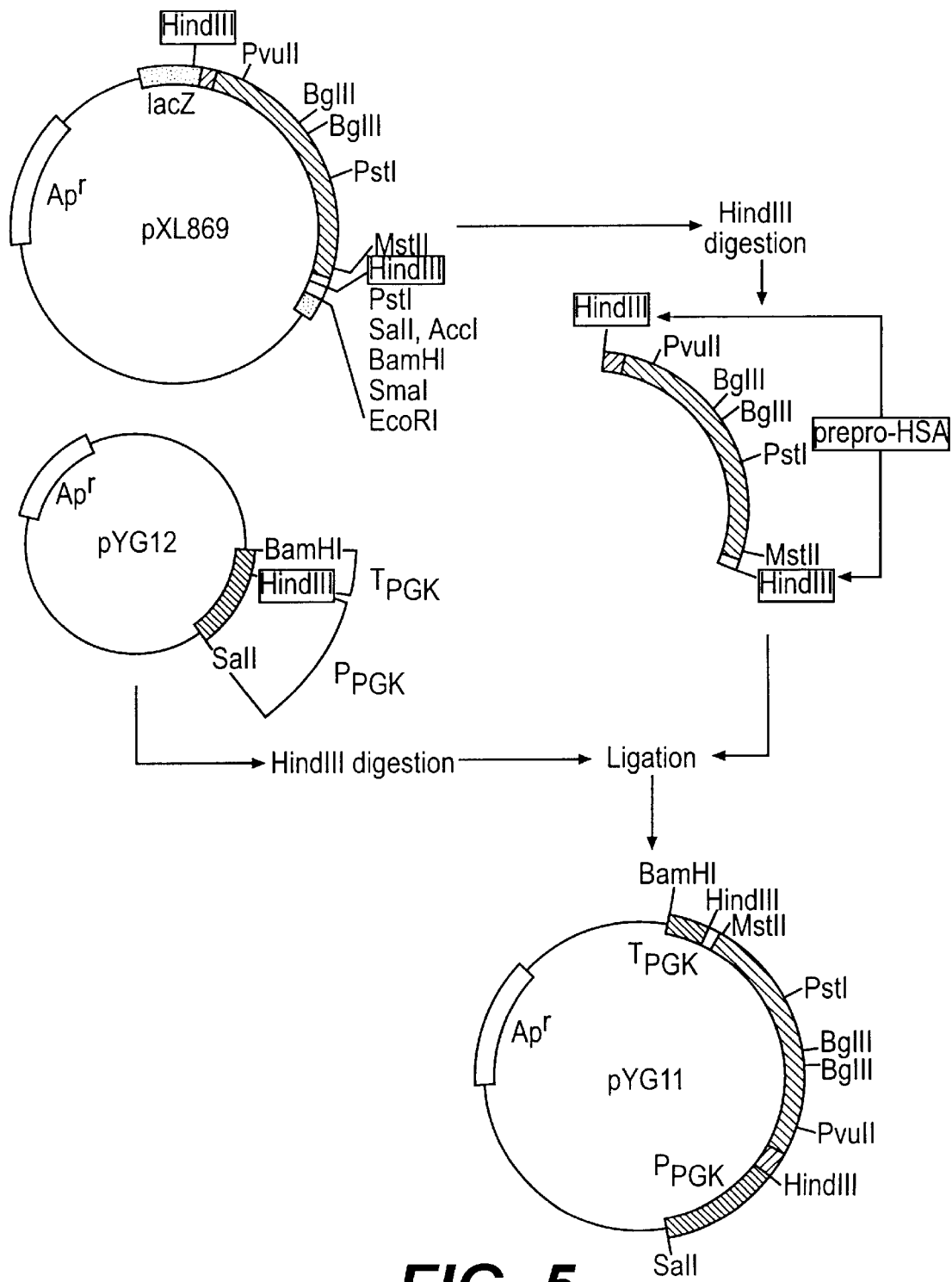
FIG. 5: Construction of plasmid pYG11.
Figure 6:
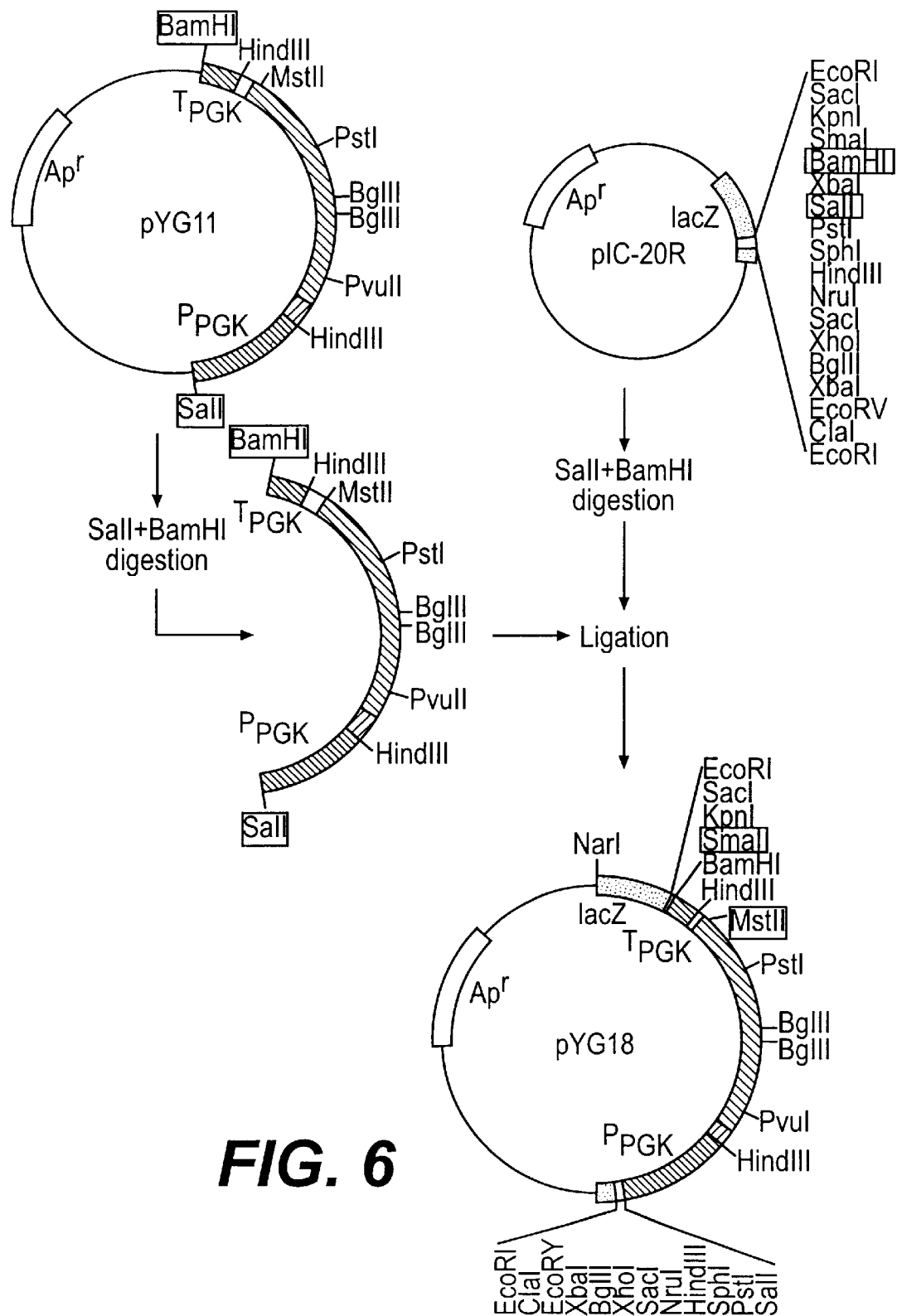
FIG. 6: Construction of plasmid pYG18.

The cloning strategy used for the in-frame construction of the hybrid molecule prepro-HSA-V1V2 is illustrated in FIGS. 5 through 9. Plasmid pYG11is an intermediate construction in which the HindIII fragment coding for prepro-HSA has been purified from plasmid pXL869 and cloned into the HindIII site of plasmid pYG12 (FIG. 5). The construction of plasmid pYG18 is represented in FIG. 6; this plasmid corresponds to the SalI-BamHI fragment coding for the expression cassette (PGK promoter/prepro-HSA/PGK terminator) purified from plasmid pYG11 and cloned into the corresponding sites of plasmid pIC20R (Marsh F. et al., Gene 32 (1984) 481–485).

Figure 7:
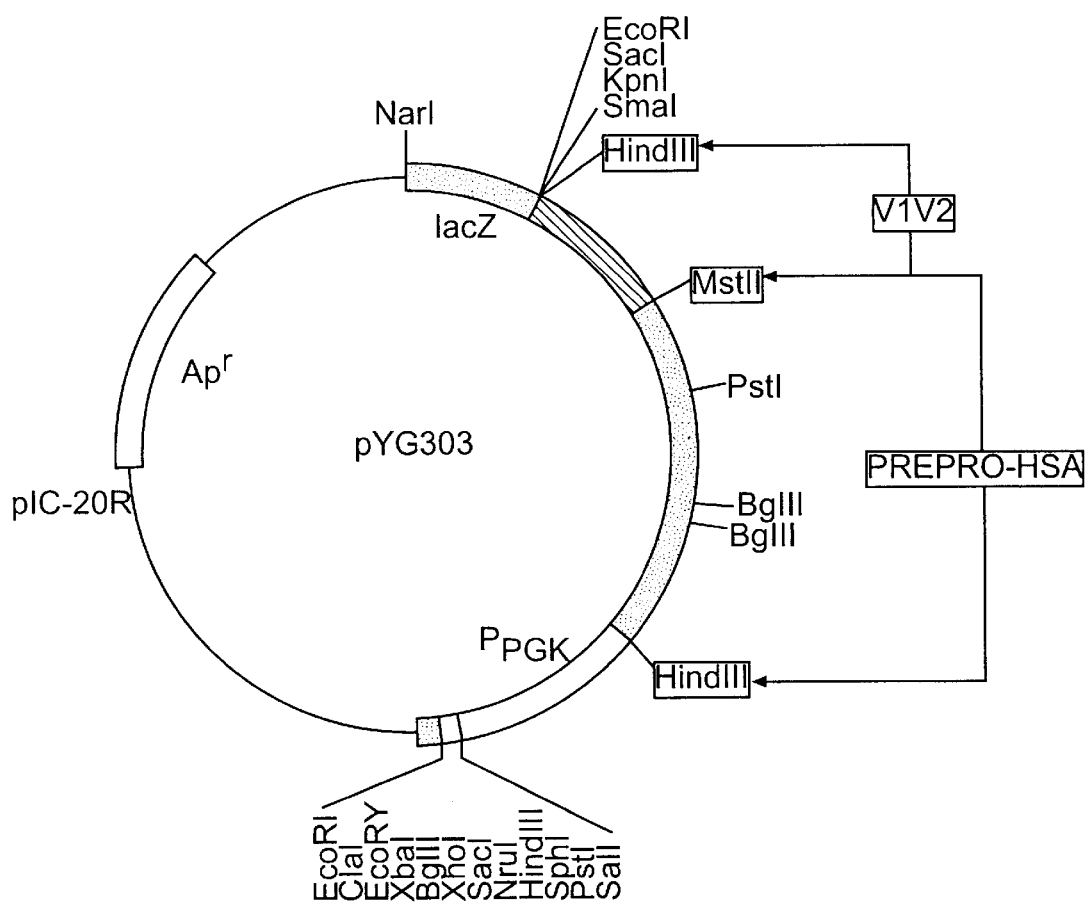
FIG. 7: Restriction map of plasmid pYG303.
Figure 9:
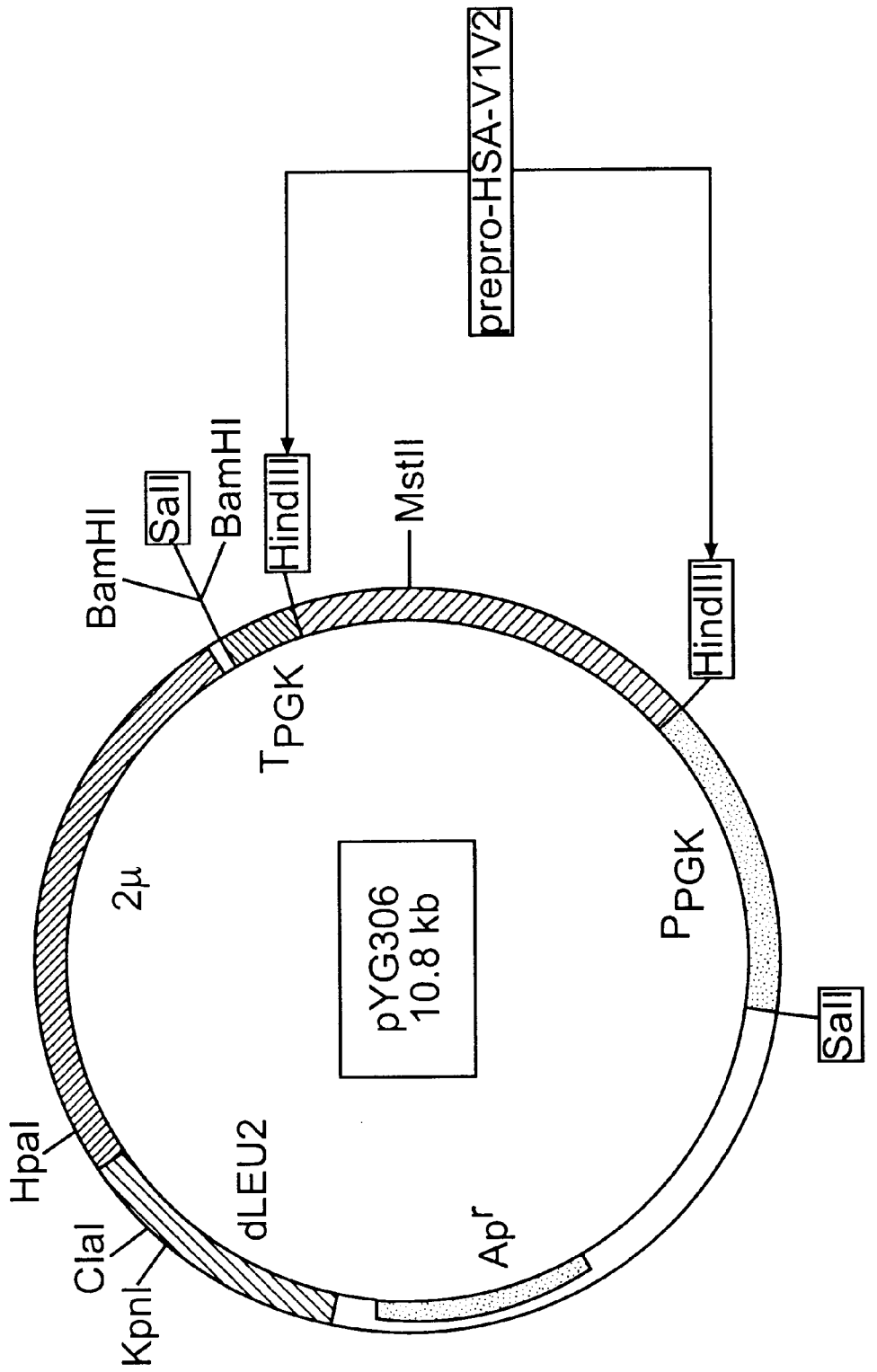
FIG. 9: Restriction map of plasmid pYG306.

The MstII-SmaI restriction fragment carrying the V1V2 domains of the CD4 receptor, obtained as described in Example 1, was cloned into plasmid pYG18 cut by the same enzymes to generate recombinant plasmid pYG303 whose restriction map is shown in FIG. 7. Plasmid pYG303 therefore carries a HindIII fragment corresponding to the in-frame fusion of the entire prepro-HSA gene followed by the V1V2 domains of the CD4 receptor; FIG. 8 shows the nucleotide sequence of this fragment. This fragment was then cloned into the HindIII site of plasmid pYG208: insertion of this fragment, which codes for the gene prepro HSA-V1V2, in the proper orientation into plasmid pYG208, generates plasmid pYG306 whose restriction map is shown in FIG. 9. Plasmid pYG306 carries a SalI restriction fragment containing the expression cassette (PGK promoter/prepro-HSA-V1V2/PGK terminator).

Example 4

CONSTRUCTION OF STABLE CLONING VECTORS DERIVED FROM REPLICON pKD1

E.4.1. Isolation and purification of plasmid pKD1.

Plasmid pKD1 was purified from K. drosophilarum strain UCD 51–130 (U.C.D. collection, University of California, Davis, Calif. 95616) according to the following protocol: a 1 liter culture in YPD medium (1% yeast extract, 2% Bacto-peptone, 2% glucose) was centrifuged, washed, and resuspended in a solution of 1.2 M sorbitol, and cells were transformed into spheroplasts in the presence of zymolyase (300 μg/ml), 25 mM EDTA, 50 mM phosphate and β-mercaptoethanol (1 μg/ml). After washing in a solution of 1.2 M sorbitol, spheroplasts corresponding to 250 ml of the original culture were resuspended in 2.5 ml of 1.2 M sorbitol to which was added the same volume of buffer (25 mM Tris-HCl, pH 8,0; 50 mM glucose; 10 mM EDTA). The following steps correspond to the alkaline lysis protocol already described (Birnboim H. C. and Doly J. C., Nucleic Acids Res. 7 (1979) 1513–1523). DNA was purified by isopycnic centrifugation in a cesium chloride gradient.

E.4.2. Construction of plasmid pCXJ1.

Figure 10:
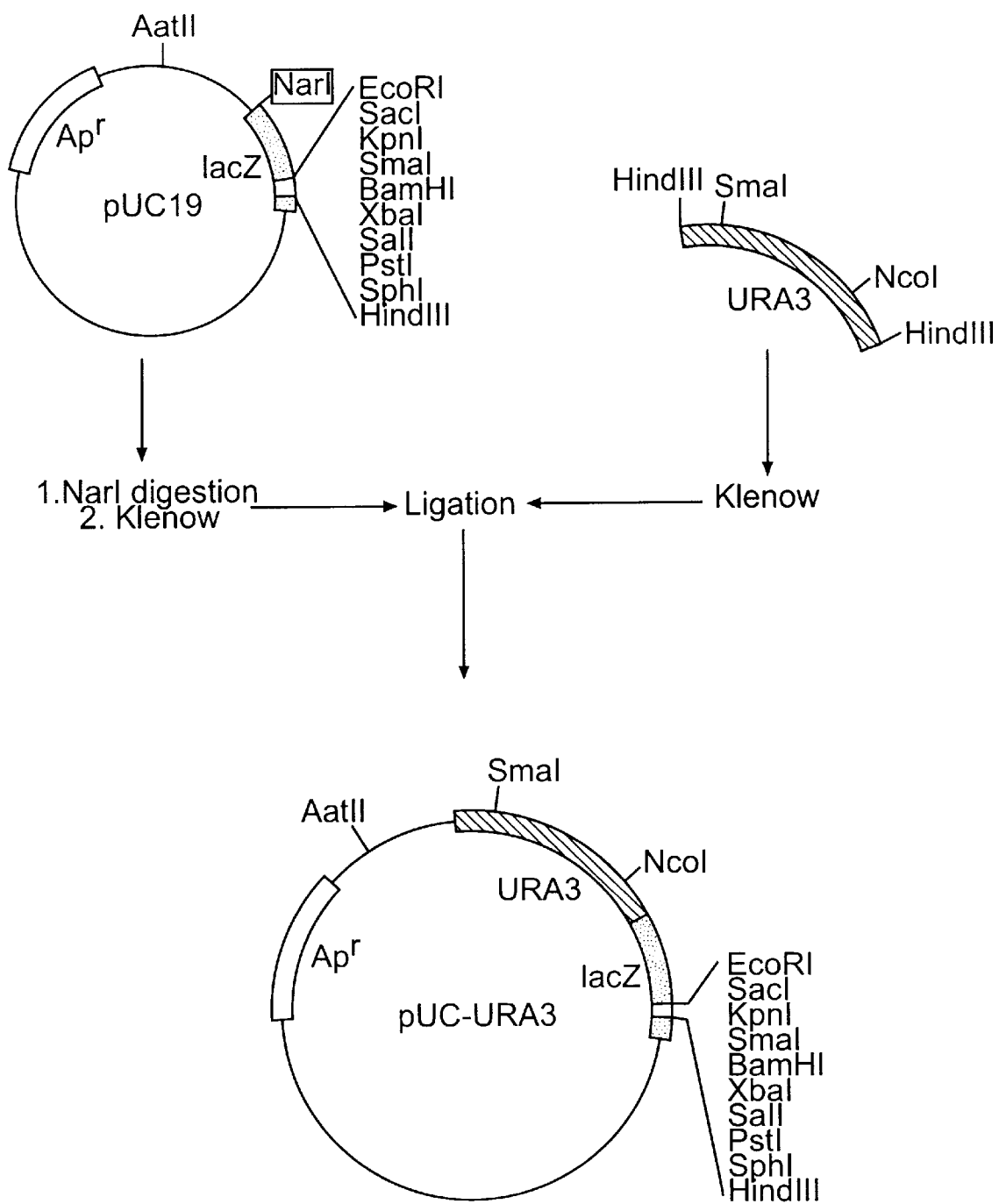
FIG. 10: Construction of plasmid pUC-URA3.

The intermediate construction pUC-URA3 (FIG. 10) consists of a 1.1 kb fragment containing the URA3 gene of S. cerevisiae inserted in the unique NarI site of plasmid pUC19 as follows: the HindIII fragment coding for the URA3 gene was purified by HindIII digestion of plasmid pG63 (Gerbaud C. et al., Curr. Genet. 3 (1981) 173–180); the fragment was treated with the Klenow fragment of E. coli DNA polymerase I to generate blunt ends, purified by electroelution, and inserted into plasmid pUC19 which had been cleaved by NarI and treated with the Klenow fragment of E. coli DNA polymerase I.

Figure 11:
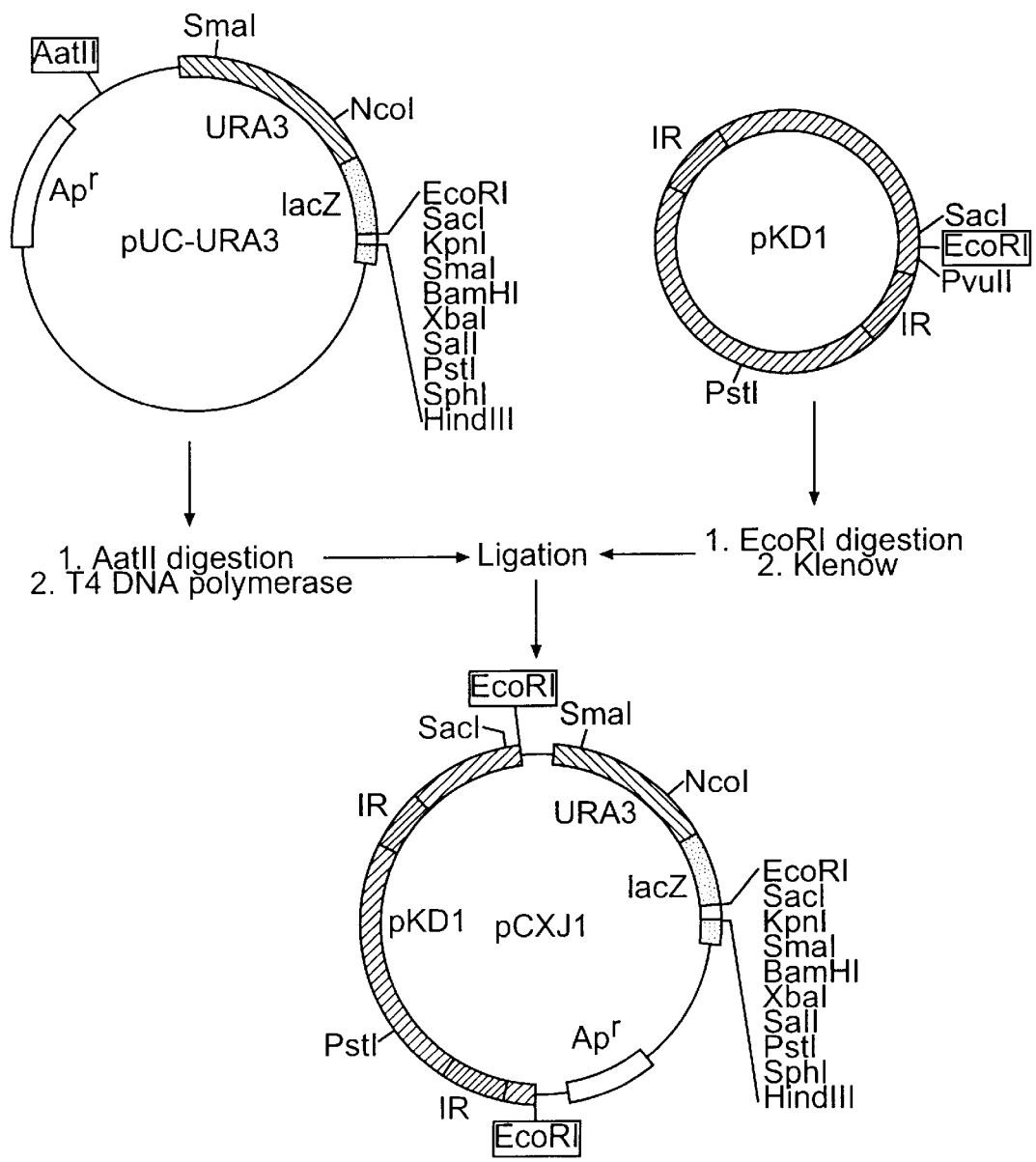
FIG. 11: Construction of plasmid pCXJ1.

Plasmid pCXJ1 (FIG. 11) contains the complete sequence of plasmid pKD1 inserted into the unique AatII site of pUC-URA3 as follows: plasmid pKD1 was linearized by cleavage with EcoRI, then blunt-ended with the Klenow fragment of E. coli DNA polymerase I. This fragment was then ligated with plasmid pUC-URA3 which had been cut by AatII and blunt-ended with T4 DNA polymerase: cloning of a blunt-ended EcoRI fragment into a blunt-ended AatII site reconstitutes two EcoRI sites. It should be noted that linearization of plasmid pKD1 at the EcoRI site does not inactivate any of the genes necessary for plasmid stability and copy number, since the EcoRI site is located outside of genes A, B, and C, and outside of the inverted repeats of pKD1. In fact, plasmid pCXJ1 transforms K. lactis uraA cir° at high frequency, is amplified to 70–100 copies per cell, and is maintained in a stable fashion in the absence of selection pressure. Due to the origin of replication carried by plasmid pUC-URA3, plasmid pCXJ1 can also replicate in E. coli, and thus constitutes a particularly useful shuttle vector between E. coli and several yeasts of the genus Kluyveromyces, in particular K. lactis, K. fragilis and K. drosophilarum. However, the utilization of pCXJ1 as a vector for the transformation of Kluyveromyces remains limited to those auxotrophic strains carrying a chromosomal uraA mutation.

E.4.3. Construction of an in-frame fusion between ORF1 of the killer plasmid of K. lactis and the product of the bacterial gene aph[3']-I of transposon Tn903.

Plasmid pKan707 was constructed as a vector to be used in wild type yeasts. This plasmid was generated by insertion of the aph[3']-I gene of bacterial transposon Tn903 coding for 3'-aminoglycoside phosphotransferase (APH), expressed under control of a yeast promoter, into the SalI of plasmid pCXJ1.

Figure 12:
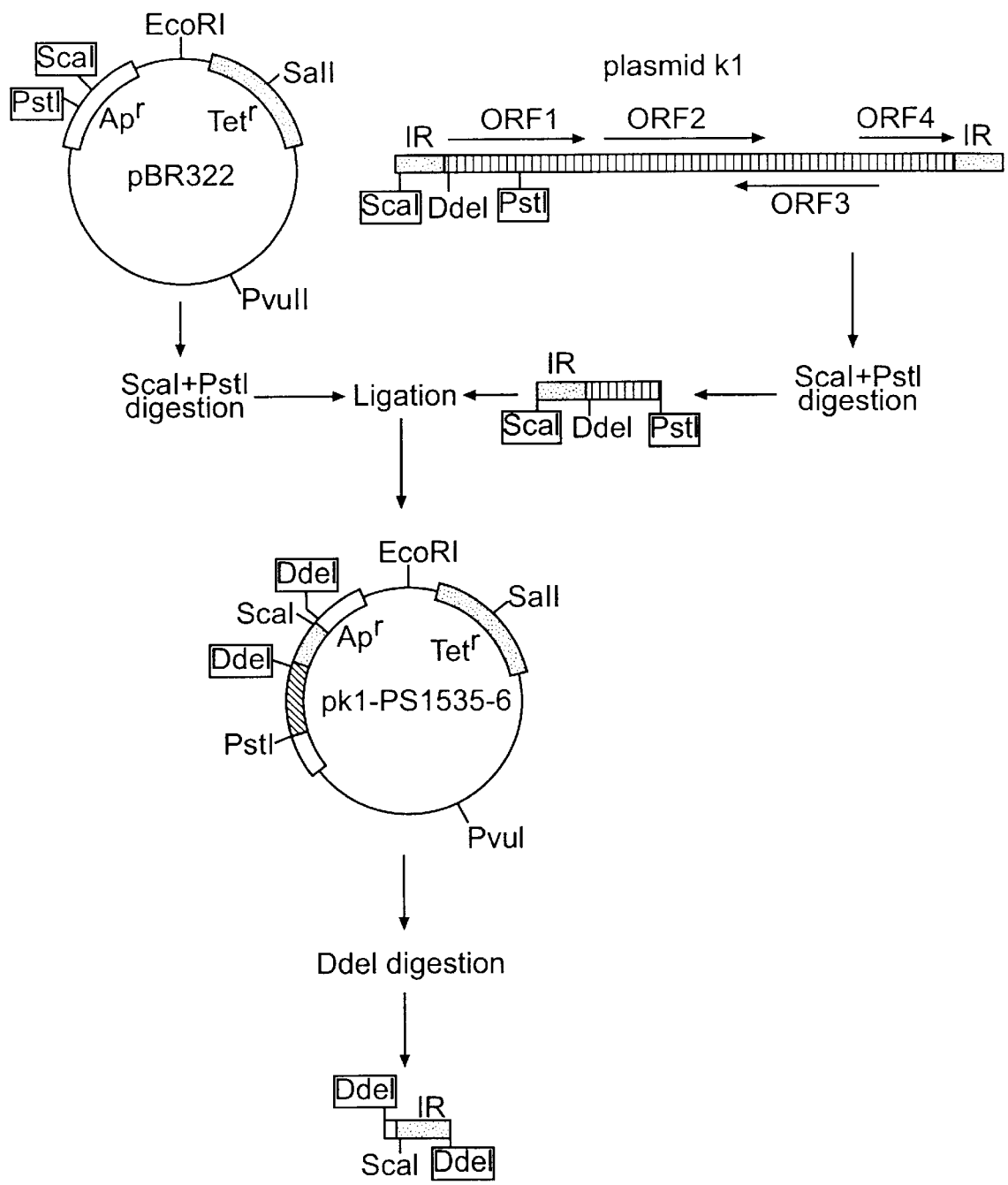
FIG. 12: Construction of plasmid pk1-PS1535-6.

In the first step, the bacterial transcription signals of the aph[3']-I gene were replaced by the $P_{k1}$ promoter isolated from the killer plasmid k1 of K. lactis as follows: the 1.5 kb ScaI-PstI fragment of plasmid k1 was cloned into the corresponding sites of vector pBR322, to generate plasmid pk1-PS1535-6 (FIG. 12); this 1.5 kb fragment contains the 5' region of the first open reading frame (ORF1) carried by plasmid k1 as well as approximately 220 bp upstream (Sor F. and Fukuhara H., Curr. Genet. 9 (1985) 147–155). The purified ScaI-PstI fragment probably contains the entire promoter region of ORF1, since the ScaI site is situated only 22 nucleotides from the extremity of plasmid k1 (Sor F. and al., Nucl. Acids. Res. 11 (1983) 5037–5044). Digestion of pk1-PS1535–6 by DdeI generates a 266 bp fragment containing 17 bp from pBR322 at the extremity close to the ScaI site, and the first 11 codons of ORF1 at the other extremity.

Figure 13:
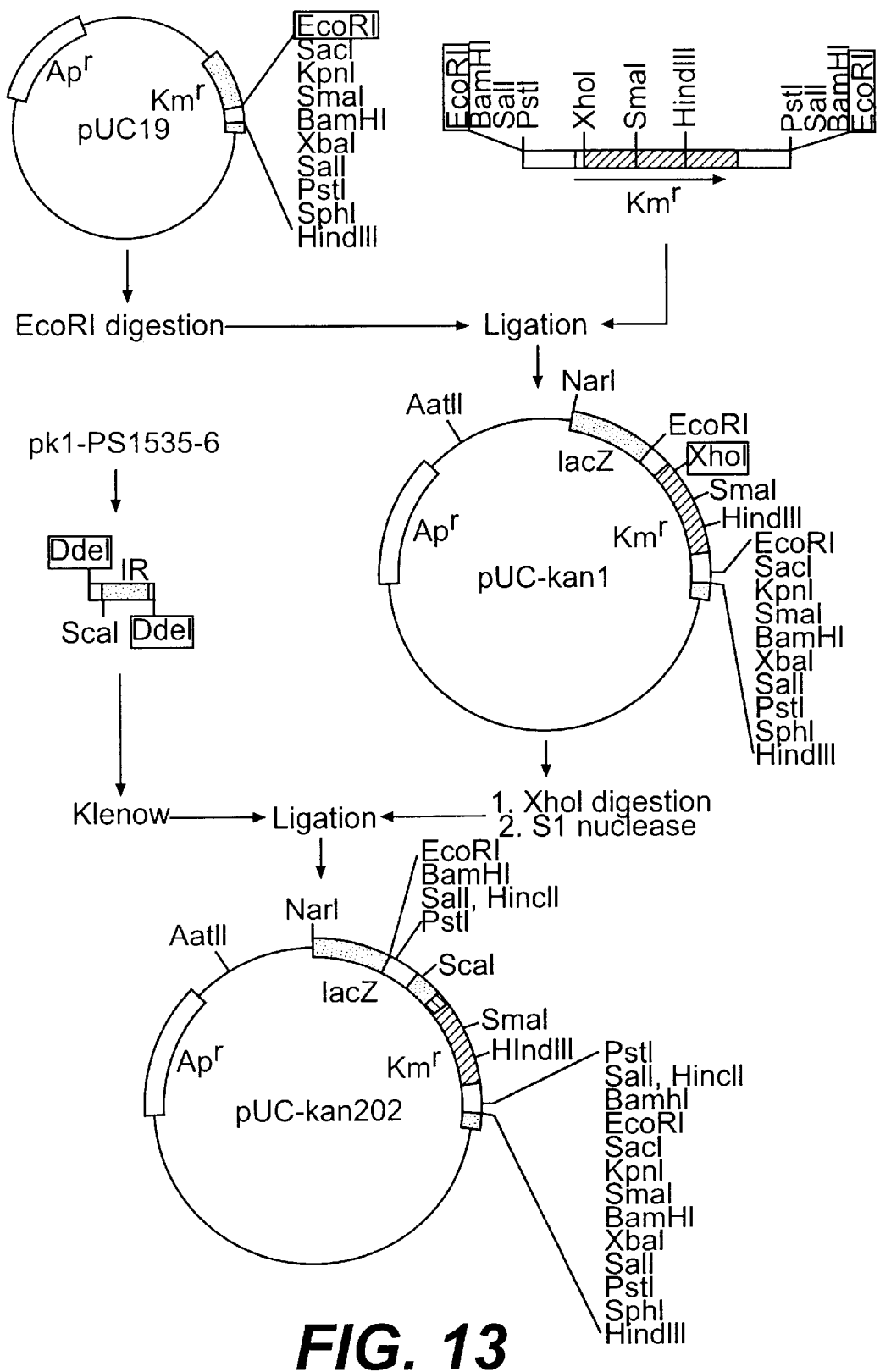
FIG. 13: Construction of plasmids pUC-kan1 and pUC-kan202.

Plasmid pUC-kan1 is an intermediate construction obtained by insertion of the 1.25 kb EcoRI fragment carrying the aph[3']-I gene of Tn903 (Kanamycin Resistance Gene Block TM, Pharmacia), into the EcoRI site of plasmid pUC19 (FIG. 13). The 266 bp DdeI fragment from plasmid pk1-PS1535–6 was treated with the Klenow fragment of *E. coli* DNA polymerase I, purified by electroelution on a polyacrylamide gel, then inserted into the XhoI site of plasmid pUC-kan1 treated by S1 nuclease to generate blunt ends; this generated plasmid pUC-kan202 (FIG. 13). This cloning strategy creates an in-frame fusion of the ORF1 gene of plasmid k1 with the N-terminal extremity of the aph[3']-I gene of Tn903: in the fusion, the first 11 amino acids of the aph[3']-I gene product have been replaced by the first 11 amino acids of ORF1, and the expression of this hybrid gene is under the control of a *K. lactis* promoter. The nucleotide sequence surrounding the initation codon of the fusion protein ORF1-APH is as follows (codons originating from ORF1 are underlined, and the first codons from APH are italicized):

5'-TTACATTATTAATTTAAAA <u>ATG GAT TTC AAA GAT AAG

GCT TTA AAT GAT CTA</u> *AGG CCG CGA TTA AAT TCC AAC*

. . . -3'

E.4.4. Construction and stability of plasmid pKan707 in *K. lactis*.

Figure 14:
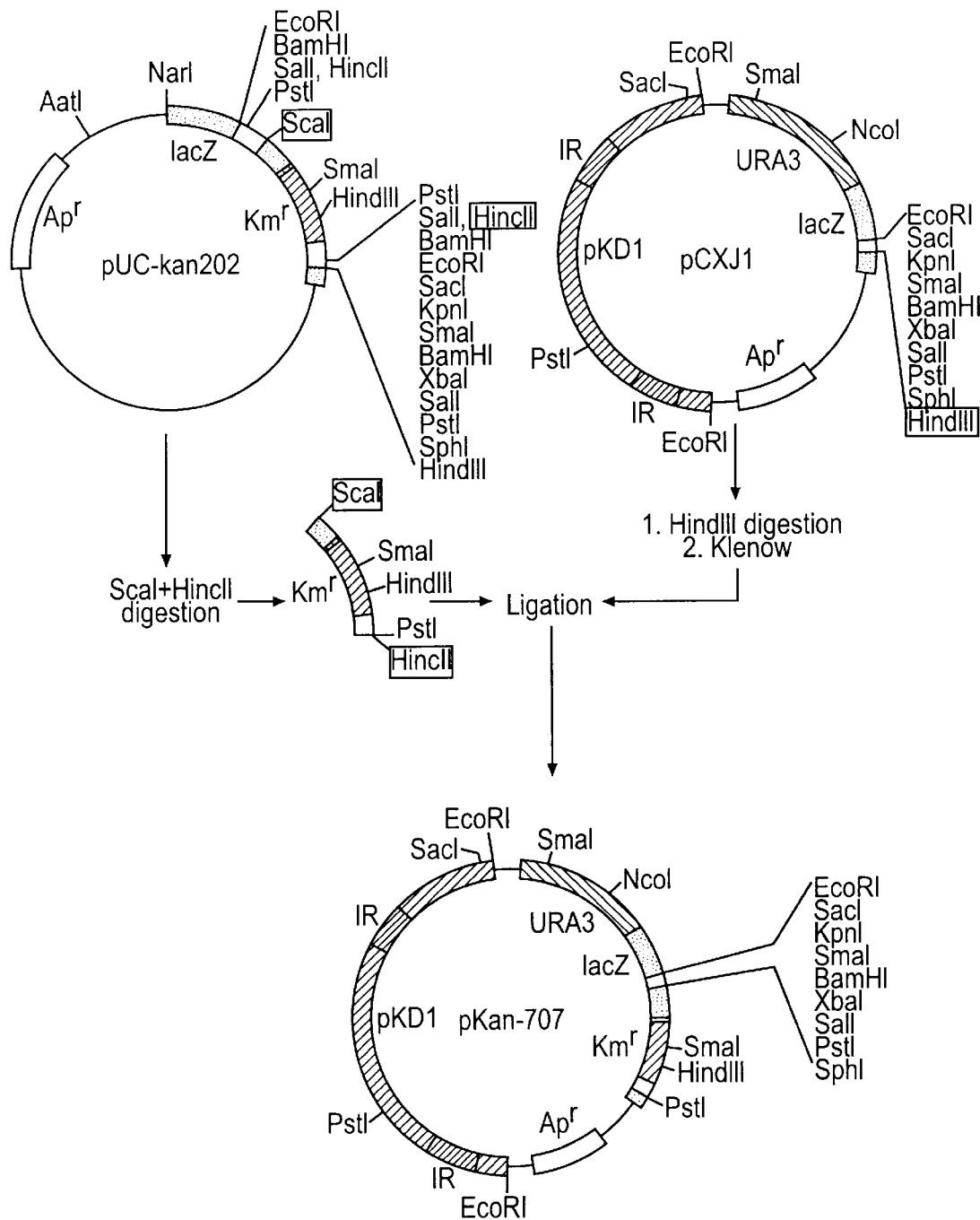
FIG. 14: Construction of plasmid pKan707.
Figure 15:
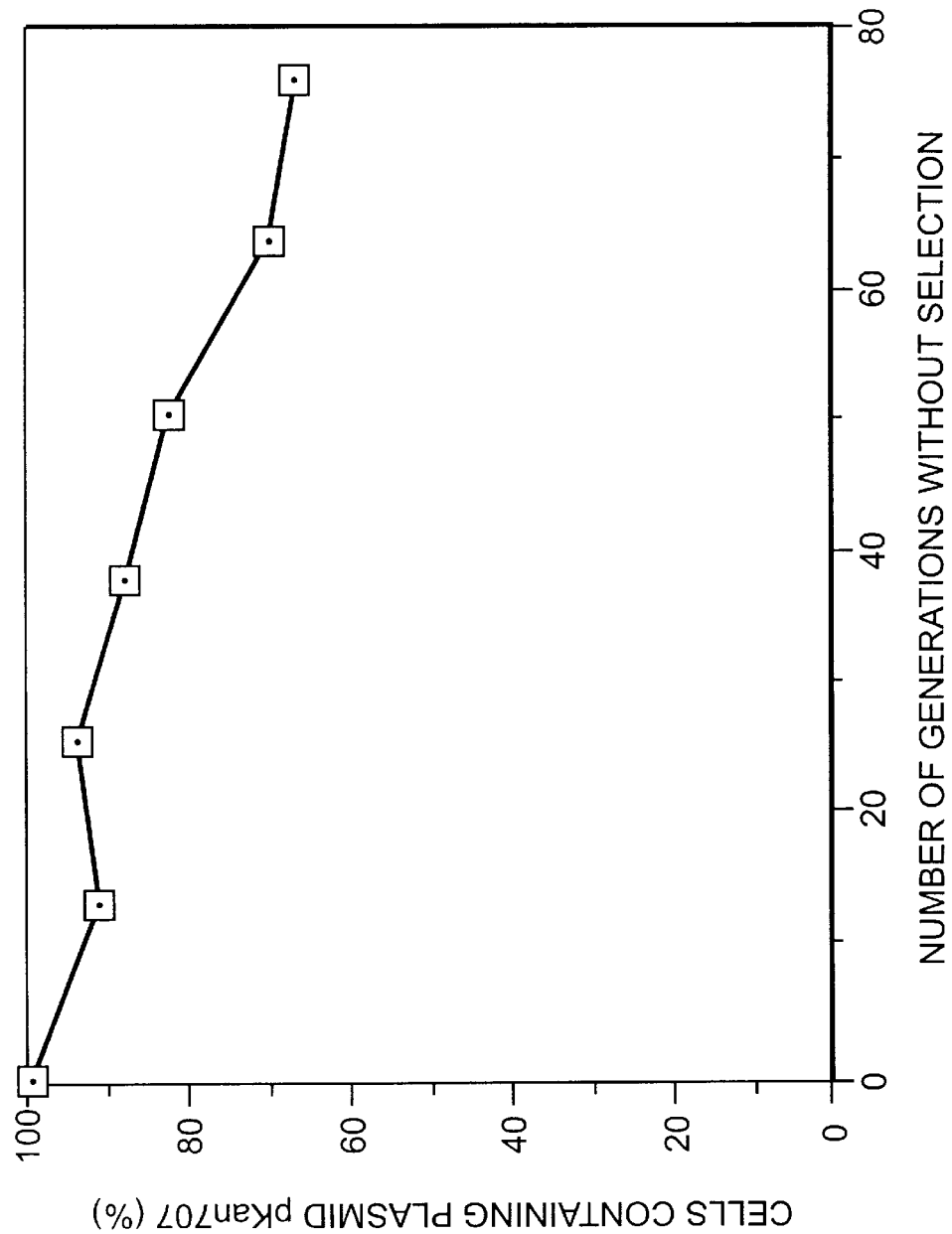
FIG. 15: Stability curve of plasmid pKan707 in strain MW98-8C under nonselective growth conditions.

Plasmid pCXJ1 was cleaved by HindIII, treated with the Klenow fragment of *E. coli* DNA polymerase I, then ligated with the 1.2 kb ScaI-HincII fragment coding for the ORF1-APH fusion expressed under control of the *K. lactis* $P_{k1}$ promoter deriving from plasmid pUC-Kan202. The resulting plasmid (pKan707, FIG. 14) confers very high levels of resistance to G418 (Geneticin, GIBCO, Grand Island, N.Y.) in strains of *K. lactis* (>2,5 g/l), is able to transform *K. lactis* strains cir° due to the functional integrity of replicon pKD1, can be amplified to 70–100 copies per cell, and can be stably maintained in the absence of selection pressure (FIG. 15). This high stability, coupled with the presence of a dominant marker permitting the transformation of industrial strains of Kluyveromyces, make plasmid pKan707 a high performance vector for the expression of proteins in yeasts of the genus Kluyveromyces.

Example 5

CONSTRUCTION OF EXPRESSION PLASMIDS pYG221B (PREPRO-HSA) AND pYG308B (PREPRO-HSA-V1V2)

Figure 16:
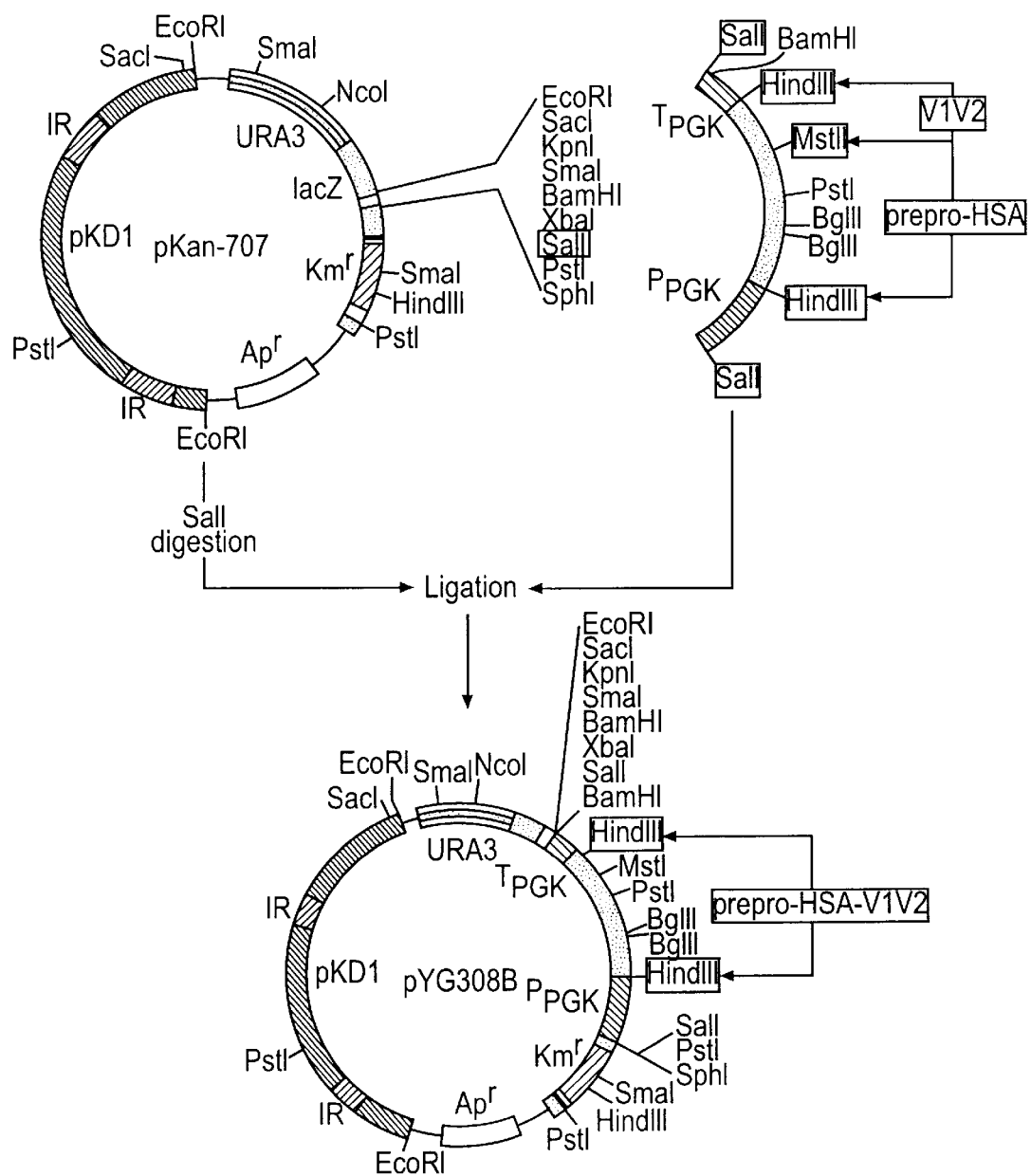
FIG. 16: Construction of plasmid pYG308B.

The SalI restriction fragment coding for the hybrid protein prepro-HSA-V1V2 expressed under control of the PGK promoter of *S. cerevisiae* was purified by electrolution from plasmid pYG306 cut by the corresponding enzyme, and then cloned into the SalI site of plasmid pKan707, to generate plasmids pYG308A and pYG308B which are distinguished only by the orientation of the SalI fragment in relation to the vector pKan707. A restriction map of plasmid pYG308B is shown in FIG. 16.

Figure 17:
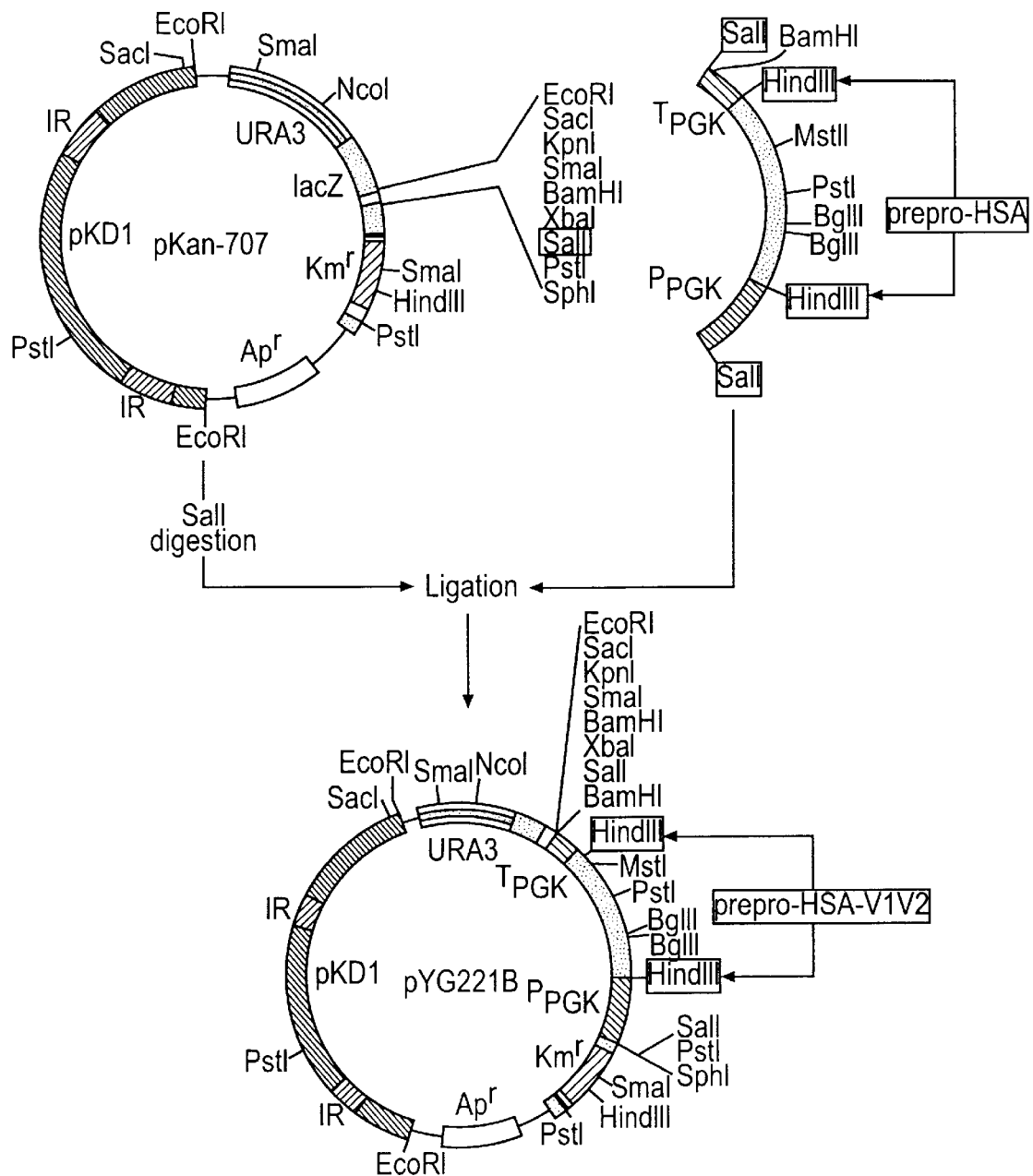
FIG. 17: Construction of plasmid pYG221B.

Plasmid pYG221B is a control construction coding for prepro-HSA alone; this plasmid was constructed as for plasmid pYG308B (prepro-HAS-V1V2): the SalI fragment coding for prepro-HSA expressed under control of the PGK promoter was purified from plasmid pYG210 and cloned into the SalI site of plasmid pKan707 to generate plasmid pYG221B (FIG. 17). Plasmids pYG221B (prepro-HSA) and pYG308B (prepro-HSA-V1V2) possess the same orientation of the SalI expression cassettes in relation to the vector and are strictly isogenic except for the difference of the MstII-HindIII fragment located immediately upstream of the PGK terminator. The nucleotide sequence of the MstII-HindIII fragment in plasmid pYG221B (prepro-HSA) is as follows (the translation stop codon for the prepro-HSA gene is in bold type):

5'-CCTTAGGCTTATAACATCACATT-
TAAAAGCATCTCAGCCTA

CCATGAGAATAAGAGAAAGAAAATGAAGATCAAAAGCTT-
3'

The nucleotide sequence of the MstII-HindIII fragment of plasmid pYG308B is included in the sequence of the MstII-SmaI fragment shown in FIG. 2.

Example 6

TRANSFORMATION OF YEASTS

Transformation of yeasts of the genus Kluyveromyces, and in particular *K. lactis* strain MW98-8C, was performed by treating whole cells with lithium acetate (Ito H. et al., J. Bacteriol. 153 (1983) 163–168), adapted as follows. Cells were grown in shaker flasks in 50 ml of YPD medium at 28° C., until reaching an optical density of 0.6–0.8, at which time they were harvested by low speed centrifugation, washed in sterile TE (10 mM Tris HCl pH 7,4; 1 mM EDTA), resuspended in 3–4 ml of lithium acetate (0.1 M in TE) to give a cell density of $2 \times 10^8$ cells/ml, then incubated 1 hour at 30° C. with moderate agitation. Aliquots of 0.1 ml of the resulting suspension of competent cells were incubated 1 hour at 30° C. in the presence of DNA and polyethylene glycol ($PEG_{4000}$, Sigma) at a final concentration of 35%. After a 25 minute thermal shock at 42° C., cells were washed twice, resuspended in 0.2 ml sterile water, and incubated 16 hours at 28° C. in 2 ml YPD to allow for phenotypic expression of the ORF1-APH fusion protein expressed under control of promoter $P_{k1}$; 200 μl of the resulting cell suspension were spread on YPD selective plates (G418, 200 μg/ml). Plates were incubated at 28° C. and transformants appeared after 2 to 3 days growth.

Example 7

SECRETION OF ALBUMIN AND ITS VARIANTS BY YEASTS OF THE GENUS KLUYVEROMYCES

After selection on rich medium supplemented with G418, recombinant clones were tested for their capacity to secrete the mature form of albumin or the hybrid protein HSA-V1V2. Certain clones corresponding to strain MW98-8C transformed by plasmids pYG221B (prepro-HSA) or pYG308B (prepro-HSA-V1V2) were incubated in selective liquid rich medium at 28° C. Culture supernatants were prepared by centrifugation when cells reached stationary phase, then concentrated by precipitation with 60% ethanol for 30 minutes at 20° C. Supernatants were tested after electrophoresis through 8.5% polyacrylamide gels, either by direct Coomassie blue staining of the gel (FIG. 18, panel A), or by immunoblotting using as primary antibody a rabbit polyclonal anti-HSA serum (FIG. 18, panel B) or a rabbit polyclonal anti-CD4 serum (FIG. 18, panel C). For immunoblot experiments, the nitrocellulose filter was first incubated in the presence of specific rabbit antibodies, then washed several times, incubated with a biotinylated goat anti-rabbit Ig's serum, then incubated in the presence of an avidin-peroxidase complex using the "ABC" kit distributed by Vectastain (Biosys S. A., Compiègne, France). The immunologic reaction was then revealed by addition of diamino-3,3' benzidine tetrachlorydrate (Prolabo) in the presence of oxygenated water, according to the kit recommendations. The results shown in FIG. 18 demonstrate that the hybrid protein HSA-V1V2 is recognized by both the anti-HSA antibodies and the anti-CD4 antibodies, whereas HSA is only recognized by the anti-HSA antibodies.

Example 8

PURIFICATION AND MOLECULAR CHARACTERIZATION OF SECRETED PRODUCTS

After ethanol precipitation of the culture supernatants corresponding to the *K. lactis* strain MW98-8C transformed by plasmids pYG221B (prepro-HSA) and pYG308B (prepro-HSA-V1V2), the pellet was resolubilized in a 50 mM Tris-HCl buffer, pH 8.0. The HAS-CD4 and HSA proteins were purified by affinity chromatography on Trisacryl-Blue (IBF). An additional purification by ion exchange chromatography can be performed if necessary. After elution, protein-containing fractions were combined, dialyzed against water and lyophylized before being characterized. Sequencing (Applied Biosystem) of the hybrid protein secreted by *K. lactis* strain MW98-8C revealed the expected N-terminal sequence of albumin (Asp-Ala-His . . . ), demonstrating the proper maturation of the protein.

The isoelectric point was determined by isoelectrofocalization to be 5.5 for the HSA-V1V2 protein and 4.8 for HSA.

Figure 19:
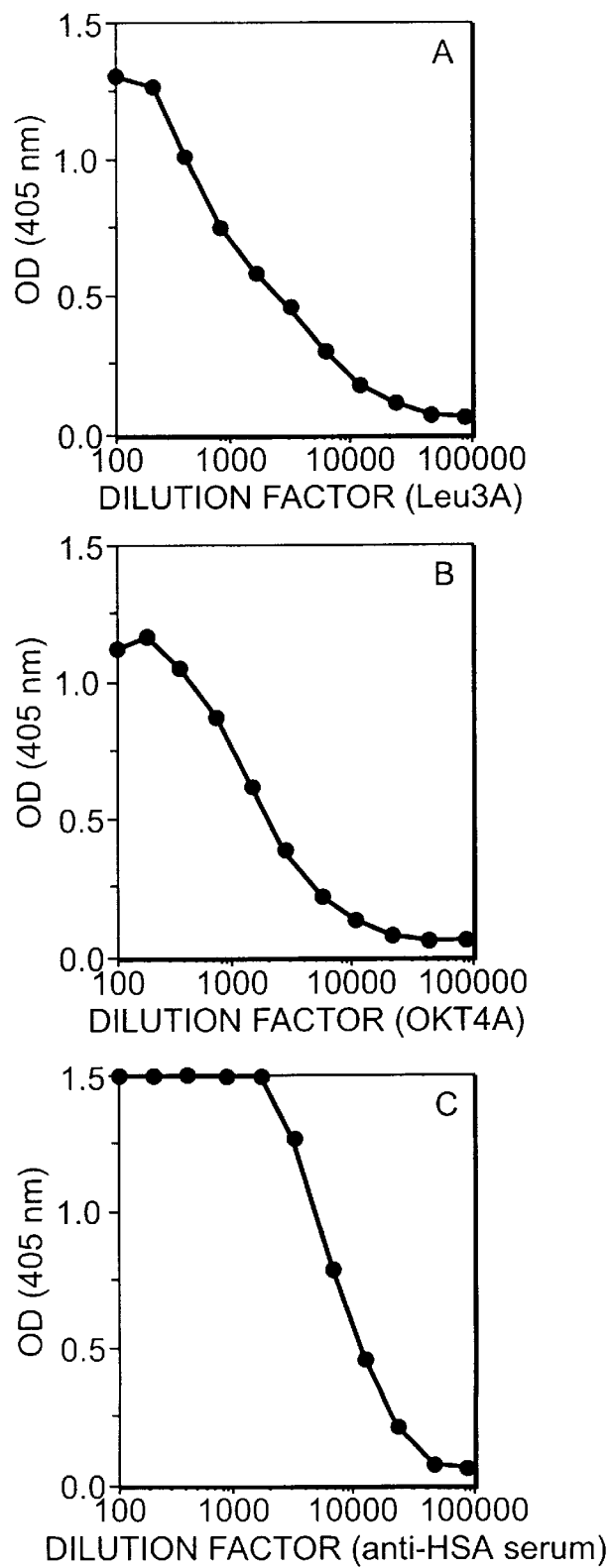
FIG. 19: Titration of the protein HSA-V1V2 (1 $\mu$g/ml) by mouse monoclonal antibody Leu3A (Becton Dickinson, Mountain View, Calif., U.S.A.) (panel A), by mouse monoclonal antibody OKT4A (Ortho Diagnostic Systems, Raritan, N.J., USA) (panel B), or by polyclonal goat anti-HSA coupled to peroxidase (Nordic, Tilburg, Netherlands) (panel C). After using antibodies Leu3A and OKT4A, a secondary rabbit anti-mouse antibody coupled to peroxidase (Nordic) is used. Titration curves for the three primary antibodies used in parts A, B and C were determined by measuring optical density at 405 nm after addition of a chromogenic substrate of peroxidase (ABTS, Fluka, Switzerland). Ordinate: OD at 405 nm, abscissa: dilution factor of the primary antibody used.
Figure 20A:
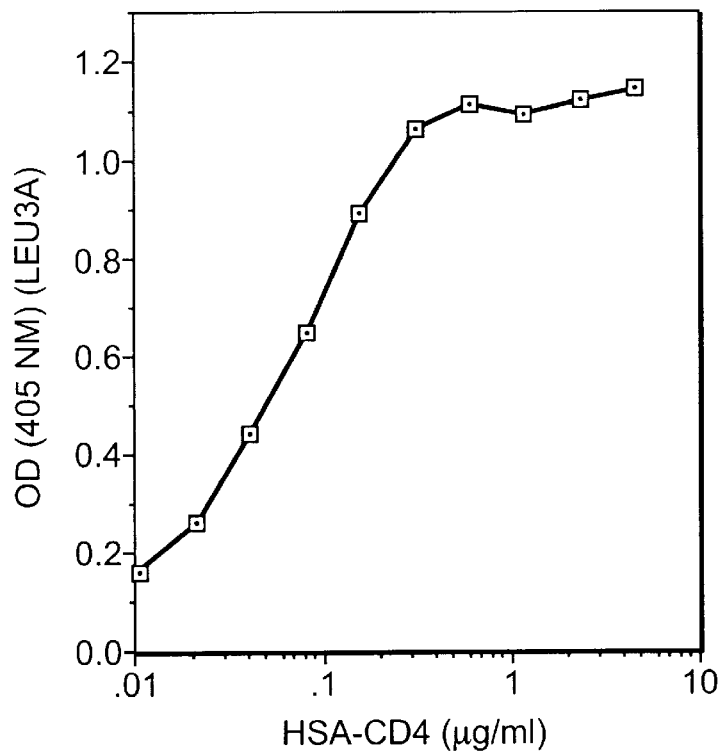
FIG. 20: Assay of protein HSA-V1V2 by the ELISA sandwich method: rabbit polyclonal anti-HSA (Sigma)/HSA-V1V2/mouse monoclonal antibody Leu3A (Becton Dickinson) (panel A), or rabbit polyclonal anti-HSA (Sigma)/HSA-V1V2/mouse monoclonal antibody OKT4A (Ortho Diagnostic Systems) (panel B). After incubation of each antibody with the HAS-V1V2 protein, a secondary rabbit anti-mouse antibody coupled to peroxidase (Nordic) is added. Titration curves were determined by measuring optical density at 405 nm after addition of the peroxidase substrate ABTS. Ordinate: OD at 405 nm; abscissa: concentration of HSA-V1V2 in $\mu$g/ml.
Figure 20B:
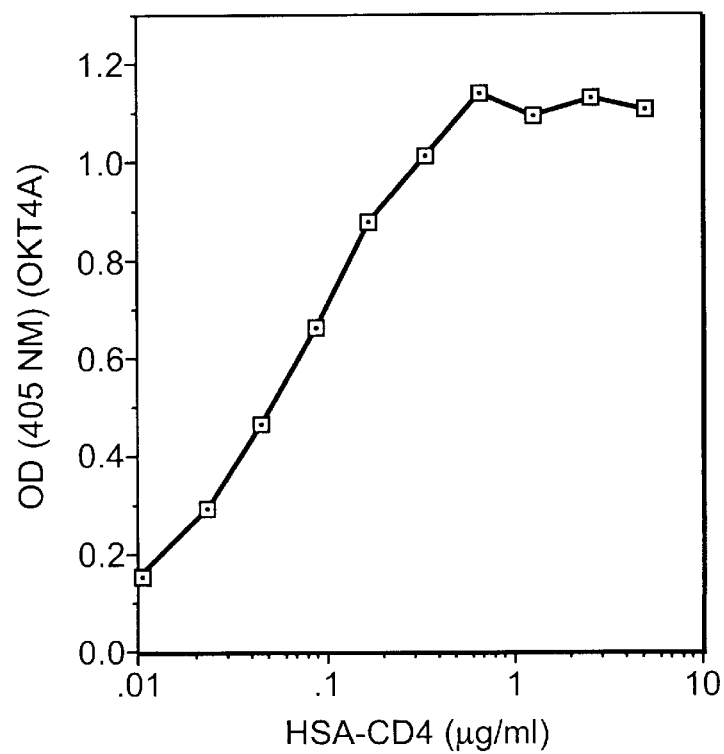

The HSA-V1V2 protein is recognized by the monoclonal mouse antibodies OKT4A and Leu3A directed against human CD4, as well as by a polyclonal anti-HSA serum (FIG. 19), and can be assayed by the ELISA method (Enzyme-Linked Immuno-Sorbent Assay, FIG. 20). The substrate for the peroxidase used in these two experiments is 2-2'-azino-bis (3ethylbenzothiazoline-6-sulfonic acid) diammonium salt (ABTS) (Fluka, Switzerland).

Example 9

CHARACTERIZATION OF THE ANTI-VIRAL PROPERTIES OF THE HSA-CD4 VARIANTS

The proteins corresponding to albumin (negative control) and to the HSA-V1V2 fusion purified from culture supernatants of *K. lactis* strain MW98-8C transformed respectively by plasmids pYG221B (prepro-HSA) and pYG308B (prepro-HSA-V1V2) as in examples 7 and 8, were tested in vitro for antiviral activity and compared to the entire soluble CD4 molecule purified from CHO (Chinese Hamster Ovary) cells. Protein concentrations are expressed in molarity and were determined both by methods to measure proteins in solution as well as by comparison of successive dilutions of each protein after electrophoretic migration in polyacrylamide gels followed by silver nitrate staining.

Figure 21:
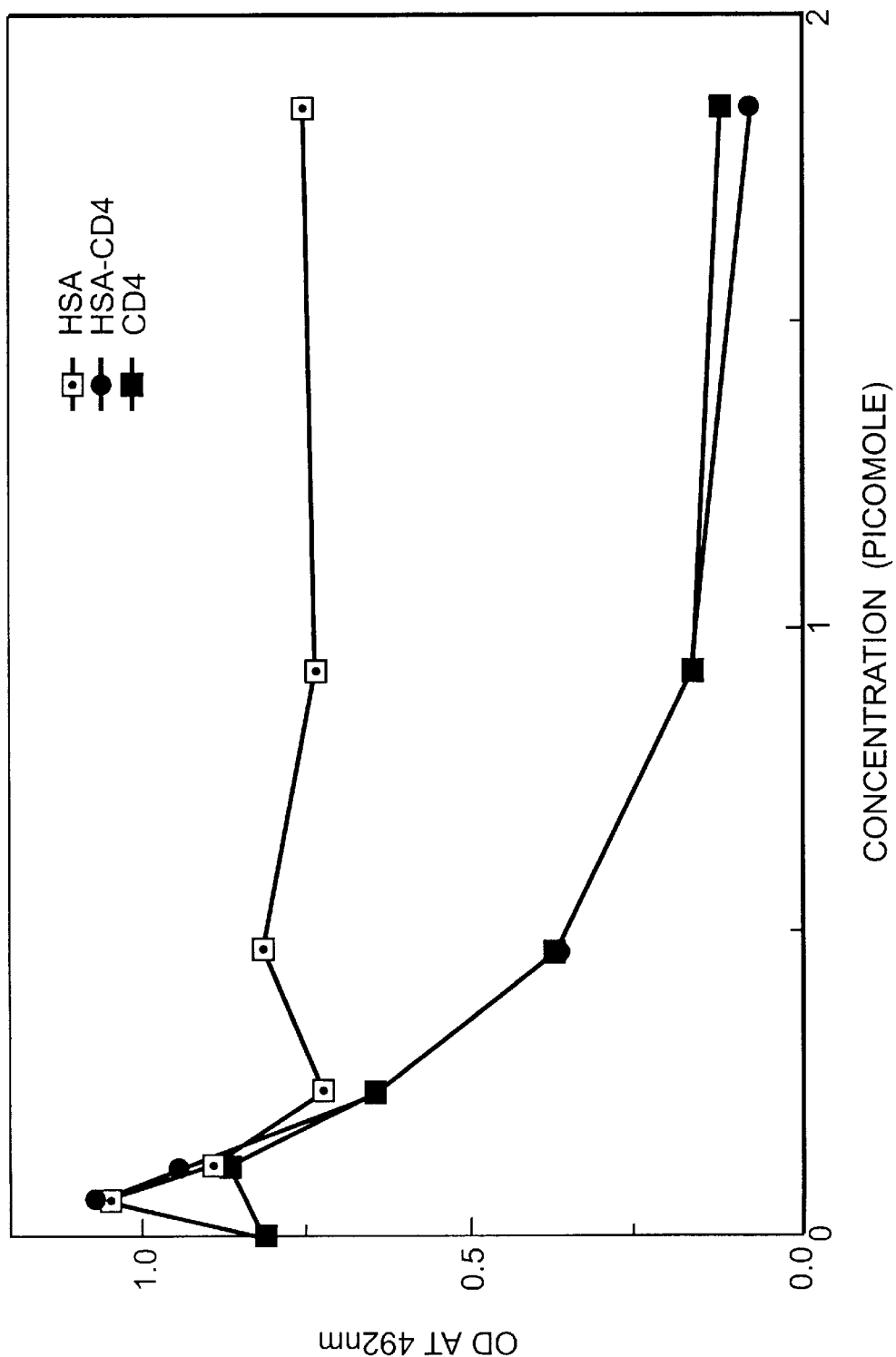
FIG. 21: Soluble phase inhibition of binding to CD4 by 125 femtomoles of recombinant gp160 protein (Transgène, Strasbourg, France). Optical density at 492 nm is represented on the ordinate (the value 2 is the saturation optical density of the system) and the quantities of HSA (control), HSA-CD4, and soluble CD4 are shown on the abscissa (picomoles of protein).

FIG. 21 shows that the HSA-V1V2 fusion is able to inhibit in vitro the binding of the viral glycoprotein gp160 (uncleaved precursor of gp120) to the CD4 receptor in soluble phase. In this experiment, the ELISA plates were covered with purified recombinant CD4 and incubated with recombinant gp160 (125 femtomoles) and having been preincubated with varying quantities of CD4, albumin, or the hybrid protein HSA-V1V2. The residual binding of gp160 to CD4 was then revealed by the successive addition of mouse monoclonal anti-gp160 (110.4), followed by the binding of a goat serum linked to peroxidase and directed against mouse antibodies. After addition of a chromogenic substrate (orthophenyldialenine) in the presence of oxygenated water, optical density was measured at 492 nm. The results reported in FIG. 21 demonstrate that the hybrid protein HAS-V1V2 is able to inhibit the binding of gp160 to CD4 in soluble phase, in a manner indistinguishable from the positive control corresponding to the entire CD4 molecule. In contrast, the albumin molecule is almost completely inactive in this regard. This experiment indicates that the inhibition by the hybrid protein is due to the presence of the V1V2 domains in a conformation and accessibility similar to the complete CD4 receptor.

Figure 22A:
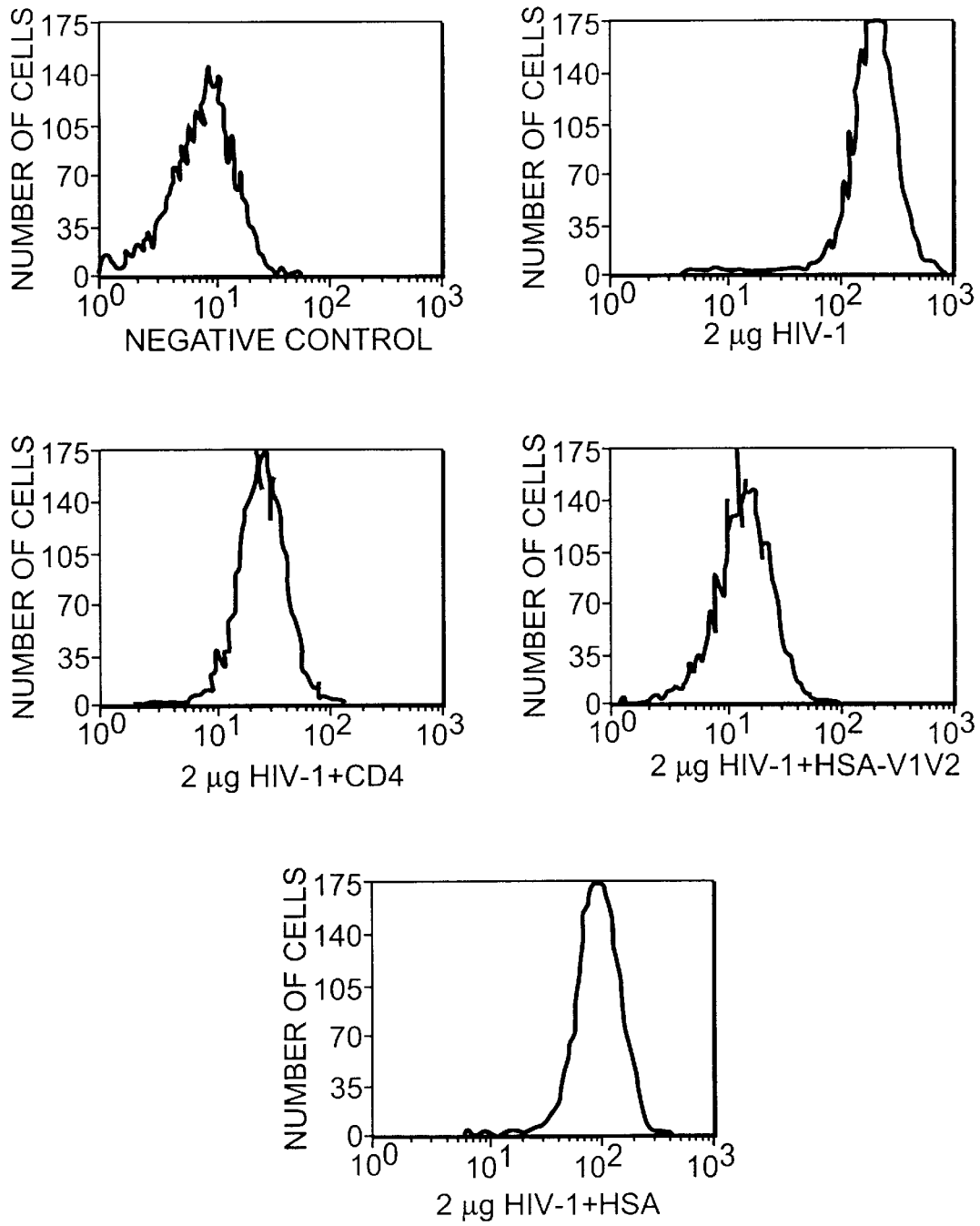
FIG. 22: Inhibition of the binding of inactivated HIV-1 virus to cell line CEM13. A, preliminary analysis of cell populations sorted as a function of their fluorescence. Ordinate: cell number; abscissa: fluorescence intensity (logarithmic scale). B, histogram of cell populations sorted as a function of their fluorescence. Column 1, negative control; Column 2, HIV-1 virus; Column 3, HIV-1 virus preincubated with 116 picomoles of CD4 recombinant protein; Column 4, HIV-1 virus preincubated with 116 picomoles of HSA-V1V2; Column 5, HIV-1 virus preincubated with 116 picomoles of HSA.
Figure 22B:
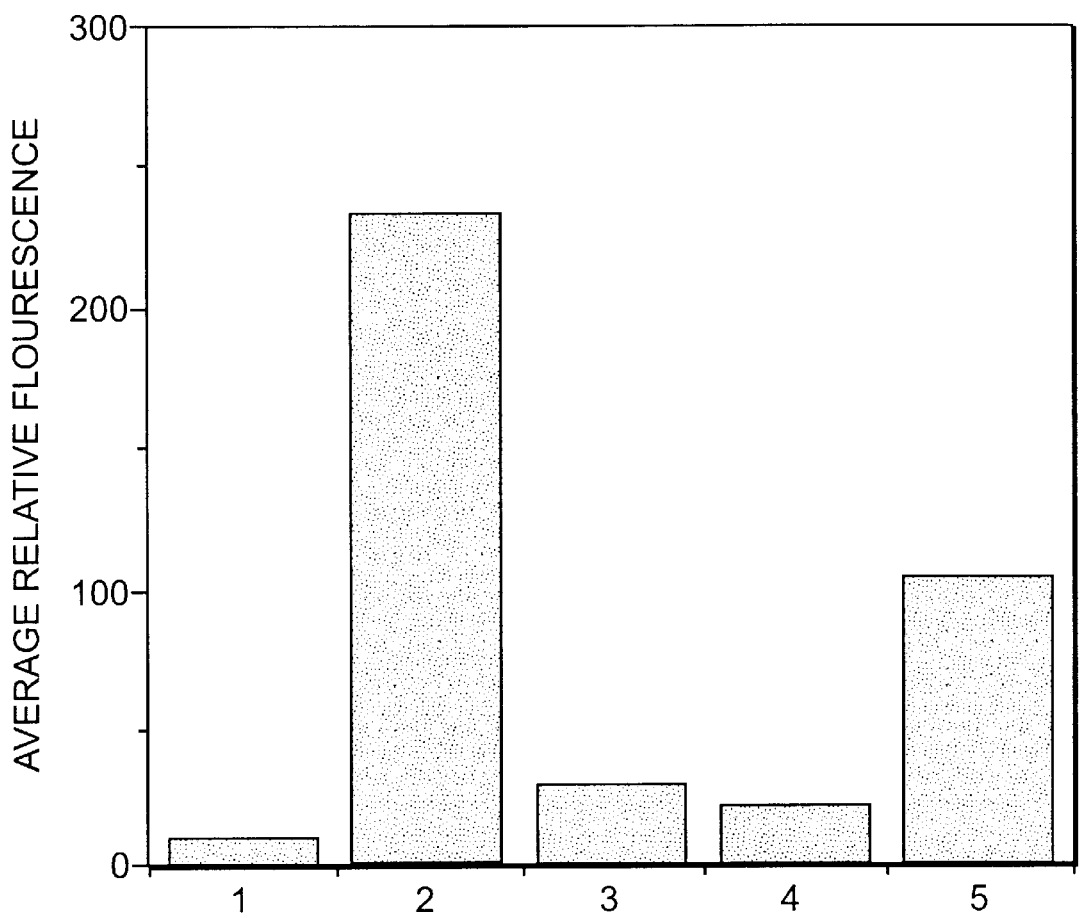

FIG. 22 shows that the HSA-V1V2 hybrid is able to inhibit the in vitro binding of the HIV-1 virus to cells expressing the CD4 receptor on their membranes. In this experiment, a cell line that expresses high quantities of CD4 receptor (lymphoblastic cell line CEM13) was incubated with 2 µg of heat-inactivated viral particles that had been preincubated with 116 picomoles of either HSA-V1V2 (10.7 µg), HSA (7.5 µg), or recombinant entire CD4 purified from CHO cells (5 µg). The binding of the inactivated viral particles to cell membranes was revealed by successive incubations of a mouse monoclonal anti-gp120 antibody and a goat anti-mouse IgG serum marked with phycoerythrin. The negative control corresponds to cell line CEM13 incubated successively with these two antibodies. Fluorescence was measured with a cell sorter (FIG. 22, panel A) and the results are presented in the form of a histogram (FIG. 22, panel B). This experiment shows that the HSA-V1V2 protein is able to inhibit the binding of the HIV-1 virus to CEM13 cells almost completely. Furthermore, this inhibition is slightly higher than that of the complete CD4 molecule; this can be explained by the fact that albumin, known for its adhesive properties, is able to inhibit the binding of the virus to the target cells in a nonspecific manner and with a low efficiency.

The HSA-CD4 protein is also able to inhibit viral infection of permissive cells in cell culture. This inhibition was measured either by assaying the production of viral antigens (viral p24) using the kit ELAVIA-AG1 (Diagnostics Pasteur), or the kit p24-ELISA (Dupont), or by measuring the reverse transcriptase activity by the technique of Schwartz et al. (Aids Research and Human Retroviruses 4 (1988) 441–448). The experimental protocol was as follows: the product of interest at a final concentration X was first preincubated with supernatants of CEM13 cells infected by the isolate LAV-Bru1 of virus HIV-1 (dilution $\frac{1}{250}$, $\frac{1}{2500}$ and $\frac{1}{25000}$) in a total volume of 1 ml of culture medium (RPMI 1640 containing 10% fetal calf serum, 1% L-glutamine and 1% penicillin-streptomycin-neomycin). The mixture was then transfered onto a pellet of $5 \times 10^5$ permissive cells (e.g. MT2, CEM13, or H9) and incubated in tubes for 2 hours at 37° C. for infection to occur. The infection could also be carried out on microtitration plates with $10^4$ cells per well in 100 µl of complete medium. A volume of 100 µl of the virus that had been preincubated with the product to be tested was then added, followed by 50 µl of the product at 5× concentration. Cells were then washed twice with 5 ml RPMI 1640 and resuspended in culture medium at a density of $2:5 \times 10^5$ cells/ml. 100 µl of this suspension was then aliquoted into each well of microtitration plates which already contain 100 µl of the product at 2× concentration, and the plates were incubated at 37° C. in a humid atmosphere containing 5% $CO_2$. At different days (D3-D4-D6-D8-D10-D12-D14-D16-D19-D21 and D25), 100µl of supernatant was removed and the p24 viral production as well as the reverse transcriptase activity were assayed. Cells were then resuspended and distributed onto microtitration plates for assays of cell viability (MTT) as described above. To the 50 µl remaining on the original plates, 200 µl of culture medium containing the product to be tested at concentration X were added, and infection was allowed to progress until the next sampling. For the cell viability test, 10 µl of MTT at 5 mg/ml filtered on 0.2 µm filters was added to each well and plates were incubated 4 hours at 37° C. in a humid atmosphere containing 5% $CO_2$. Then to each well was added 150 µl of an isopropanol/0.04 N HCl mixture, and the Formazan crystals were resuspended. Optical density from 520 to 570 nm was measured on a Titertek plate reader; this measure reflects cell viability (Schwartz et al., Aids Research and Human Retroviruses 4 (1988) 441–448).

Figure 23:
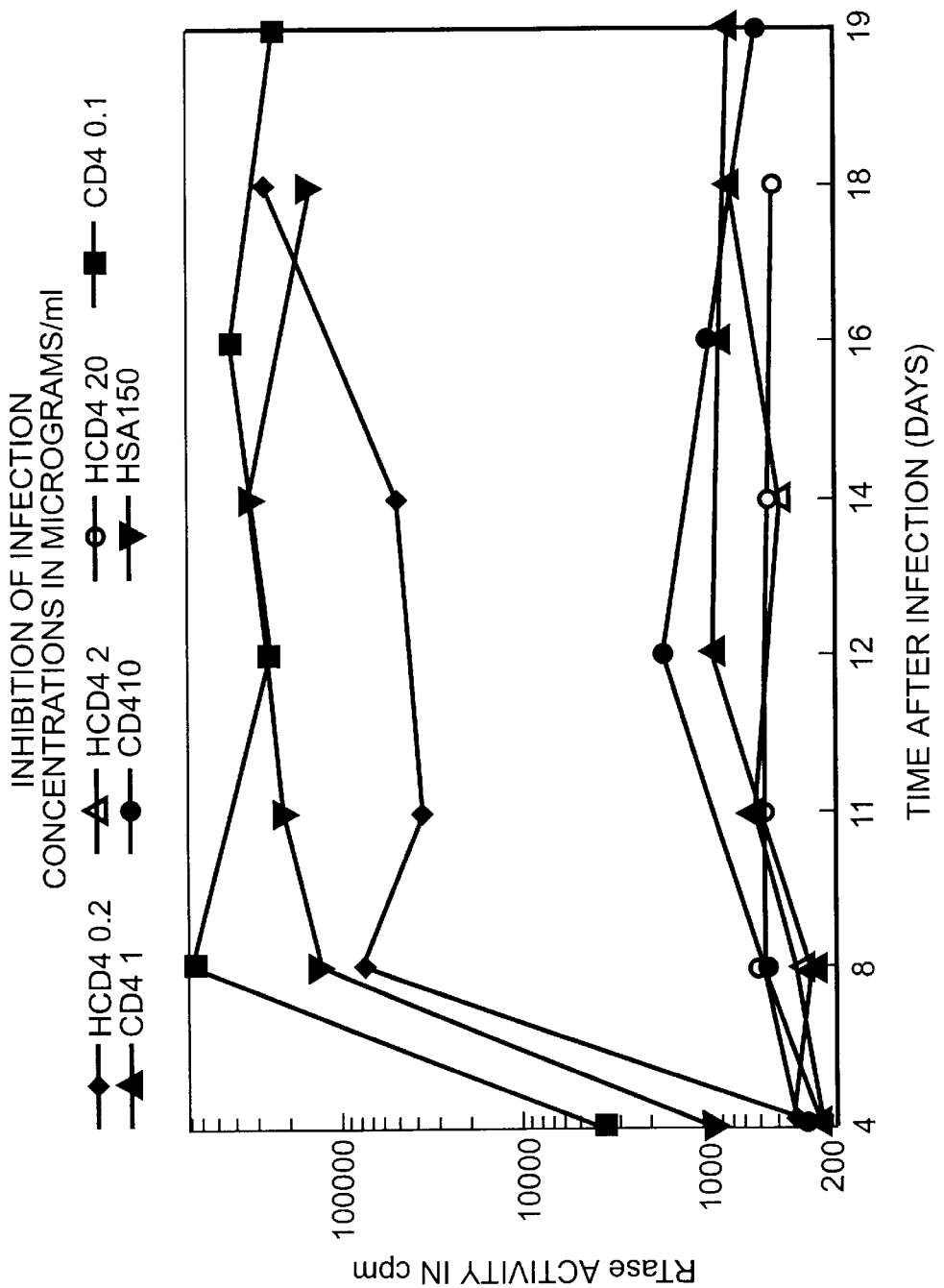
FIG. 23: Inhibition of infection in cell culture. Reverse transcriptase activity was measured for 19 days after infection of CEM13 cells. Assays were performed on microtitration plates according to the following protocol: into each well, 10 µl of Buffer A (0.5 M KCl, 50 mM DTT, 0.5% Triton X-100), then 40 µl of Buffer B (10 µl 5 mM EDTA in 0.5 M Tris-HCl pH 7.8, 1 µl 0.5 M MgCl$_2$, 3 µl $^3$H-dTTP, 10 µl poly rA-oligodT at 5 OD/ml, 16 µl H$_2$O) were added to 50 µl culture supernatant removed at different times after infection. The plates were incubated for 1 hour at 37° C., then 20 µl of Buffer C (120 mM Na$_4$P$_2$O$_7$ in 60% TCA) was added and incubation was continued for 15 minutes at 4° C. The precipitates formed were passed through Skatron filters using a Skatron cell harvester, and washed with Buffer D (12 mM Na$_4$P$_2$O$_7$ in 5% TCA). Filters were dried 15 minutes at 80° C. and the radioactivity was measured in a scintillation counter. Three independent samples were tested for each point.
Figure 24:
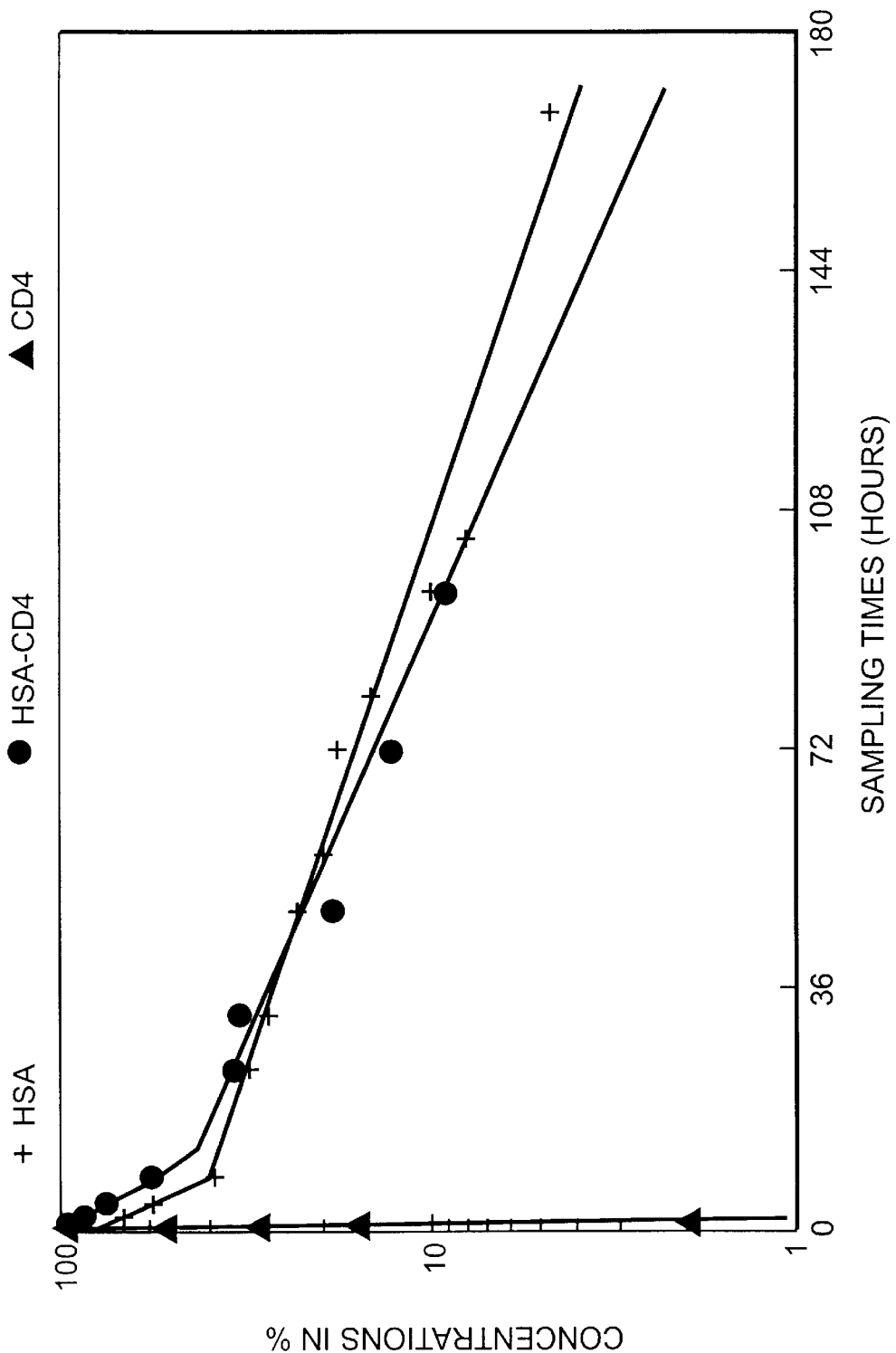
FIG. 24: Changes in the in vivo concentrations of CD4, HSA and HAS-CD4 over time.

FIG. 23 shows an example of inhibition of infectivity in cell culture (cell line CEM13) as measured by reverse transcriptase activity. This demonstrates that the HSA-V1V2 hybrid is able to reduce the infectivity of the HIV-1 virus to the same extent as the soluble CD4 molecule.

Example 10

STABILITY OF THE HYBRID PROTEINS IN VIVO

It has been shown that first generation soluble CD4 possesses a half-life of 20 minutes in rabbits (Capon D. J. et al.; Nature 337 (1989) 525–531). We have therefore compared the half-life in rabbits of the HAS-CD4 hybrid to soluble CD4 and to recombinant HSA produced in yeast and purified in the same manner as HSA-CD4. In these experiments, at least 2 male NZW(Hy/Cr) rabbits weighing 2.5–2.8 kg were used for each product. Rabbits were kept in a room maintained at a temperature of 18.5–20.5° C. and a humidity of 45–65%, with 13 hours light/day. Each product was administered in a single injection lasting 10 seconds in the marginal vein of the ear. The same molar quantity of each product was injected: 250 μg of CD4 per rabbit, 400 μg of HSA per rabbit, or 500 μg of HAS-CD4 per rabbit, in 1 ml physiologic serum. Three to four ml blood samples were taken, mixed with lithium heparinate and centrifuged 15 min at 3500 rpm; samples were then divided into three aliquots, rapidly frozen at −20° C., then assayed by an ELISA method. Blood samples from rabbits injected with CD4 were taken before injection (To), then 5 min, 10 min, 20 min, 30 min, 1 h, 2 h, 4 h and 8 h after injection. Blood samples from rabbits injected with HAS-CD4 or HSA were taken at To, 30 min, 1 h, 2 h, 4 h, 8 h, 24 h, 32 h, 48 h, 56 h, 72 h, 80 h, 96 h, 104 h and 168 h after injection.

Assays of the CD4 molecule were carried out on Dynatech M129B microtitration plates previously covered with the HAS-CD4 hybrid protein. Increasing concentrations of CD4 or the samples to be assayed were then added in the presence of the mouse monoclonal antibody OKT4A (Ortho-Diagnostic, dilution 1/1000); after incubation and washing of the plates, the residual binding of antibody OKT4A was revealed by addition of antibodies coupled to peroxidase (Nordic, dilution 1/1000) and directed against mouse IgG. Measurements were made at OD 405 nm in the presence of the peroxidase substrate ABTS (Fluka).

Assays of recombinant HSA were carried out on Dynatech M129B microtitration plates previously covered with anti-HSA serum (Sigma Ref. A0659, dilution 1/1000); increasing concentrations of HSA or samples to be measured were then added, followed by addition of anti-HSA serum coupled to peroxidase (Nordic, dilution 1/1000). Measurements were made at OD 405 nm as above.

Two different assays were done for the HSA-CD4 hybrid: either the assay for the HSA moiety alone, using the same methods as for recombinant HSA, or an assay for the HSA moiety coupled with an assay for the CD4 moiety. In the latter case, microtitration plates were covered first with anti-HSA serum (Sigma Ref. A0659, dilution 1/1000), then incubated with the samples to be assayed. The mouse monoclonal antibody Leu3A directed against CD4 was then added, followed by antibodies coupled to peroxidase (Nordic, dilution 1/1000) and directed against mouse antibodies. Measurements were made at 405 nm as described above.

The curves for each of these assays are given in FIG. 24. Interpretation of these results allows the evaluation of the pharmacokinetic characteristics of each product in the rabbit. The half-lives measured for each product are as follows:

CD4: 0.25±0.1 h

HSA: 47±6h

HSA-CD4: 34±4 h

These results underscore the following points:

1/ The coupling of CD4 to albumin allows a significant increase in the stability of CD4 in the organism since the half-life of elimination is increased 140-fold.

2/ The half-life of elimination of the HSA-CD4 hybrid is comparable to that of HSA.

3/ The clearance of CD4 is approximately 3 ml/min/kg while that of HSA and HSA-CD4 is approximately 0.02 ml/min/kg.

4/ The CD4 moiety of the HSA-CD4 hybrid apparently retains an active conformation (i.e. able to bind gp120) since the assay for CD4 involves the Leu3A monoclonal antibody which recognizes an epitope close to the binding site of gp120 (Sattentau Q. J. et al., Science 234 (1986) 1120–1123; Peterson A. and Seed B., Cell 54 (1988) 65–72). Furthermore, the two independent assay methods for the HSA-CD4 hybrid gave essentially the same result, which suggests that the CD4 moiety is not preferentially degraded in vivo.

It is noteworthy that the volume of distribution of HSA and HAS-CD4 is dose to that of the blood compartment, and therefore suggests a distribution of the product limited to the extracellular compartment.

Example 11

GENERIC CONSTRUCTIONS OF THE TYPE HSA-CD4

E.11.1. Introduction of AhaII and BglII sites at the end of the prepro region of HSA.

Introduction of the AhaII restriction site was carried out by site-directed mutagenesis using plasmid pYG232 and oligodeoxynucleotide Sq1187, to generate plasmid pYG364. Plasmid pYG232 was obtained by cloning the HindIII fragment coding for prepro-HSA into the vector M13 mp9. The sequence of oligodeoxynucleotide Sq1187 is (the AhaII site is in bold type):

5'-GTGTTTCGTCGAGACGCCCACAAGAGTGAGG-3'.

It should be noted that creation of the AhaII site does not modify the protein sequence of the N-terminal of mature HSA. The construction of plasmid pYG364 is shown in FIG. 25.

Plasmid pYG233 was obtained in analogous fashion, after site-directed mutagenesis of plasmid pYG232 using oligodeoxynucleotide Sq648 (the codons specificying the amino acid pair Arg—Arg situated at the end of the prepro region of HSA are in bold type, and the BglII site is underlined):

5'-GGTGTGTTTCGTAGATCTGCACACAAGAGTGAGG-3'

Figure 25:
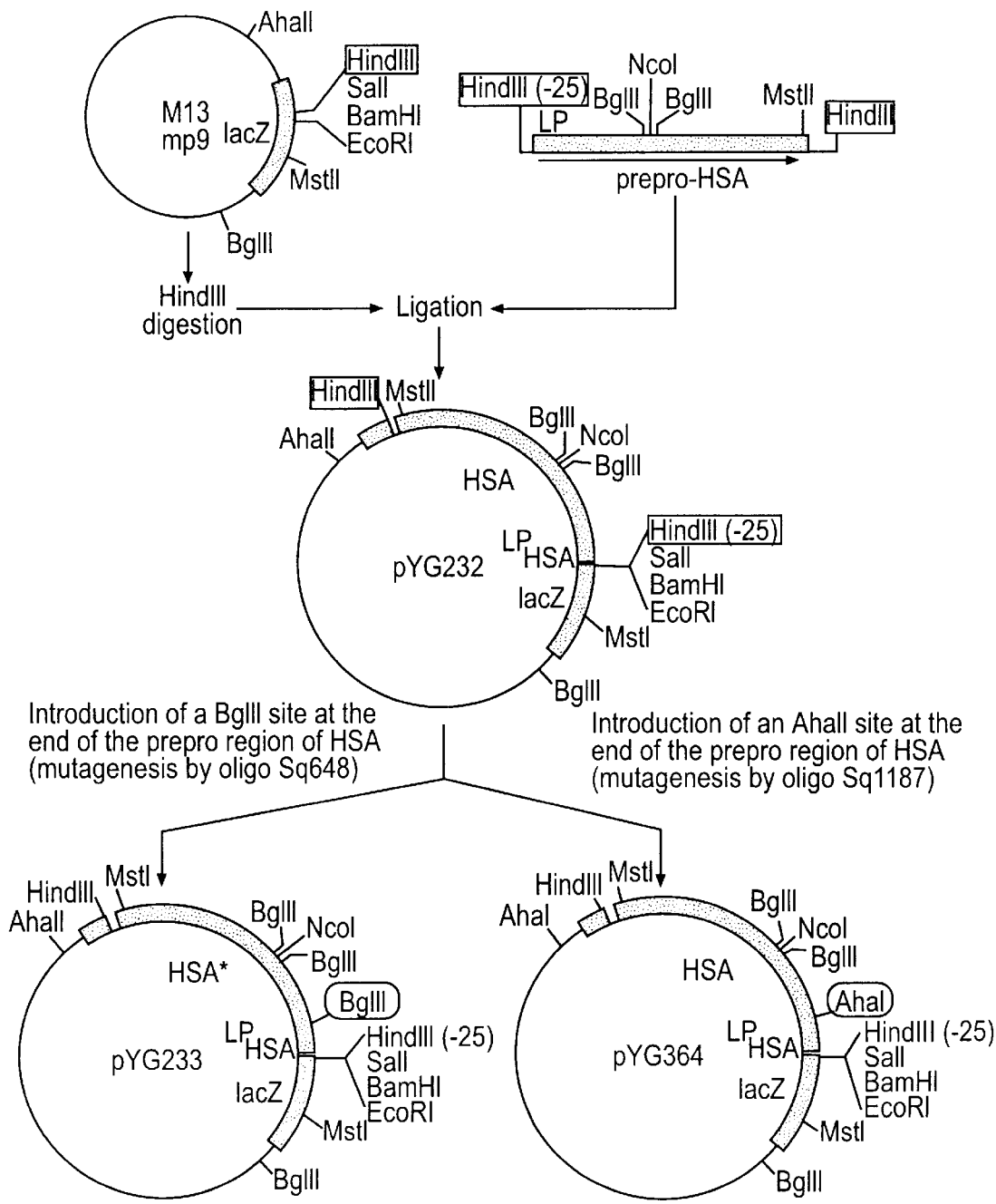
FIG. 25: Construction of plasmids pYG232, pYG233 and pYG364.

The creation of this restriction site does not change the protein sequence of the prepro region of HSA. In contrast, the first amino acid of the mature protein is changed from an aspartate to a serine; plasmid pYG233 therefore codes for a mature HSA modified at its N-terminal (HSA*, FIG. 25).

E.11.2. Introduction of the prepro region of HSA upstream of the CD4 receptor.

Figure 26:
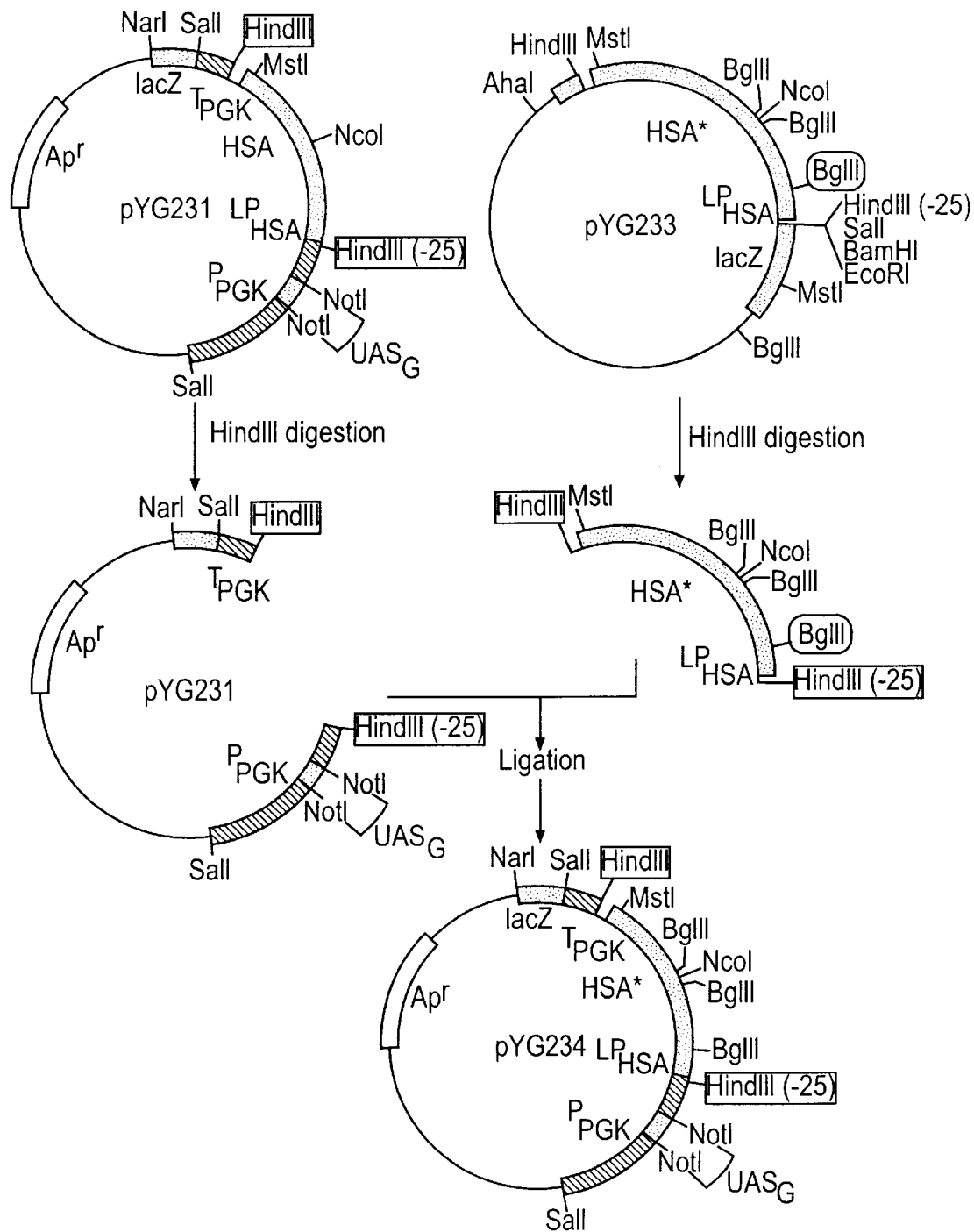
FIG. 26: Construction of plasmid pYG234.
Figure 27:
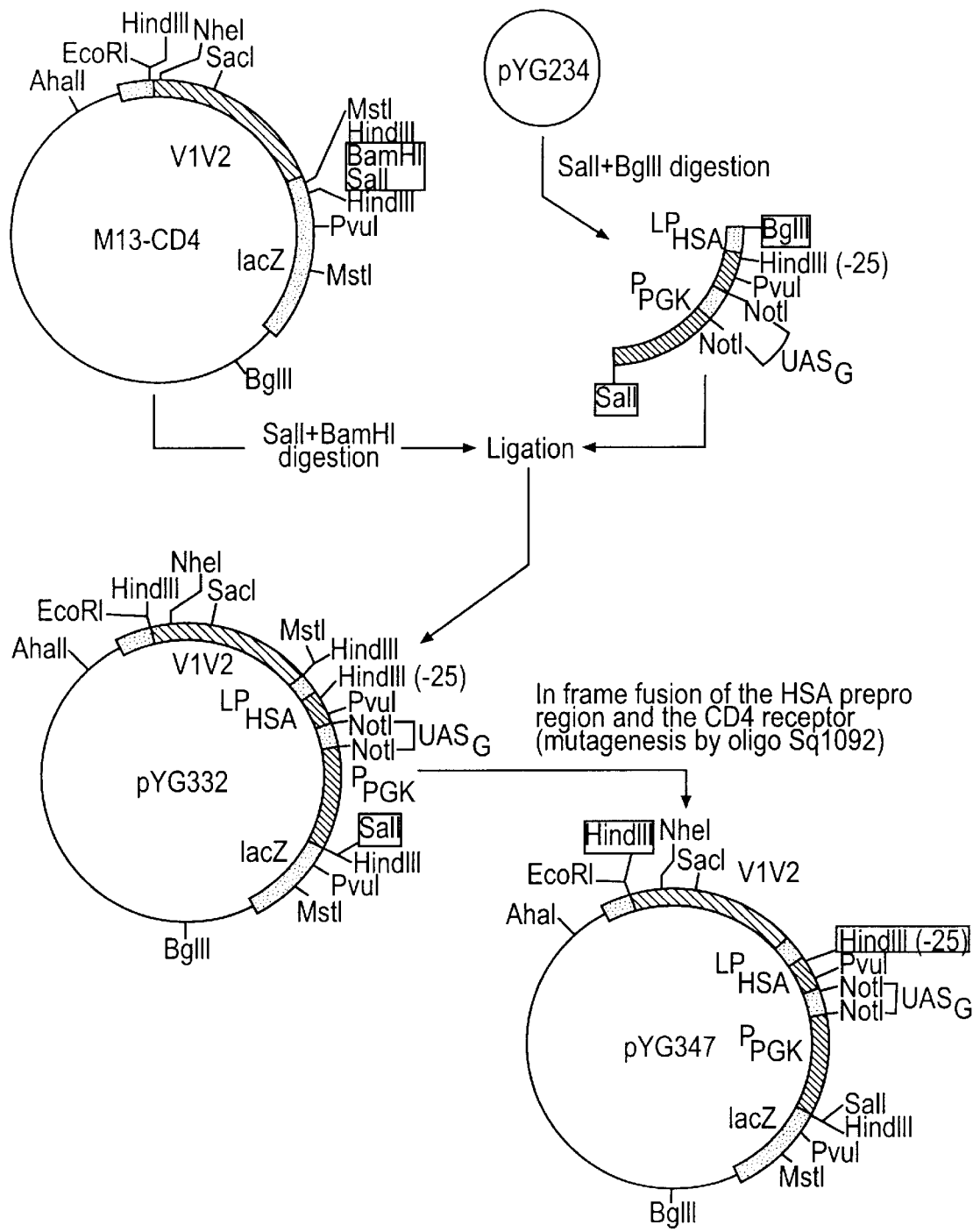
FIG. 27: Construction of plasmids pYG332 and pYG347.

The introduction of the prepro region of HSA upstream of the V1V2 domains of the CD4 receptor was accomplished by site-directed mutagenesis, to generate plasmid pYG347 as shown in FIGS. 26 and 27. Plasmid pYG231 (FIG. 26) is an intermediate construction corresponding to a pUC-type replicon into which has been cloned a SalI fragment carrying the expression cassette for HSA (yeast promoter/prepro-HSA/PGK terminator of S. cerevisiae). Plasmid pYG234 is isogenic to plasmid pYG231 except that oligodeoxynucleotide Sq648 was used to carry out the in vitro mutagenesis (E.11.1.).

Plasmid pYG347 was obtained by site-directed mutagenesis of plasmid pYG332 with oligodeoxynucleotide Sq1092 (FIG. 27) whose sequence is as follows (HSA sequence is in italics and CD4 sequence is in bold type):

5'-CCAGGGGTGTGTTTCGTCGAAA-GAAAGTGGTGCTGGGC-3'

Plasmid pYG347 therefore carries a HindIII fragment composed of the 21 nucleotides preceding the ATG codon of the PGK gene of S. cerevisiae, the ATG translation initiation codon, and the prepro region of HSA (LP$_{HSA}$) immediately followed by the V1V2 domains of the CD4 receptor.

E.11.3. Introduction of an AhaII site at the end of the V1 domain of the CD4 receptor.

The introduction of an AhaII site at the end of the V1 domain of the CD4 receptor was accomplished by site-directed mutagenesis using oligodeoxynucleotide Sq1185 and a derivative of plasmid pYG347 (pYG368, FIG. 28), to generate plasmid pYG362. The sequence of oligodeoxynucleotide Sq1185 is (the AhaII site is shown in bold type):

5'-CCAACTCTGACACCGACGCCCACCTGCTTCAGG-3'.

Plasmid pYG362 therefore carries a HindIII-AhaII fragment composed of the 21 nucleotides preceding the ATG codon of the PGK gene of S. cerevisiae followed by the coding sequence of the HSA prepro region fused to the V1 domain of the CD4 receptor, according to example E.11.2. In a fusion such as the example given here, the V1 domain of the CD4 receptor carries 106 amino acids and includes the functional binding site of the HIV-1 viral glycoprotein gp120.

E.11.4. Introduction of an AhaII site at the end of the V2 domain of the CD4 receptor.

Figure 28:
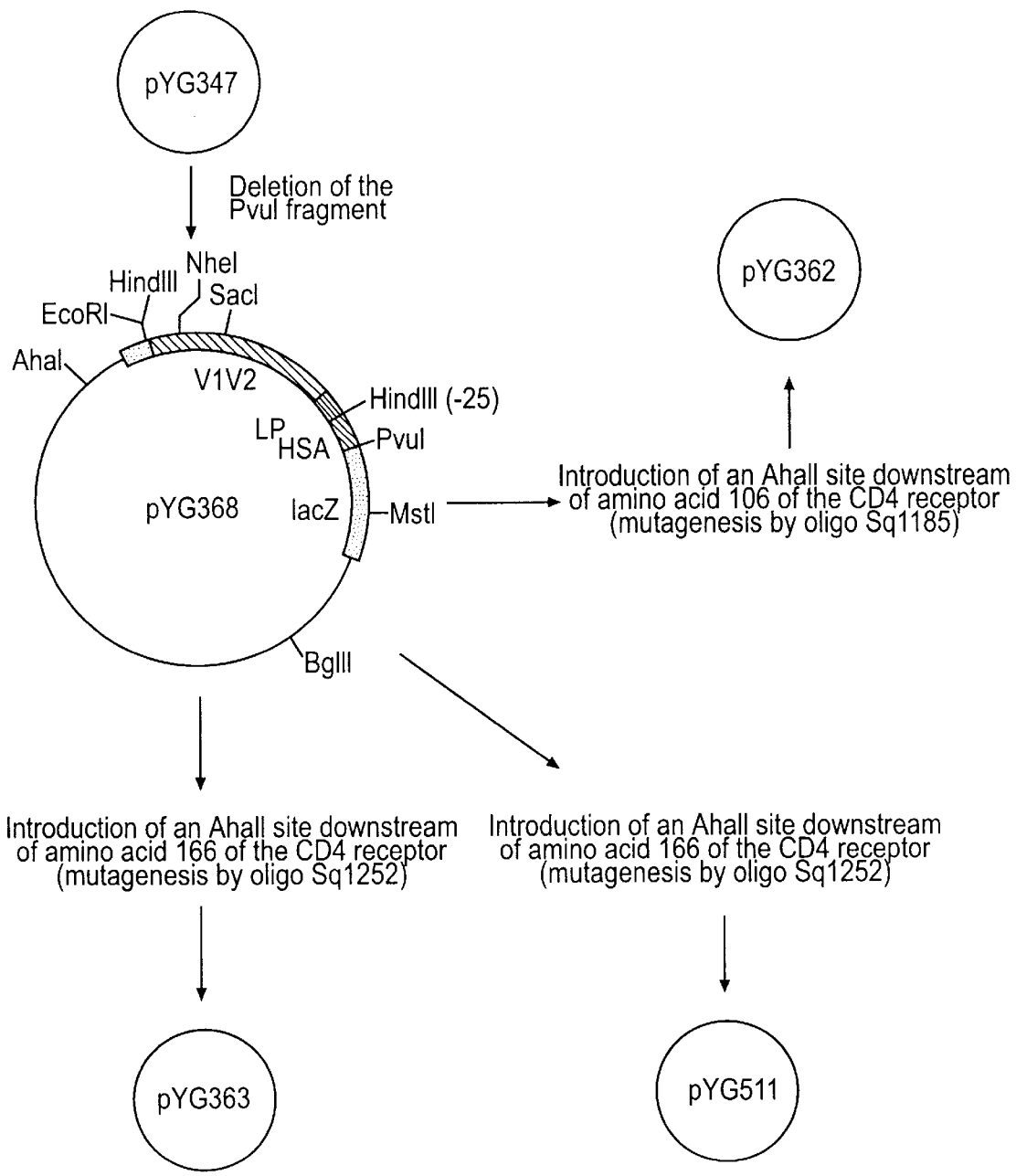
FIG. 28: Construction of plasmids pYG362, pYG363 and pYG511.

The introduction of an AhaII site at the end of the V2 domain of the CD4 receptor was accomplished by site-directed mutagenesis using oligodeoxynucleotide Sq1186 and plasmid pYG368, to generate plasmid pYG363 (FIG. 28). The sequence of oligodeoxynucleotide Sq1186 is (the AhaII site is shown in bold type): 5'-GCTAGCMCGACGCCCGGGGAATTCG-3'. Plasmid pYG363 therefore carries a HindIII-AhaII fragment composed of the 21 nucleotides preceding the ATG codon of the PGK gene of S. cerevisiae followed by the coding sequence for the HSA prepro region fused to the V1V2 domains of the CD4 receptor. In this particular fusion, the V1V2 domains contain 179 amino acids.

Other variants of plasmid pYG363 were generated by site-directed mutagenesis in order to introduce an AhaII at different places in the V2 domain of the CD4 receptor. In particular, plasmid pYG511, shown in FIG. 28, does not contain the amino acid pair Lys—Lys at positions 166–167 of the V2 domain; this is due to the oligodeoxynucleotide used (Sq1252; the AhaII site is shown in bold type):

5'-GCAGAACCAGAAGGACGCCAAGGTGGAGTTC-3'.

E.11.5. Generic constructions of the type V1-HSA.

Figure 29:
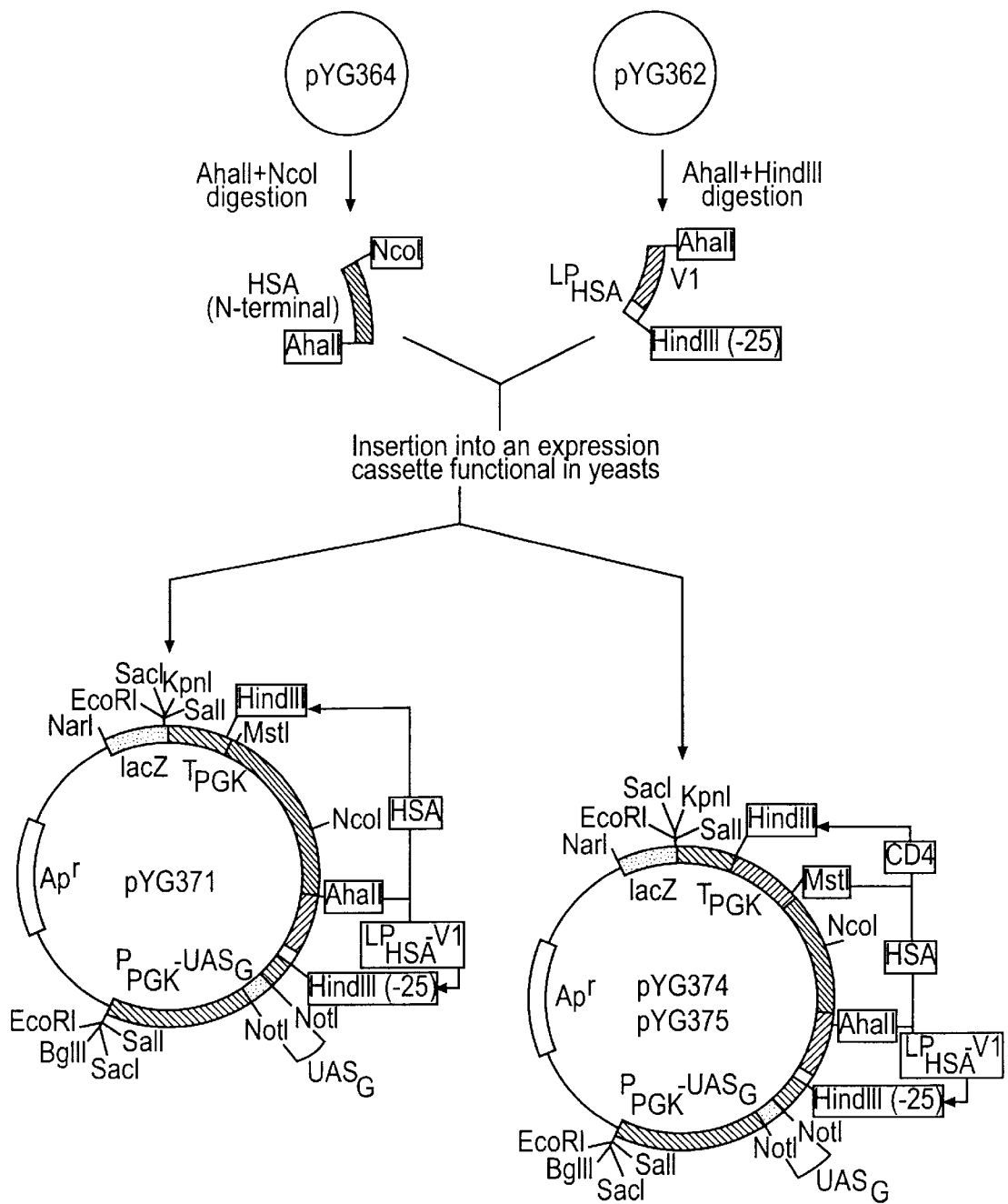
FIG. 29: Restriction maps of plasmids pYG371, pYG374 and pYG375.
Figure 30:
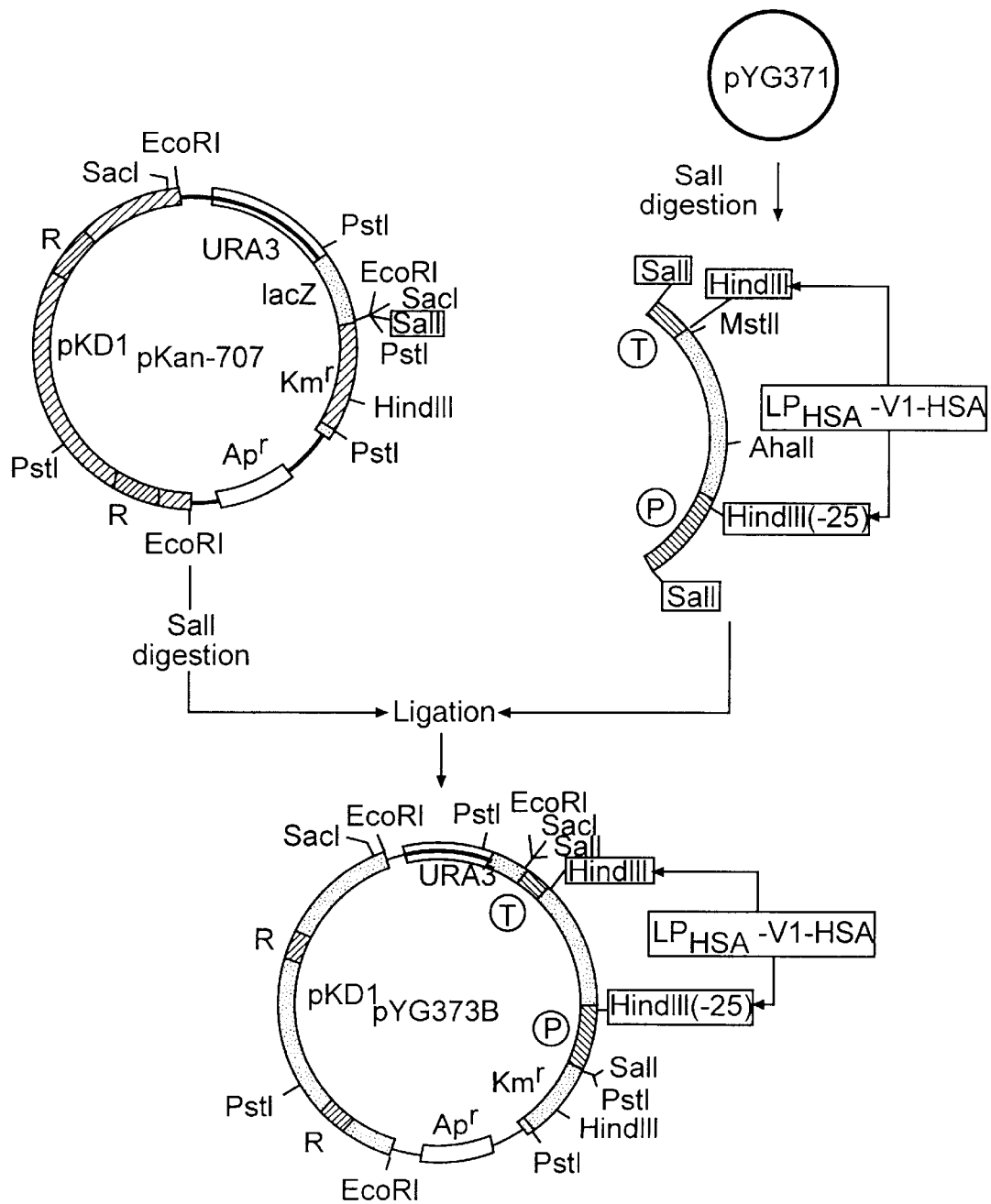
FIG. 30: Restriction map of expression plasmid pYG373B.

The plasmids described in the preceding examples allow for the generation of HindIII restriction fragments coding for hybrid proteins in which the receptor of the HIV-1 virus (fused to the signal sequence of HSA) precedes HSA. For example, plasmids pYG362 and PYG364 are respectively the source of a HindIII-AhaII fragment (fusion of the HSA prepro region to the V1 domain of the CD4 receptor), and an AhaII-NcoI fragment (N-terminal region of mature HSA obtained as in example E.11.1.). The ligation of these fragments with the NcoI-KpnI fragment (C-terminal region of HSA and terminator of the PGK gene of S. cerevisiae) in an analogue of plasmid pYG18 cut by HindIII and KpnI generates plasmid pYG371 whose structure is shown in FIG. 29. In this plasmid, the gene coding for the hybrid protein V1-HSA fused to the HSA prepro region is cloned into an expression cassette functional in yeasts. This cassette can then be cloned into a replicative vector that can be selected in yeasts, for example the vector pKan707, which generates expression plasmid pYG373B (FIG. 30).

E.11.6. Generic constructions of the type V1V2-HSA.

Figure 31:
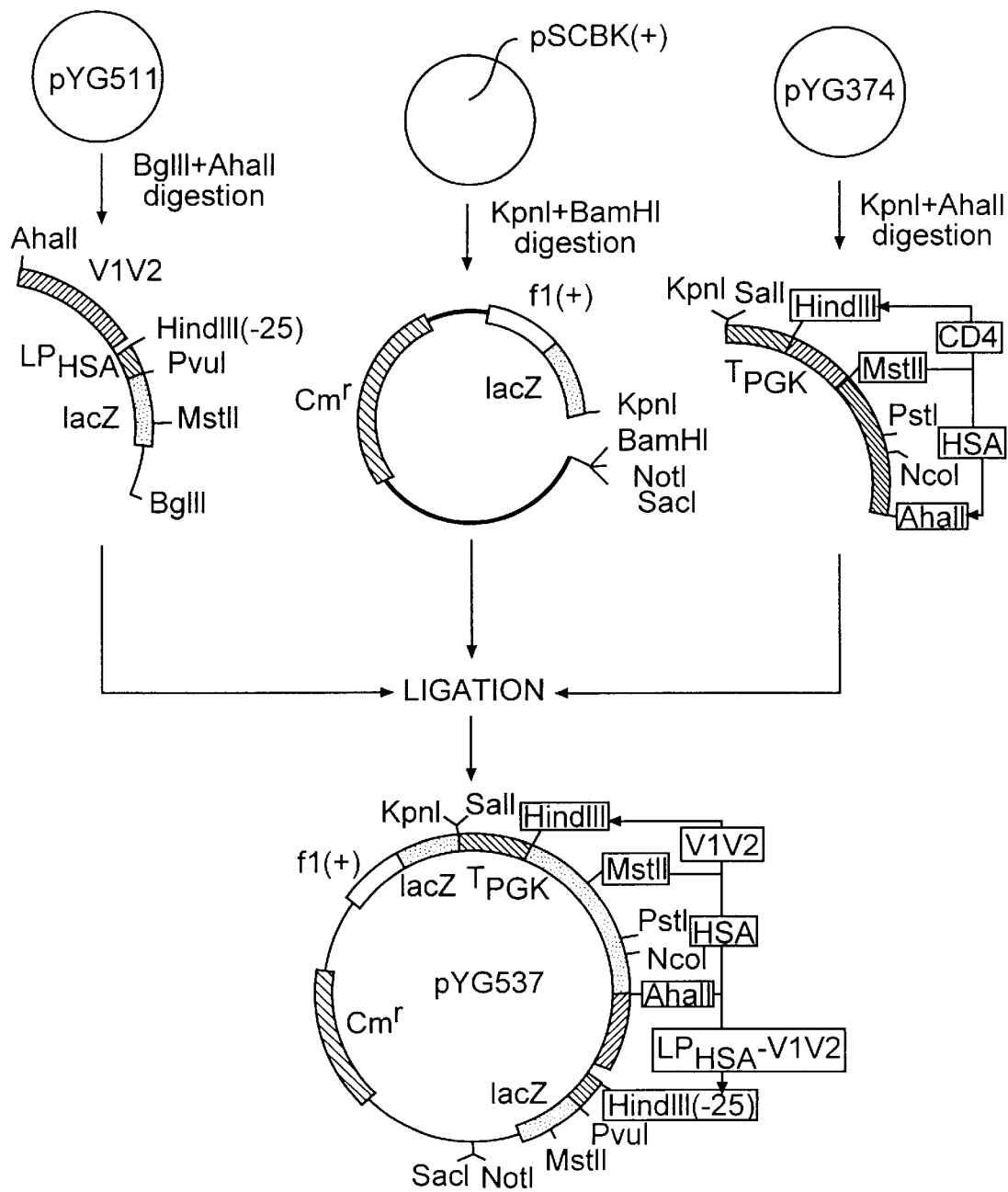
FIG. 31: Construction of plasmid pYG537.
Figure 32:
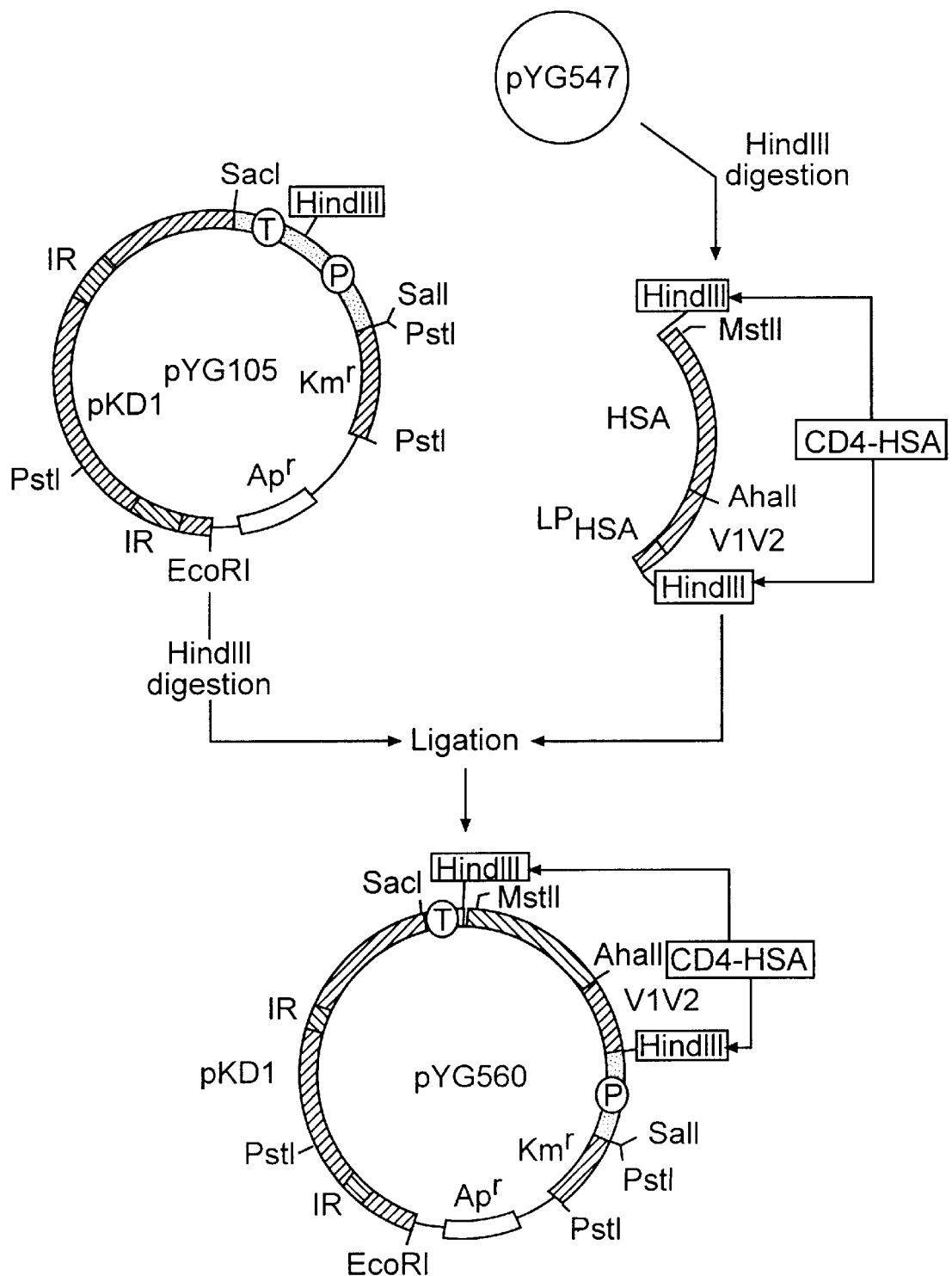
FIG. 32: Construction of expression plasmid pYG560.

Hybrid proteins of the type V1V2-HSA were generated by the following strategy: in a first step, plasmids pYG511 (FIG. 28) and pYG374 (FIG. 29) were respectively the source of the restriction fragments BglII-AhaII (fusion of the HSA prepro region and the V1V2 domains of the CD4 receptor) and AhaII-KpnI (in-frame fusion between mature HSA and the V1V2 domains of the CD4 receptor as exemplified in E.12.2.). Ligation of these fragments in a chloramphenicol resistant derivative of pBluescript II SK(+) vector (plasmid pSCBK(+), Stratagene) generates plasmid pYG537 (FIG. 31). This plasmid contains a HindIII fragment coding for the hybrid bivalent molecule CD4-HSA-CD4 fused in-frame with the signal peptide of HSA as exemplified in E.11.2. Plasmid pYG547 which contains a HindIII fragment coding for the hybrid protein V1V2-HSA fused in-frame with the prepro region of HSA, was then derived by substitution of the PstI-KpnI fragment of pYG537 by the PstI-KpnI fragment from plasmid pYG371. The HindIII fragment carried by plasmid pYG547 can then be expressed under control of a functional yeast promoter cloned in a vector that replicates, for example, in yeasts of the genus Kluyveromyces. One example is the expression plasmid pYG560 whose structure and restriction map are shown in FIG. 32. Vector pYG105 used in this particular example corresponds to plasmid pKan707 whose HindIII site has been destroyed by site-directed mutagenesis (oligodeoxynucleotide Sq1053, 5'-GAAATGCATAAGCTCTTGCCATTCTCACCG-3') and whose SalI-SacI fragment coding for the URA3 gene has been replaced by a SalI-SacI fragment carrying a cassette made up of a promoter, a terminator, and a unique HindIII site.

Example 12

BIVALENT HYBRID PROTEIN COMPLEXES

E.12.1. Introduction of a stop codon downstream of the V1 domain of the CD4 receptor.

Conventional techniques permit the introduction of a translation stop codon downstream of the domain of the CD4 receptor which is responsible for the binding of the HIV-1 viral glycoprotein gp120. For example, a TAA codon, immediately followed by a HindIII site, was introduced by site-directed mutagenesis downstream of the V1 domain of the CD4 receptor. In particular, the TAA codon was placed immediately after the amino acid in position 106 of the CD4 receptor (Thr$^{106}$) using oligodeoxynucleotide Sq1034 and a plasmid analogous to plasmid M13-CD4 as matrix. The sequence of oligodeoxynucleotide Sq1034 is (the stop codon and the HindIII site are in bold type):

```
5'-ACTGCCAACTCTGACACCTAAAAGCTTG-
   GATCCCACCTGCTFCAGGGGCAG-3'
```

E.12.2. Constructions of the type CD4-HSA-CD4.

Figure 33:
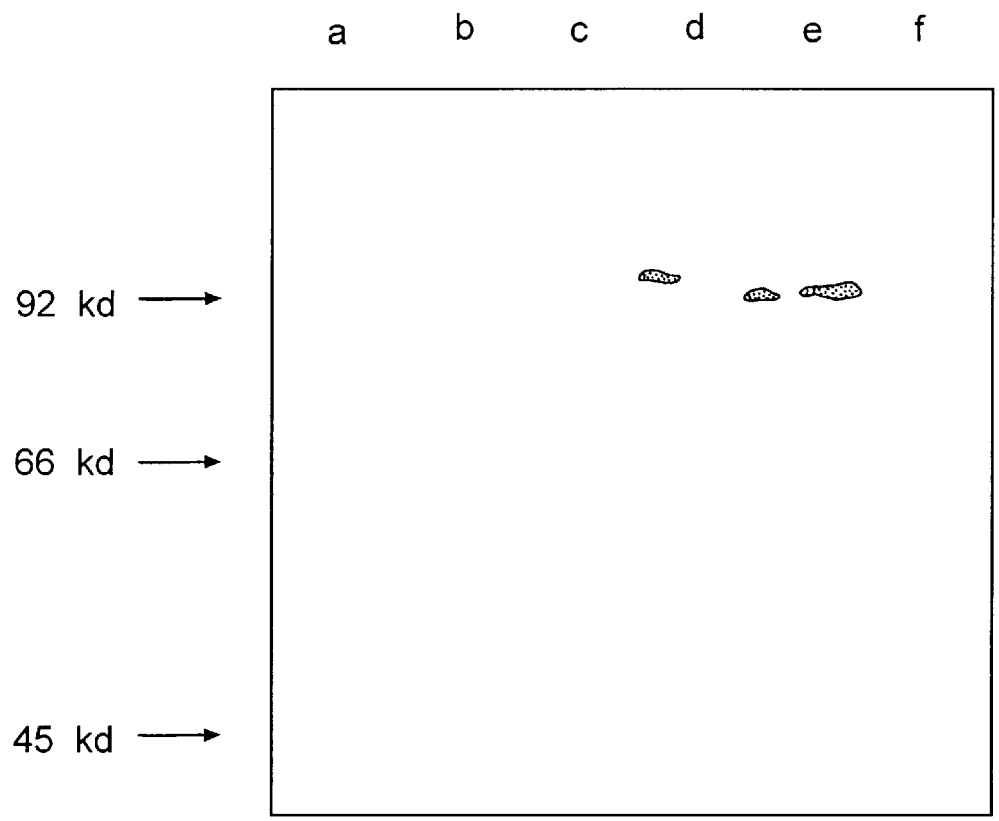
FIG. 33: Intracellular expression of hybrid proteins HSA-V1 (plasmid pYG366B; lane b), V1-HSA (plasmid pYG373B; lane c), V1-HAS-V1V2 (plasmid pYG380B; lane d), V1-HSA-V1 (plasmid pYG381B, lane e) and HSA-V1V2 (plasmid pYG308B, lane f) in K. lactis strain MW98-8C. Detection was performed by the Western Blot method using polyclonal rabbit serum directed against HSA as primary antibody. 10 µg of protein from the insoluble fraction was loaded in each case.

The plasmids described in examples E.11.5. et E.11.6. which exemplify generic constructions of the type CD4-HSA allow for the easy generation of bivalent constructions of the type CD4-HSA-CD4. Plasmids pYG374 (V1-HSA-V1V2) or pYG375 (V1-HSA-V1) illustrate two of these generic constructions: for example, the small MstII-HindIII fragment of plasmid pYG371 which codes for the last amino acids of HSA can be replaced by the MstII-HindIII fragment coding for the last 3 amino acids of HSA fused to the V1V2 domains of the CD4 receptor (plasmid pYG374, FIG. 29), or to the V1 domain alone (plasmid pYG375, FIG. 29). The genes coding for such bivalent hybrid proteins can then be expressed under control of a functional yeast promoter that replicates, for example, in yeasts of the genus Kluyveromyces. Examples of such expression plasmids are the plasmids pYG380B (V1-HSA-V1V2) and pYG381B (V1-HSA-V1) which are strictly isogenic to plasmid pYG373B (V1-HSA) except for the structural genes encoded in the HindIII fragments. The bivalent hybrid proteins described here are expressed at levels comparable to their monovalent equivalents, indicating a very weak level of recombination of the repeated sequences resulting from genetic recombination in vivo (FIG. 33).

The construction of HindIII fragments coding for bivalent hybrid proteins of the type V1V2-HSA-V1V2 has already been described in FIG. 31 (plasmid pYG537). The genes coding for such bivalent hybrid proteins of the type CD4-HAS-CD4 can then be expressed under control of a functional yeast promoter in a vector that replicates, for example, in yeasts of the genus Kluyveromyces. Such expression plasmids are generated by the strategy described in FIG. 32 (cloning of a HindIII fragment into plasmids analogous to plasmid pYG560).

E.12.3. Introduction of a dimerization domain.

For a given hybrid protein derived from albumin and carrying one or several binding sites for the HIV-1 virus, it may be desirable to include a polypeptide conferring a dimerization function, which allows for the agglomeration of trapped virus particles. An example of such a dimerization function is the "Leucine Zipper" (LZ) domain present in certain transcription regulatory proteins (JUN, FOS . . . ). In particular, it is possible to generate a BglII-AhaII fragment coding, for example, for the LZ of JUN, by the PCR technique by using the following oligodeoxynucleotides and the plasmid pTS301 (which codes for an in-frame fusion between the bacterial protein LexA and the LZ of JUN, T. Schmidt and M. Schnar, unpublished results) as matrix (BglII and AhaII sites are underlined):

```
5'-GGTAGGTCGTGTG
   GACGCCAGATCTTTGGAAAGAATTGCCCGTCTGCAAG-3'

5'-CTGCAGGTTA
   GGCGTCGCCAACCAGTTGCTTCAGCTGTGC-3'
```

Figure 34:
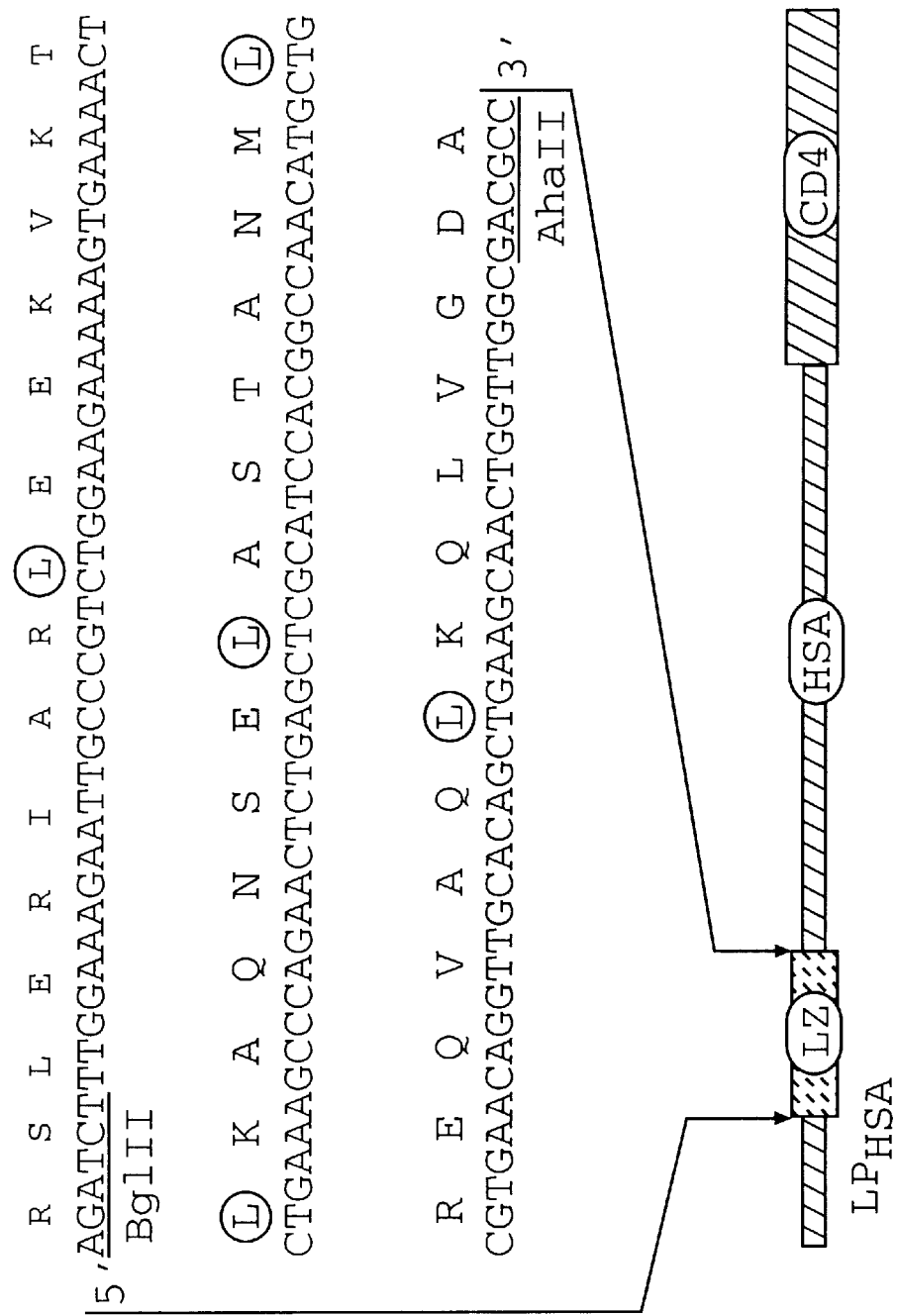
FIG. 34: Introduction of the "Leucine Zipper" of c-jun (BglIII-AhaII fragment) in a hybrid protein HSA-CD4.

This BglII-AhaII fragment (FIG. 34) can be ligated to the HindIII-BglII fragment of plasmid pYG233 (HSA prepro region, FIG. 25) and the AhaII-HindIII fragment as shown in one of the examples E.11. to generate a HindIII fragment coding for hybrid proteins of the type LZ-HSA-CD4, fused to the signal sequence of HSA. To prevent a possible dimerization of these molecules during their transit through the yeast secretory pathway, it may be desirable to utilize a LZ domain which cannot form homodimers. In this case the "Leucine Zipper" of FOS is preferred; dimerization would then result when these proteins are placed in the presence of other hybrid proteins carrying the LZ of JUN.

The introduction of carefully selected restriction sites that permit the construction of genes coding for hybrid proteins of the type LZ-CD4-HSA or LZ-CD4-HSA-CD4 is also possible, using conventional in vitro mutagenesis techniques or by PCR.

Example 13

GENETIC ENGINEERING OF THE HINGE REGION BETWEEN THE CD4 AND HSA MOIETIES

E.13.1. Strategy using Bal31 exonuclease.

Proteins secreted by strain MW98-8C transformed by expression plasmids for HSA-CD4 hybrid proteins in which the CD4 moiety is carried on the MstII-HindIII fragment in the natural MstII site of HSA (plasmid pYG308B for example), were analyzed. FIG. 35 demonstrates the presence of at least two cleavage products comigrating with the albumin standard (panel 2), which have a mature HSA N-terminal sequence, and which are not detectabe using polyclonal antibodies directed against human CD4 (panels 2 and 3). It is shown that these cleavage products are generated during transit through the yeast secretory pathway, probably by the KEX1 enzyme of *K. lactis* (or another protease with a specificity analogous to the endoprotease YAP3 of *S. cerevisiae* whose gene has been cloned and sequenced (Egel-Mitani M. et al. Yeast 6 (1990) 127–137). Therefore, the peptide environment of the hinge region between the HSA and CD4 moieties was modified, notably by fusion of the CD4 molecule (or one of its variants capable of binding the gp120 protein of HIV-1) to HSA N-terminal regions of varying length, according to the following strategy: plasmid pYG400 is an intermediate plasmid carrying the prepro-HSA gene, optimized with respect to the nucleotide sequence upstream of the ATG codon, on a HindIII fragment. This plasmid was linearized at its unique MstII site and partially digested by Bal31 exonuclease. After inactivation of this enzyme, the reaction mixture was treated with the Klenow fragment of *E. coli* DNA polymerase I and then subjected to ligation in the presence of an equimolar mixture of oligodeoxynucleotides Sq1462 (5'-GATCCCCTAAGG-3') and Sq1463 (5'-CCTTAGGG-3') which together form a synthetic adaptor containing a MstII site preceding a BamHI site. After ligation, the reaction mixture was digested with HindIII and BamHI and fragments between 0.7 and 2.0 kb in size were separated by electroelution and cloned into an M13 mp19 vector cut by the same enzymes. 10⁶ lytic plaques were thus obtained of which approximately one-third gave a blue color in the presence of IPTG and XGAL. Phage clones which remained blue were then sequenced, and in most cases contained an in-frame fusion between the HSA N-terminal moiety and β-galactosidase. These composite genes therefore contain HindIII-MstII fragments carrying sections of the N-terminal of HSA; FIG. 36 shows several examples among the C-terminal two-thirds of HSA. These fragments were then ligated with a MstII-HindIII fragment corresponding to the CD4 moiety (for example the V1V2 domains of FIG. 2, or the V1 domain alone), which generates HindIII fragments coding for hybrid proteins of the type HSA-CD4 in which the HSA moiety is of varying length. These restriction fragments were then cloned in the proper orientation into an expression cassette carrying a yeast promoter and terminator, and the assembly was introduced into yeasts. After growth of the culture, the hybrid proteins HSA-CD4 can be obtained in the culture medium; certain of these hybrids have an increased resistance to proteolytic cleavage in the hinge region (FIG. 35).

E.13.2. Mutation of dibasic amino acid pairs.

Another way to prevent cleavage by endoproteases with specificity for dibasic amino add pairs is to suppress these sites in the area of the hinge region between the HSA and the CD4 moieties (FIG. 37), or in the area of the hinge region between CD4 and HSA (FIG. 38). As an example, the hinge region present in the hybrid protein HSA-V1V2 coded by plasmid pYG308B is represented in FIG. 37 (panel 1), and points out the presence of a Lys-Lys pair in the C-terminal of HSA and two such pairs in the N-terminal of the V1 domain of CD4. Using site-directed mutagenesis, these potential endoprotease cleavage sites can be suppressed by changing the second lysine in each pair to a glutamine (Risler J. L et al., J. Mol. Biol. 204 (1988) 1019–1029), for example by using plasmid M13-ompA-CD4 as matrix and the oligodeoxynucleotides Sq1090 and Sq1091 (the codons specifying glutamine are in bold type):

5'-GTGCTGGGCAAACAAGGGGATACAG-3'

5'-GGCTTAAAGCAAGTGGTGCTG-3'

Plasmid M13-ompA-CD4 is a derivative of plasmid M13-CD4 in which the signal sequence of the ompA gene of E. coli is fused in frame to the CD4 receptor using the MstII site generated by PCR upstream of the V1 domain (example 1).

E13.3. Introduction of a synthetic hinge region.

In order to promote an optimal interaction between the CD4 moiety fused to HSA, and the gp120 protein of the HIV-1 virus, it may be desirable to correctly space the two protein moieties which form the building blocks of the hybrid protein HSA-CD4. For example, a synthetic hinge region can be created between the HSA and CD4 moieties by site-directed mutagenesis to introduce a fragment of troponin C between amino acids 572 and 582 of mature HSA (FIG. 37, panel 3). In this particular example, the junction peptide was introduced via site-directed mutagenesis by using a recombinant M13 phage (carrying the PstI-SacI fragment coding for the in-frame fusion between the C-terminal portion of HSA and the C-terminal part of the CD4 receptor) as matrix and oligodeoxynucleotide Sq1445:

5'-TGCTTTGCCGAGGAGGGTAAGGAA-
GACGCTAAGGGTAAGTCTGAAGAA-
GAAGCCTTAGGCTTAAAGAAA-3'.

Similar techniques also permit the introduction of such a synthetic hinge region between the HSA and CD4 moieties (junction peptide, FIG. 38, panel 3).

Example 14

EXPRESSION OF HYBRID PROTEINS UNDER THE CONTROL OF DIFFERENT PROMOTERS

For a given protein secreted by cells at high levels, there exists a threshold above which the level of expression is incompatible with cell survival. Hence there exist certain combinations of secreted protein, promoter utilized to control its expression, and genetic background that are optimal for the most efficient and least costly production. It is therefore important to be able to express the hybrid proteins which are the object of the present invention under the control of various promoters. The composite genes coding for these proteins are generally carried on a HindIII restriction fragment that can be cloned in the proper orientation into the HindIII site of a functional expression cassette of vectors that replicate in yeasts. The expression cassette can contain promoters that allow for constitutive or regulated expression of the hybrid protein, depending on the level of expression desired. Examples of plasmids with these characteristics include plasmid pYG105 (LAC4 promoter of *K. lactis*, FIG. 32), plasmid pYG106 (PGK promoter of *S. cerevisiae*), or plasmid pYG536 (PHO5 promoter of *S. cerevisiae*) etc. . . . In addition, hybrid promoters can be used in which the UAS regions of tightly regulated promoters have been added, such as the hybrid promoters carried by plasmids pYG44 (PGK/LAC hybrid, European patent application EP N° 89 10480), pYG373B (PGK/GAL hybrid), pYG258 (PHO5/LAC hybrid) etc. . . .

What is claimed is:

1. A hybrid peptide comprising the $V_1$ domain or $V_1V_2$ domains of the CD4 receptor of a human immunodeficiency virus, wherein the N-terminal end of said domain or domains is covalently coupled to albumin or a derivative of albumin.

2. A hybrid peptide according to claim 1, wherein said hybrid peptide lacks one or more proteolytic cleavage sites between the $V_1$ domain or $V_1V_2$ domains of CD4 and albumin or a derivative of albumin.

3. A hybrid peptide according to claim 1, wherein said albumin is of human origin.

4. A hybrid peptide comprising the $V_1$ domain or $V_1V_2$ domains of the CD4 receptor of a human immunodeficiency virus, wherein said domain or domains are covalently coupled to albumin or a derivative of albumin, and a polypeptide region conferring a dimerization or polymerization function.

5. A hybrid peptide according to claim 1, wherein the covalent coupling comprises a peptide linkage.

6. A hybrid peptide according to any one of claims 1, 2, 3, 4, or 5 together with a pharmaceutically acceptable vehicle.

7. A hybrid peptide comprising the $V_1$ domain or $V_1V_2$ domains of the CD4 receptor of a human immunodeficiency virus, wherein said domain or domains are covalently coupled to albumin or a derivative of albumin and further comprising a leucine zipper domain.

8. A hybrid peptide comprising the $V_1$ domain or $V_1V_2$ domains of the CD4 receptor of a human immunodeficiency virus, wherein the N-terminal end of said domain or domains is covalently coupled to human albumin.

9. A hybrid peptide according to claim 8, wherein said hybrid peptide is a secretory peptide, which binds to an OKT4A antibody, a Leu3A antibody, and polyclonal anti-human serum albumin antibodies.

10. A hybrid peptide according to any one of claims 7, or 9 together with a pharmaceutically acceptable vehicle.

11. A hybrid peptide according to claim 1, further comprising a hinge region between the albumin or albumin derivative and the $V_1$ domain or $V_1V_2$ domains.

12. A hybrid peptide according to claim 8, further comprising a hinge region between the albumin and the $V_1$ domain or $V_1V_2$ domains.

13. A hybrid peptide according to claim 1, wherein the half-life of the hybrid peptide, which has been injected into a rabbit, is 34 hours ±4 hours.

14. A hybrid peptide according to claim 8 or claim 12, wherein the half-life of the hybrid peptide, which has been injected into a rabbit, is 34 hours ±4 hours.

15. A hybrid peptide according to claim 14, wherein said hybrid peptide is a secretory peptide, which binds to an OKT4A antibody, a Leu3A antibody, and polyclonal anti-human serum albumin antibodies.

* * * * *

UNITED STATES PATENT AND TRADEMARK OFFICE
CERTIFICATE OF CORRECTION

PATENT NO. : 6,165,470
DATED : December 26, 2000
INVENTOR(S) : Jérôme Becquart et al.

Page 1 of 1

It is certified that error appears in the above-identified patent and that said Letters Patent is hereby corrected as shown below:

Title page,
Item [73], "Assignee: Rhone-Poulenc" should read -- Assignee: Rhone-Poulenc Sante --.

Column 28, claim 10,
Lines 66-67, "claim 7, or 9" should read -- claims 7, 8, or 9 --.

Column 29, claim 13,
Lines 7-9, "wherein the half-life of the hybrid peptide, which has been injected into a rabbit, is 34 hours ± 4 hours" should read -- which has a half life of 34 hours ± 4 hours in a rabbit --.

Column 30, claim 14,
Lines 2-3, "wherein the half-life of hybrid peptide, which has been injected into a rabbit, is 34 hours ± 4 hours" should read -- which has a half-life of 34 hours ± 4 hours --.

Signed and Sealed this

Eleventh Day of December, 2001

*Attest:*

NICHOLAS P. GODICI
*Attesting Officer*   *Acting Director of the United States Patent and Trademark Office*